United States Patent
Shi et al.

(10) Patent No.: US 11,686,725 B2
(45) Date of Patent: Jun. 27, 2023

(54) DETECTION AND TREATMENT OF NEUROLOGICAL DISEASES

(71) Applicant: CITY OF HOPE, Duarte, CA (US)

(72) Inventors: Yanhong Shi, Arcadia, CA (US); Li Li, Glendale, CA (US)

(73) Assignee: CITY OF HOPE, Duarte, CA (US)

( * ) Notice: Subject to any disclaimer, the term of this patent is extended or adjusted under 35 U.S.C. 154(b) by 596 days.

(21) Appl. No.: 16/505,534

(22) Filed: Jul. 8, 2019

(65) Prior Publication Data
US 2020/0132674 A1    Apr. 30, 2020

Related U.S. Application Data

(60) Provisional application No. 62/713,475, filed on Aug. 1, 2018.

(51) Int. Cl.
| | |
|---|---|
| *G01N 33/50* | (2006.01) |
| *C12Q 1/6883* | (2018.01) |
| *C07K 16/28* | (2006.01) |
| *C12N 5/074* | (2010.01) |
| *C12N 5/079* | (2010.01) |
| *G16H 50/30* | (2018.01) |
| *A61K 31/7105* | (2006.01) |

(52) U.S. Cl.
CPC ....... *G01N 33/5058* (2013.01); *C12N 5/0622* (2013.01); *C12N 5/0696* (2013.01); *C12Q 1/6883* (2013.01); *G16H 50/30* (2018.01); *A61K 31/7105* (2013.01); *C07K 16/28* (2013.01); *C12N 2310/141* (2013.01); *C12N 2310/20* (2017.05); *G01N 2570/00* (2013.01); *G01N 2800/285* (2013.01); *G01N 2800/2821* (2013.01); *G01N 2800/2835* (2013.01)

(58) Field of Classification Search
CPC ........... G01N 33/5058; G01N 2570/00; G01N 2800/2821; G01N 2800/2835; G01N 2800/285; G01N 33/6896; C12N 5/0622; C12N 5/0696; C12N 2310/141; C12N 2310/20; C12N 2506/45; C12N 2510/00; C12N 2310/14; C12N 15/113; C12Q 1/6883; C12Q 2600/158; G16H 50/30; A61K 31/7105; C07K 16/28; C07K 16/40
See application file for complete search history.

(56) References Cited

PUBLICATIONS

Wade M., Journal of Biomolecular Screening, vol. 20(8) 1027-1039, 2015 (Year: 2015).*
Kampmann, M. Trends in Molecular Medicine, Jun. 2017, vol. 23, No. 6 (Year: 2017).*
Abbott, N. J., et al., "Astrocyte-endothelial interactions at the blood-brain barrier," Nat. Rev. Neurosci. 7:41-53 (2006).
Allen, N. J., et al., "Cell biology of astrocyte-synapse interactions," Neuron 96(3): 697-708 (2017).
Anders, S., et al., "HTSeq—a Python framework to work with high-throughput sequencing data," Bioinformatics 31(2):166-169 (2015).
Arion, D., et al., "Molecular evidence for increased expression of genes related to immune and chaperone function in the prefrontal cortex in schizophrenia," Biol. Psych. 62(7):711-721 (2007).
Benjamini, Y., et al., "Controlling the false discovery rate: A practical and powerful approach to multiple testing," J. R. Stat. Soc. Series B (Methodological) 57(1):289-300 (1995).
Bhardwaj, R., et al., "RelB/p50 complexes regulate cytokine-induced YKL-40 expression," J. Immunol. 194:2862-2870 (2015).
Bonneh-Barkay, D., et al., "In vivo CHI3L1 (YKL-40) expression in astrocytes in acute and chronic neurological diseases," J. Neuroinflammation 7:34 (2010).
Bonneh-Barkay, D., et al., "YKL-40 expression in traumatic brain injury: An initial analysis," J. Neurotrauma 27:1215-1223 (2010).
Bonneh-Barkay, D., et al., "Astrocyte and macrophage regulation of YKL-40 expression and cellular response in neuroinflammation," Brain Pathol. 22(4):530-546 (2012).
Botstein, D., et al., "Gene ontology: tool for the unification of biology," Nat. Genet. 25(1): 25-29 (2000).
Burman, J., et al., "YKL-40 is a CSF biomarker of intrathecal inflammation in secondary progressive multiple sclerosis," J. Neuroimmunol. 292:52-57 (2016).
Clarke, L. E., et al., "Emerging roles of astrocytes in neural circuit development," Nat. Rev. Neurosci. 14(5):311-321 (2013).
Colombo, E., et al., "Astrocytes: Key regulators of neuroinflammation," Trends in Immunology 37(9):608-620 (2016).
Craig-Schapiro, R., et al., "YKL-40: A novel prognostic fluid biomarker for preclinical Alzheimer's Disease," Biol. Psych. 68(10):903-912 (2010).
Cui, Q., et al., "Downregulation of TLX induces TET3 expression and inhibits glioblastoma stem cell self-renewal and tumorigenesis," Nat. Commun. 7:10637 (2016).
Cui, Q., et al., "m6A RNA methylation regulates the self-renewal and tumorigenesis of glioblastoma stem cells," Cell Rep. 18(11):2622-2634 (2017).
Domingues, H. S., et al., "Oligodendrocyte, astrocyte, and microglia crosstalk in myelin development, damage, and repair," Front. Cell Dev. Biol. 4:71 (2016).

(Continued)

*Primary Examiner* — Kimberly Ballard
*Assistant Examiner* — Stacey N Macfarlane
(74) *Attorney, Agent, or Firm* — Perkins Coie LLP; Lara J. Dueppen; Allison M. Glasunow

(57) ABSTRACT

Disclosed are methods of detecting abnormal expression of one or more genes associated with a neurological disease such as the Alexander disease, the Alzheimer's disease, the Parkinson disease, the Huntington disease, multiple sclerosis, and amyotrophic lateral sclerosis. The methods include performing a transcriptome analysis of the astrocytes derived from a patient and the astrocytes derived from a healthy control subject, thereby to determine one or more genes that are substantially differentially expressed. Also disclosed are methods of treating a neurological disease by correcting the abnormally expressed genes associated with the neurological disease.

7 Claims, 25 Drawing Sheets
(22 of 25 Drawing Sheet(s) Filed in Color)
Specification includes a Sequence Listing.

(56) References Cited

PUBLICATIONS

Douvaras, P., et al., "Generation and isolation of oligodendrocyte progenitor cells from human pluripotent stem cells," Nat. Protoc. 10(8):1143-1154 (2015).

Ehrlich, M., et al., "Rapid and efficient generation of oligodendrocytes from human induced pluripotent stem cells using transcription factors," PNAS 114:E2243-E2252 (2017).

Gispert, J. D., et al., "CSF YKL-40 and pTau181 are related to different cerebral morphometric patterns in early AD," Neurobiol. Aging 38:47-55 (2016).

Hagemann, T. L., et al., "Gene expression analysis in mice with elevated glial fibrillary acidic protein and Rosenthal fibers reveals a stress response followed by glial activation and neuronal dysfunction," Hum. Mol. Genet. 14(16):2443-2458 (2005).

Hagemann, T. L., et al., "Alexander disease-associated glial fibrillary acidic protein mutations in mice induce Rosenthal fiber formation and a white matter stress response," J. Neurosci. 26(43):11162-11173 (2006).

Harizi, H., et al., "The immunobiology of prostanoid receptor signaling in connecting innate and adaptive immunity," BioMed Res. Int. 2013:683405 (2013).

Hasel, P., et al., "Neurons and neuronal activity control gene expression in astrocytes to regulate their development and metabolism," Nat. Commun. 8:15132 (2017).

He, C. H., et al., "Chitinase 3-like 1 regulates cellular and tissue responses via IL-13 receptor α2," Cell Rep. 4(4):830-841 (2013).

Hinsinger, G., et al., "Chitinase 3-like proteins as diagnostic and prognostic biomarkers of multiple sclerosis," Multiple Sclerosis J. 21(10):1251-1261 (2015).

Hockemeyer, D., et al., "Induced pluripotent stem cells meet genome editing," Cell Stem Cell 18(5):573-586 (2016).

Hrvatin, S., et al., "MARIS: Method for analyzing RNA following intracellular sorting," PLoS One 9(3):e89459 (2014).

Hsu, F., et al., "The UCSC known genes," Bioinformatics 22(9):1036-1046 (2006).

Iwaki, T., et al., "αB-Crystallin is expressed in non-lenticular tissues and accumulates in Alexander's Disease brain," Cell 57:71-78 (1989).

Johnson, A. B., et al., "On-grid immunogold labeling of glial intermediate filaments in epoxy-embedded tissue," Am. J. Anat. 185:335-341 (1989).

Kim, D., et al., "TopHat2: accurate alignment of transcriptomes in the presence of insertions, deletions and gene fusions," Genome Biol. 14:R36 (2013).

Kime, C., et al., "Practical integration-free episomal methods for generating human induced pluripotent stem cells," Hum. Genet. 87:21.2.1-21.2.21 (2015).

Kiray, H., et al., "The multifaceted role of astrocytes in regulating myelination," Exp. Neurol. 283:541-549 (2016).

Kondo, T., et al., "Modeling Alexander disease with patient iPSCs reveals cellular and molecular pathology of astrocytes," Acta Neuropathol. Commun. 4:69 (2016).

Krencik, R., et al., "Specification of transplantable astroglial subtypes from human pluripotent stem cells," Nat. Biotechnol. 29(6):528-534 (2011).

Krencik, R., et al., "Directed differentiation of functional astroglial subtypes from human pluripotent stem cells," Nat. Protoc. 6(11):1710-1717 (2011).

Lancioitti, A., et al., "Astrocytes: Emerging stars in leukodystrophy pathogenesis," Transl. Neurosci. 4:2 (2013).

Lawrence, M., et al., "Software for computing and annotating genomic ranges," PLoS Comput. Biol. 9(8):e1003118 (2013).

Lee, C.M., et al., "IL-13Rα2 uses TMEM219 in chitinase 3-like-1-induced signalling and effector responses," Nat. Commun. 7:12752 (2016).

Lee, S., et al., "A culture system to study oligodendrocyte myelinationprocesses using engineered nanofibers," Nat. Methods 9(9):917-922 (2012).

Lee, S.H., et al., "Aggregation-prone GFAP mutation in Alexander disease validated using a zebrafish model," BMC Neurol. 17:175 (2017).

Li, L., et al., "Modeling neurological diseases using iPSC-derived neural cells: iPSC modeling of neurological diseases," Cell Tissue Res. 371(1):143-151 (2018).

Love, M. I., et al., "Moderated estimation of fold change and dispersion for RNA-seq data with DESeq2," Genome Biol. 15:550 (2014).

Marchetto, M. C., et al., "Induced pluripotent stem cells (iPSCs) and neurological disease modeling: progress and promises," Hum. Mol. Genet. 20(2):R109-R115 (2011).

Messing, A., et al., "Fatal encephalopathy with astrocyte inclusions in GFAP transgenic mice," Am. J. Pathol. 152(2):391-398 (1998).

Messing, A., et al., "Alexander disease: New insights from genetics," J. Neuropathol. Exp. Neurol. 60(6):563-573 (2001).

Messing, A., et al., "Strategies for treatment in Alexander disease," Neurotherapeutics 7:507-515 (2010).

Messing, A., et al., "Alexander disease," J. Neurosci. 32(15):5017-5023 (2012).

Molofsky, A. V., et al., "Astrocytes and disease: a neurodevelopmental perspective," Genes Dev. 26:891-907 (2012).

Murai, K., et al., "The TLX-miR-219 cascade regulates neural stem cell proliferation in neurodevelopment and schizophrenia iPSC model," Nat. Commun. 7:10965 (2016).

Olabarria, M., et al., "Astrocyte pathology in Alexander disease causes a marked inflammatory environment," Acta Neuropathol. 130:469-486 (2015).

Prust, M., et al., "GFAP mutations, age at onset, and clinical subtypes in Alexander disease," Neurol. 77:1287-1294 (2011).

Qu, Q., et al., "Orphan nuclear receptor TLX activates Wnt/β-catenin signalling to stimulate neural stem cell proliferation and self-renewal," Nat. Cell Biol. 12(1):31-39 (2010).

Ran, F. A., et al., "Double nicking by RNA-guided CRISPR Cas9 for enhanced genome editing specificity," Cell 154(6):1380-1389 (2013).

Ran, F. A., et al., "Genome engineering using the CRISPR-Cas9 system," Nat. Protoc. 8(11):2281-2308 (2013).

Rempe, D. A., et al., "Targeting glia for treatment of neurological disease," 7:335-337 (2010).

Sanfilippo, C., et al., "CHI3L1 and CHI3L2 overexpression in motor cortex and spinal cord of sALS patients," Mol. Cell. Neurosci. 85:162-169 (2017).

Shi, Y., et al., "Expression and function of orphan nuclear receptor TLX in adult neural stem cells," Nature 427:78-83 (2004).

Shi, Y., et al., "Induced pluripotent stem cell technology: a decade of progress," Nat. Rev. Drug Discov. 16(2):115-130 (2017).

Singh, S. K., et al., "A complex of nuclear factor I-X3 and STAT3 regulates astrocyte and glioma migration through the secreted glycoprotein YKL-40," J. Biol. Chem. 286(46):39893-39903 (2011).

Sloan, S. A., et al., "Human astrocyte maturation captured in 3D cerebral cortical spheroids derived from pluripotent stem cells," Neuron 95(4):779-790 (2017).

Sofroniew, M. V., et al., "Astrocytes: biology and pathology," Acta Neuropathol 119:7-35 (2010).

Takahashi, K., et al., "Induction of pluripotent stem cells from adult human fibroblasts by defined factors," Cell 131:861-872 (2007).

Taketomi, Y., et al., "Mast cell maturation is driven via a group III phospholipase A2-prostaglandin D2-DP1 receptor paracrine axis," Nat. Immunol. 14(6):554-563 (2013).

Tanaka, K., et al., English abstract of "Generation of mice with glial cell dysfunction," Brain Nerve 59(7):747-53 (2007). Article in Japanese.

Tanaka, K. F., et al., "Murine model of Alexander disease: Analysis of GFAP aggregate formation and its pathological significance," Glia 55:617-631 (2007).

Tomokane, N., et al., "Rosenthal fibers share epitopes with αB-crystallin, glial fibrillary acidic protein, and ubiquitin, but not with vimentin," Am. J. Pathol. 138:875-885 (1991).

Van Der Knaap, M. S., et al., "Alexander disease: Diagnosis with MR imaging," AJNR Am. J. Neuroradiol. 22:541-552 (2001).

Van Der Voorn, J. P., et al., "Unraveling pathology in juvenile Alexander disease: serial quantitative MR imaging and spectroscopy of white matter," Neuroradiology 51:669-675 (2009).

(56) References Cited

PUBLICATIONS

Verkhratsky, A., et al., "Neurological diseases as primary gliopathies: a reassessment of neurocentrism," ASN Neuro (2012) doi:10.1042/AN20120010.

Verkhratsky, A., et al., "Astrogliopathology in neurological, neurodevelopmental and psychiatric disorders," Neurobiol. Dis. 85:254-261 (2016).

Wang, L., et al., "Protein misfolding and oxidative stress promote glial-mediated neurodegeneration in an Alexander disease model," J. Neurosci. 31(8):2868-2877 (2011).

Wang, L., et al., "Nitric oxide mediates glial-induced neurodegeneration in Alexander disease," Nat. Commun. 6:8966 (2015).

Wen, Z., et al., "Synaptic dysregulation in a human iPS cell model of mental disorders," Nature 515(7527):414-418 (2014).

Young, M. D., et al., "MGeethnode ontology analysis for RNA-seq: accounting for selection bias," Genome Biol. 11:R14 (2010).

Yu, J., et al., "Induced pluripotent stem cell lines derived from human somatic cells," Science 318:1917-1920 (2007).

Zhang, Y., et al., "Purification and characterization of progenitor and mature human astrocytes reveals transcriptional and functional differences with mouse," Neuron 89(1):37-53 (2016).

Zhou, Y., et al., "Chitinase 3-like 1 suppresses injury and promotes fibroproliferative responses in mammalian lung fibrosis," Sci. Transl. Med. 6(240):240ra76 (2014).

Zhou, Y., et al., "Chitinase 3-like-1 and its receptors in Hermansky-Pudlak syndrome-associated lung disease," J. Clin. Invest. 125(8):3178-3192 (2015).

Elbashir, S. M., et al., "Functional anatomy of siRNAs for mediating efficient RNAi in *Drosophila melanogaster* embryo lysate," EMBO J. (2001) 20(23):6877-6888.

Fakhr, E., et al., "Precise and efficient siRNA design: a key point in competent gene silencing," Cancer Gene Therapy (2016) 23:73-82.

Li, L., et al., "GFAP mutations in astrocytes impair oligodendrocyte progenitor proliferation and myelination in an hiPSC model of Alexander Disease," Cell Stem Cell (2018) 23:239-251.

Reynolds, A., et al., "Rational siRNA design for RNA interference," Nat. Biotechnol. (2004) 22(3):326-330.

Ricci, G., et al., "Astrocyte-neuron interactions in neurological disorders," J. Biol. Phys. (2009) 35:317-336.

Ui-Tei, K., et al., "Guidelines for the selection of highly effective siRNA sequences for mammalian and chick RNA interference," Nucl. Acids Res. (2004) 32(3):936-948.

\* cited by examiner

Fig. 1A
| iPSC lines | GFAP Mutation |
| --- | --- |
| I90 | - |
| C1 | - |
| C3 | - |
| AxD825 | R239C |
| AxD997 | R79C |
| AxD999 | M73K |
| AxD999-CR | - |
Fig. 1B
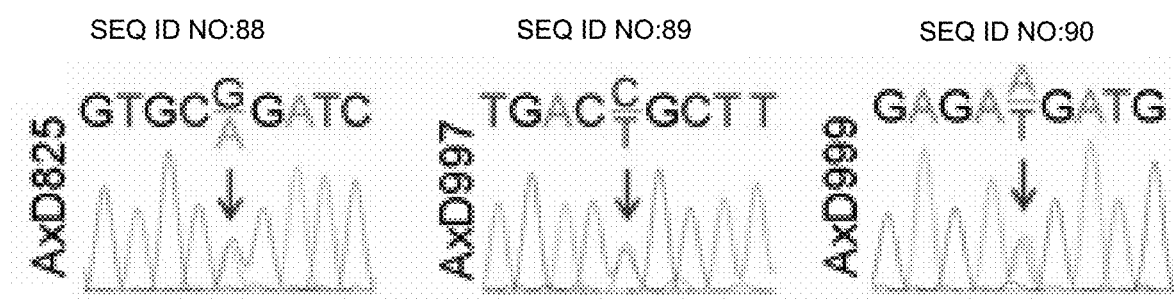
Fig. 1C
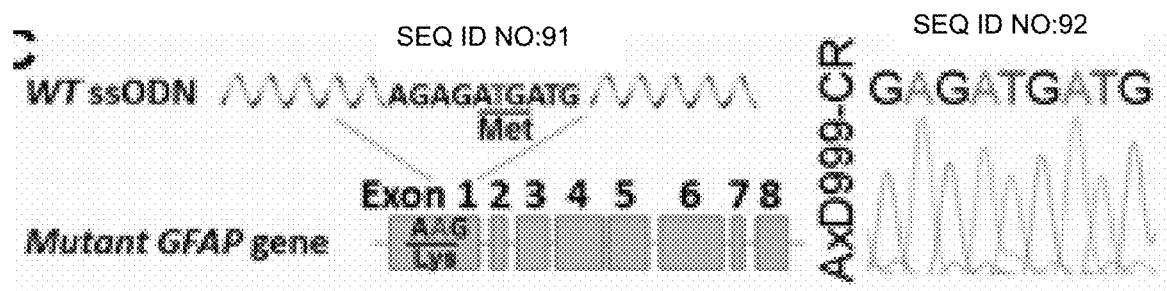

Fig. 3A    Fig. 3B    Fig. 3C
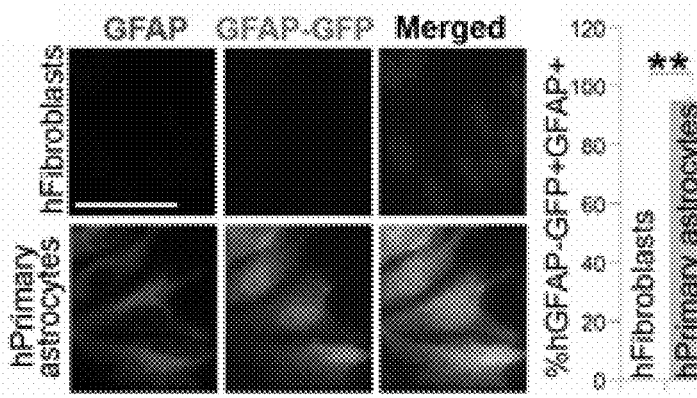
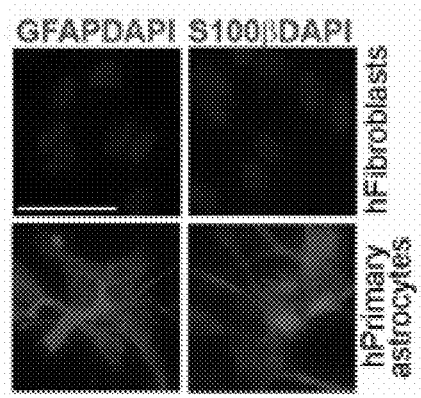
Fig. 3D
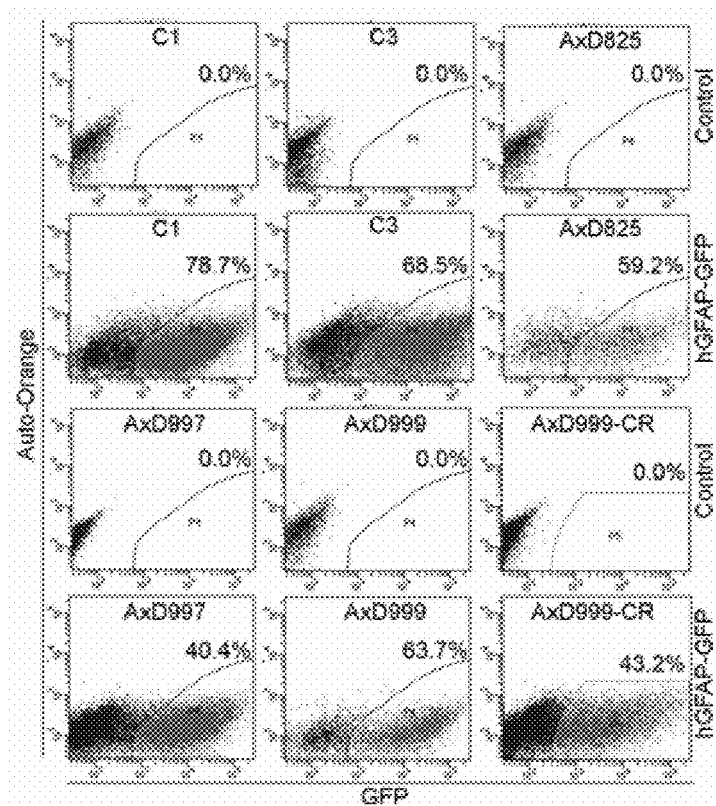

Fig. 5A
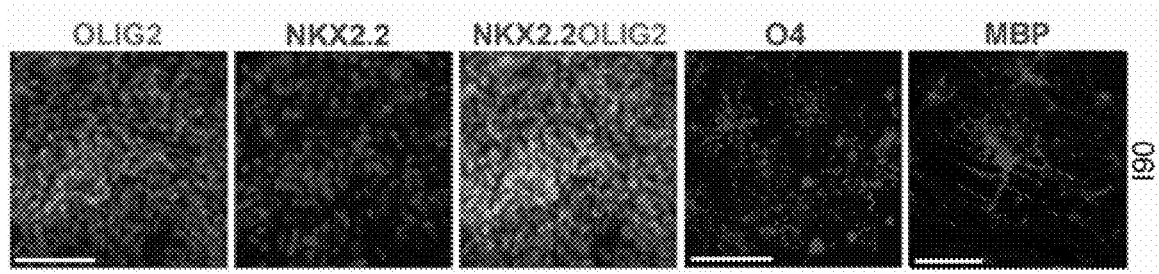
Fig. 5B
Fig. 5C
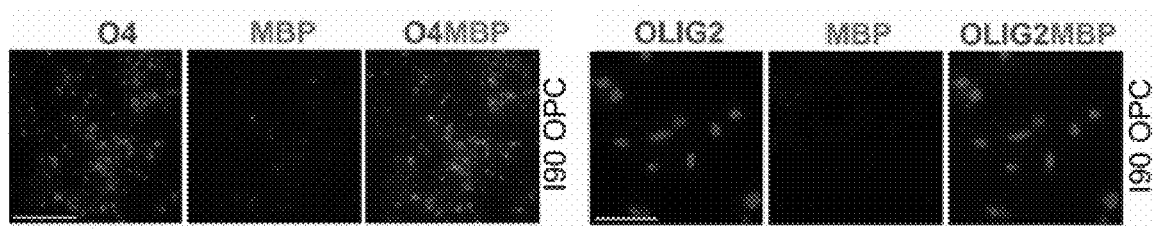
Fig. 5D
Fig. 5E
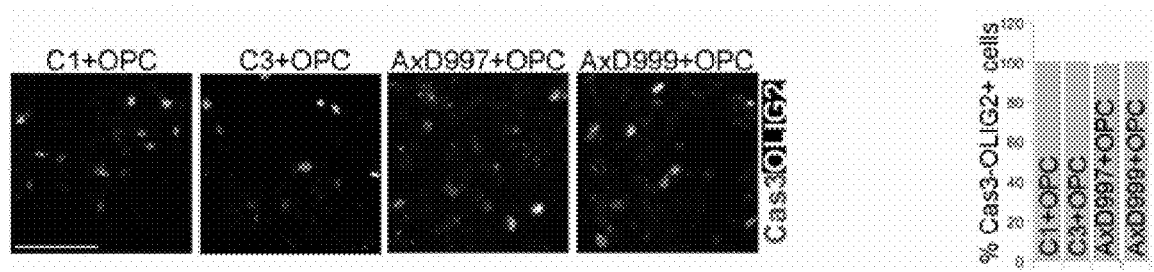
Fig. 5F
Fig. 5G

Fig. 6J
Fig. 6K
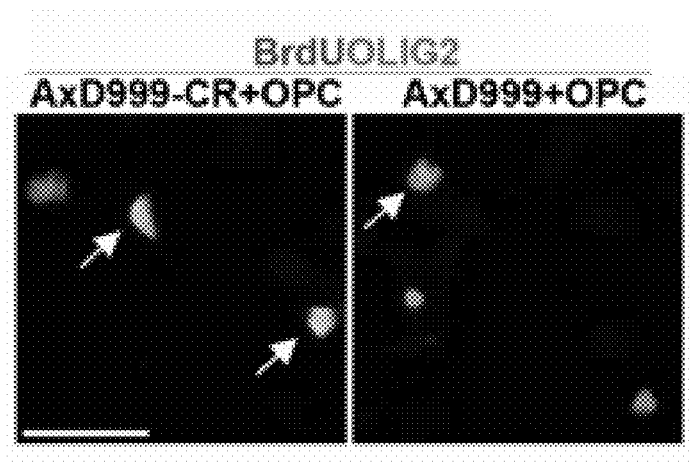
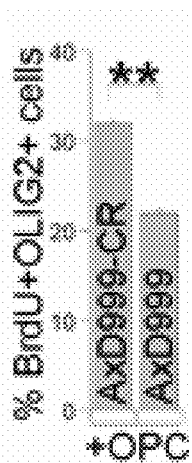

Fig. 7C                     Fig. 7D

Fig. 10A
| Disorder | Age (y) | Sex | Cause of death |
|---|---|---|---|
| AxD | 0 | Female | Complications of disorder |
| AxD | 0 | Female | Complications of disorder |
| AxD | 0 | Male | Complications of disorder |
| AxD | 1 | Female | Complications of disorder |
| AxD | 2 | Male | Complications of disorder |
| Control | 0 | Male | Hyperthermia |
| Control | 2 | Female | Accident |
| Control | 4 | Female | Asthma |
Fig. 10B
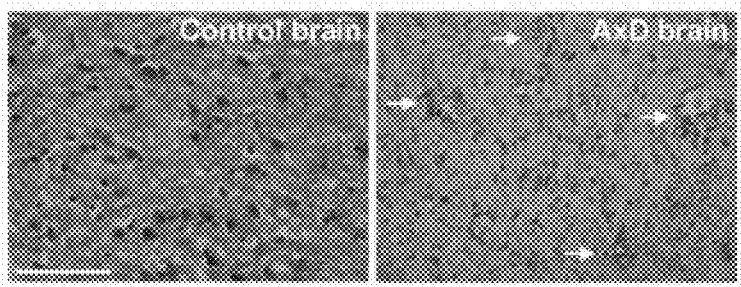
Fig. 10C
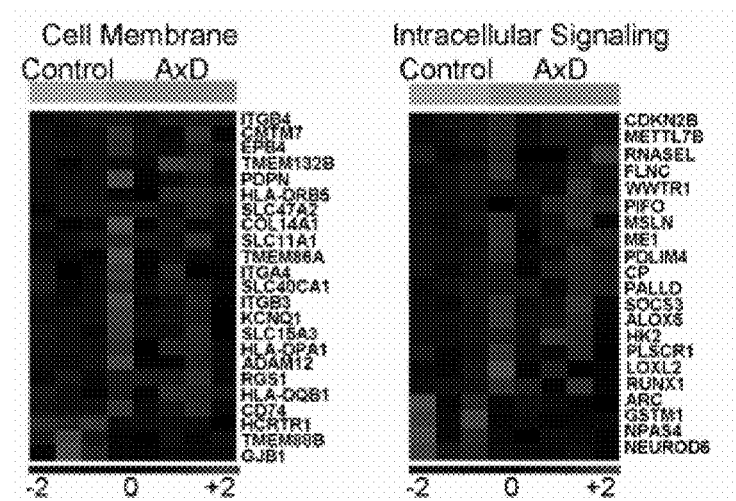

Fig. 12F
Fig. 12G
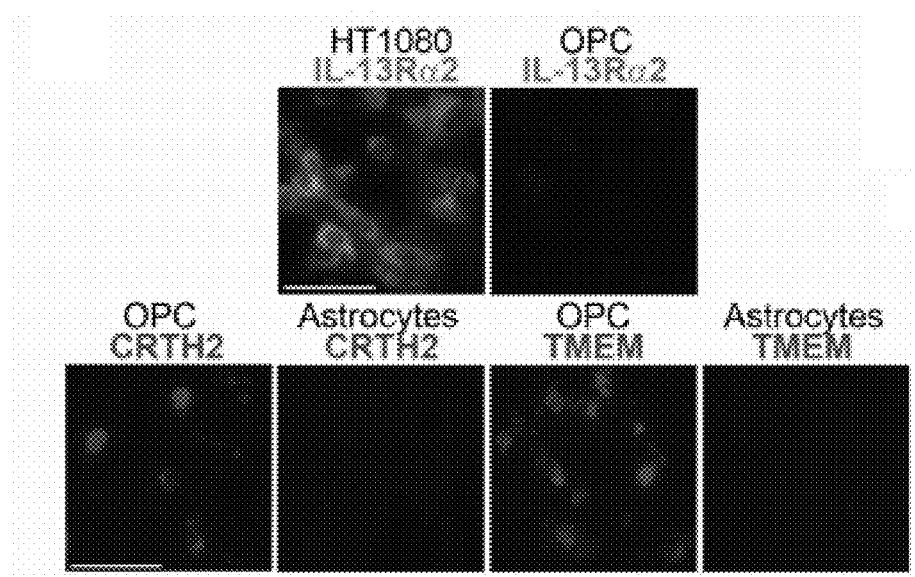
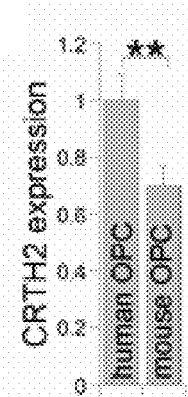

SEQUENCE LISTING

<160> NUMBER OF SEQ ID NOS: 92

<210> SEQ ID NO 1
<211> LENGTH: 20
<212> TYPE: DNA
<213> ORGANISM: Artificial Sequence
<220> FEATURE:
<223> OTHER INFORMATION: sgRNA target-3 primer

<400> SEQUENCE: 1
catcatctct gcccgctcac                                              20

<210> SEQ ID NO 2
<211> LENGTH: 20

-continued

```
<212> TYPE: DNA
<213> ORGANISM: Artificial Sequence
<220> FEATURE:
<223> OTHER INFORMATION: sgRNA target-4 primer

<400> SEQUENCE: 2
ctttgccagc tacatcgaga                                               20

<210> SEQ ID NO 3
<211> LENGTH: 200
<212> TYPE: DNA
<213> ORGANISM: Artificial Sequence
<220> FEATURE:
<223> OTHER INFORMATION: ssODN primer

<400> SEQUENCE: 3
ctcgaatgcc ccctccactc ccgacccggg tggatttctc cctggctggg gcactcaatg    60
ctggcttcaa ggagacccgg gctagtgagc gggcagagat gatggagctc aatgaccggt   120
ttgccagcta catcgagaaa gttcgcttcc tggaacagca aaacaaggcg ctggctgctg   180
agctgaacca gctgcgggcc                                              200

<210> SEQ ID NO 4
<211> LENGTH: 21
<212> TYPE: DNA
<213> ORGANISM: Artificial Sequence
<220> FEATURE:
<223> OTHER INFORMATION: GFAP M73K and R79C forward primer

<400> SEQUENCE: 4
ctccttcata aagccctcgc a                                             21

<210> SEQ ID NO 5
<211> LENGTH: 22
<212> TYPE: DNA
<213> ORGANISM: Artificial Sequence
<220> FEATURE:
<223> OTHER INFORMATION: GFAP M73K and R79C reverse primer

<400> SEQUENCE: 5
gacacaggct cagaataggt ga                                            22

<210> SEQ ID NO 6
<211> LENGTH: 21
<212> TYPE: DNA
<213> ORGANISM: Artificial Sequence
<220> FEATURE:
<223> OTHER INFORMATION: GFAP R239C forward primer

<400> SEQUENCE: 6
cagagaagct gagactgaga g                                             21

<210> SEQ ID NO 7
<211> LENGTH: 21
<212> TYPE: DNA
<213> ORGANISM: Artificial Sequence
<220> FEATURE:
<223> OTHER INFORMATION: GFAP R239C reverse primer

<400> SEQUENCE: 7
gagagagaca ctcagagaga g                                             21

<210> SEQ ID NO 8
<211> LENGTH: 20
<212> TYPE: DNA
```

```
<213> ORGANISM: Artificial Sequence
<220> FEATURE:
<223> OTHER INFORMATION: CHI3L1 forward primer

<400> SEQUENCE: 8
gtgaaggcgt ctcaaacagg                                                    20

<210> SEQ ID NO 9
<211> LENGTH: 20
<212> TYPE: DNA
<213> ORGANISM: Artificial Sequence
<220> FEATURE:
<223> OTHER INFORMATION: CHI3L1 reverse primer

<400> SEQUENCE: 9
ggtcaagggc atctgggaag                                                    20

<210> SEQ ID NO 10
<211> LENGTH: 20
<212> TYPE: DNA
<213> ORGANISM: Artificial Sequence
<220> FEATURE:
<223> OTHER INFORMATION: CRTH2 forward primer

<400> SEQUENCE: 10
ggtcaccacc tgggtgctgc                                                    20

<210> SEQ ID NO 11
<211> LENGTH: 19
<212> TYPE: DNA
<213> ORGANISM: Artificial Sequence
<220> FEATURE:
<223> OTHER INFORMATION: CRTH2 reverse primer

<400> SEQUENCE: 11
gctgggcacc accttctgc                                                     19

<210> SEQ ID NO 12
<211> LENGTH: 20
<212> TYPE: DNA
<213> ORGANISM: Artificial Sequence
<220> FEATURE:
<223> OTHER INFORMATION: ITGB4 forward primer

<400> SEQUENCE: 12
ccgatgatct ggacaacctc                                                    20

<210> SEQ ID NO 13
<211> LENGTH: 19
<212> TYPE: DNA
<213> ORGANISM: Artificial Sequence
<220> FEATURE:
<223> OTHER INFORMATION: ITGB4 reverse primer

<400> SEQUENCE: 13
gcttctcagg cctcatgtc                                                     19

<210> SEQ ID NO 14
<211> LENGTH: 20
<212> TYPE: DNA
<213> ORGANISM: Artificial Sequence
<220> FEATURE:
<223> OTHER INFORMATION: MBP forward primer

<400> SEQUENCE: 14
ctataaatcg gctcacaagg                                                    20
```

```
<210> SEQ ID NO 15
<211> LENGTH: 20
<212> TYPE: DNA
<213> ORGANISM: Artificial Sequence
<220> FEATURE:
<223> OTHER INFORMATION: MBP reverse primer

<400> SEQUENCE: 15
aggcggttat attaagaagc                                               20

<210> SEQ ID NO 16
<211> LENGTH: 23
<212> TYPE: DNA
<213> ORGANISM: Artificial Sequence
<220> FEATURE:
<223> OTHER INFORMATION: PDGFRA forward primer

<400> SEQUENCE: 16
aagaagtcca ggtgaggtta gag                                           23

<210> SEQ ID NO 17
<211> LENGTH: 19
<212> TYPE: DNA
<213> ORGANISM: Artificial Sequence
<220> FEATURE:
<223> OTHER INFORMATION: PDGFRA reverse primer

<400> SEQUENCE: 17
ggctgcttta ggtgggttt                                                19

<210> SEQ ID NO 18
<211> LENGTH: 20
<212> TYPE: DNA
<213> ORGANISM: Artificial Sequence
<220> FEATURE:
<223> OTHER INFORMATION: ITGB3 forward primer

<400> SEQUENCE: 18
aggtcactca agtcagtccc                                               20

<210> SEQ ID NO 19
<211> LENGTH: 20
<212> TYPE: DNA
<213> ORGANISM: Artificial Sequence
<220> FEATURE:
<223> OTHER INFORMATION: ITGB3 reverse primer

<400> SEQUENCE: 19
cggccagatg attcgaagaa                                               20

<210> SEQ ID NO 20
<211> LENGTH: 20
<212> TYPE: DNA
<213> ORGANISM: Artificial Sequence
<220> FEATURE:
<223> OTHER INFORMATION: TF forward primer

<400> SEQUENCE: 20
aagcctccta ccttgattgc                                               20

<210> SEQ ID NO 21
<211> LENGTH: 20
<212> TYPE: DNA
<213> ORGANISM: Artificial Sequence
<220> FEATURE:
```

<223> OTHER INFORMATION: TF reverse primer

<400> SEQUENCE: 21
ccaccacagg cttcaggtta            20

<210> SEQ ID NO 22
<211> LENGTH: 19
<212> TYPE: DNA
<213> ORGANISM: Artificial Sequence
<220> FEATURE:
<223> OTHER INFORMATION: GAPDH forward primer

<400> SEQUENCE: 22
agccacatcg ctcagacac             19

<210> SEQ ID NO 23
<211> LENGTH: 19
<212> TYPE: DNA
<213> ORGANISM: Artificial Sequence
<220> FEATURE:
<223> OTHER INFORMATION: GAPDH reverse primer

<400> SEQUENCE: 23
gcccaatacg accaaatcc             19

<210> SEQ ID NO 24
<211> LENGTH: 20
<212> TYPE: DNA
<213> ORGANISM: Artificial Sequence
<220> FEATURE:
<223> OTHER INFORMATION: ACTIN forward primer

<400> SEQUENCE: 24
ccgagcgtgg ctacagcttc            20

<210> SEQ ID NO 25
<211> LENGTH: 20
<212> TYPE: DNA
<213> ORGANISM: Artificial Sequence
<220> FEATURE:
<223> OTHER INFORMATION: ACTIN reverse primer

<400> SEQUENCE: 25
acctggccgt caggcagctc            20

<210> SEQ ID NO 26
<211> LENGTH: 23
<212> TYPE: DNA
<213> ORGANISM: Artificial Sequence
<220> FEATURE:
<223> OTHER INFORMATION: sgRNA3

<400> SEQUENCE: 26
catcatctct gcccgctcac tgg         23

<210> SEQ ID NO 27
<211> LENGTH: 23
<212> TYPE: DNA
<213> ORGANISM: Artificial Sequence
<220> FEATURE:
<223> OTHER INFORMATION: sgRNA3

<400> SEQUENCE: 27
tatcaactcc gcccgctcac agg         23

```
<210> SEQ ID NO 28
<211> LENGTH: 19
<212> TYPE: DNA
<213> ORGANISM: Artificial Sequence
<220> FEATURE:
<223> OTHER INFORMATION: forward primer

<400> SEQUENCE: 28
gtgggtgacg gcaagtacg                                              19

<210> SEQ ID NO 29
<211> LENGTH: 19
<212> TYPE: DNA
<213> ORGANISM: Artificial Sequence
<220> FEATURE:
<223> OTHER INFORMATION: reverse primer

<400> SEQUENCE: 29
tggtggagaa gaaggggct                                              19

<210> SEQ ID NO 30
<211> LENGTH: 23
<212> TYPE: DNA
<213> ORGANISM: Artificial Sequence
<220> FEATURE:
<223> OTHER INFORMATION: sgRNA3

<400> SEQUENCE: 30
caccatcact gcctgctcac tgg                                         23

<210> SEQ ID NO 31
<211> LENGTH: 22
<212> TYPE: DNA
<213> ORGANISM: Artificial Sequence
<220> FEATURE:
<223> OTHER INFORMATION: forward primer

<400> SEQUENCE: 31
cccacttctc acaaaacact gc                                          22

<210> SEQ ID NO 32
<211> LENGTH: 22
<212> TYPE: DNA
<213> ORGANISM: Artificial Sequence
<220> FEATURE:
<223> OTHER INFORMATION: reverse primer

<400> SEQUENCE: 32
cttggtggag gaatttgagc tg                                          22

<210> SEQ ID NO 33
<211> LENGTH: 23
<212> TYPE: DNA
<213> ORGANISM: Artificial Sequence
<220> FEATURE:
<223> OTHER INFORMATION: sgRNA3

<400> SEQUENCE: 33
cagcatctct ccccactcac agg                                         23

<210> SEQ ID NO 34
<211> LENGTH: 21
<212> TYPE: DNA
<213> ORGANISM: Artificial Sequence
<220> FEATURE:
<223> OTHER INFORMATION: forward primer
```

```
<400> SEQUENCE: 34
tgtgtcccta gaagcagagg a                                          21

<210> SEQ ID NO 35
<211> LENGTH: 20
<212> TYPE: DNA
<213> ORGANISM: Artificial Sequence
<220> FEATURE:
<223> OTHER INFORMATION: reverse primer

<400> SEQUENCE: 35
atatgccccc gtgtgtttcc                                            20

<210> SEQ ID NO 36
<211> LENGTH: 23
<212> TYPE: DNA
<213> ORGANISM: Artificial Sequence
<220> FEATURE:
<223> OTHER INFORMATION: sgRNA3

<400> SEQUENCE: 36
cttcatctct gtcctctcac agg                                        23

<210> SEQ ID NO 37
<211> LENGTH: 21
<212> TYPE: DNA
<213> ORGANISM: Artificial Sequence
<220> FEATURE:
<223> OTHER INFORMATION: forward primer

<400> SEQUENCE: 37
atgcatttgt cagttcaccc c                                          21

<210> SEQ ID NO 38
<211> LENGTH: 21
<212> TYPE: DNA
<213> ORGANISM: Artificial Sequence
<220> FEATURE:
<223> OTHER INFORMATION: reverse primer

<400> SEQUENCE: 38
taacctttgc agaggctcgt c                                          21

<210> SEQ ID NO 39
<211> LENGTH: 23
<212> TYPE: DNA
<213> ORGANISM: Artificial Sequence
<220> FEATURE:
<223> OTHER INFORMATION: sgRNA3

<400> SEQUENCE: 39
cctcatctct gccagcacac ggg                                        23

<210> SEQ ID NO 40
<211> LENGTH: 20
<212> TYPE: DNA
<213> ORGANISM: Artificial Sequence
<220> FEATURE:
<223> OTHER INFORMATION: forward primer

<400> SEQUENCE: 40
ggcagggcag gatataaggc                                            20

<210> SEQ ID NO 41
<211> LENGTH: 20
```

```
<212> TYPE: DNA
<213> ORGANISM: Artificial Sequence
<220> FEATURE:
<223> OTHER INFORMATION: reverse primer

<400> SEQUENCE: 41
gctctccgtc tctaagtggg                                        20

<210> SEQ ID NO 42
<211> LENGTH: 23
<212> TYPE: DNA
<213> ORGANISM: Artificial Sequence
<220> FEATURE:
<223> OTHER INFORMATION: sgRNA3

<400> SEQUENCE: 42
catcatcact gcccccacac tgg                                    23

<210> SEQ ID NO 43
<211> LENGTH: 21
<212> TYPE: DNA
<213> ORGANISM: Artificial Sequence
<220> FEATURE:
<223> OTHER INFORMATION: forward primer

<400> SEQUENCE: 43
aaggaatgca gatgggctca a                                      21

<210> SEQ ID NO 44
<211> LENGTH: 21
<212> TYPE: DNA
<213> ORGANISM: Artificial Sequence
<220> FEATURE:
<223> OTHER INFORMATION: reverse primer

<400> SEQUENCE: 44
aacaaccatc caactgctcc t                                      21

<210> SEQ ID NO 45
<211> LENGTH: 23
<212> TYPE: DNA
<213> ORGANISM: Artificial Sequence
<220> FEATURE:
<223> OTHER INFORMATION: sgRNA3

<400> SEQUENCE: 45
cctcatctct gctcgctctc tgg                                    23

<210> SEQ ID NO 46
<211> LENGTH: 21
<212> TYPE: DNA
<213> ORGANISM: Artificial Sequence
<220> FEATURE:
<223> OTHER INFORMATION: forward primer

<400> SEQUENCE: 46
cgtgggaaat ggtcaagaac g                                      21

<210> SEQ ID NO 47
<211> LENGTH: 20
<212> TYPE: DNA
<213> ORGANISM: Artificial Sequence
<220> FEATURE:
<223> OTHER INFORMATION: reverse primer

<400> SEQUENCE: 47
```

```
gcttagactc acccacaggt                                                20
```

<210> SEQ ID NO 48
<211> LENGTH: 23
<212> TYPE: DNA
<213> ORGANISM: Artificial Sequence
<220> FEATURE:
<223> OTHER INFORMATION: sgRNA3

<400> SEQUENCE: 48

```
catcttctct gcccgctcta ggg                                            23
```

<210> SEQ ID NO 49
<211> LENGTH: 20
<212> TYPE: DNA
<213> ORGANISM: Artificial Sequence
<220> FEATURE:
<223> OTHER INFORMATION: forward primer

<400> SEQUENCE: 49

```
agcttctccg aggtccatct                                                20
```

<210> SEQ ID NO 50
<211> LENGTH: 20
<212> TYPE: DNA
<213> ORGANISM: Artificial Sequence
<220> FEATURE:
<223> OTHER INFORMATION: reverse primer

<400> SEQUENCE: 50

```
ccagcttcac cctaacccag                                                20
```

<210> SEQ ID NO 51
<211> LENGTH: 23
<212> TYPE: DNA
<213> ORGANISM: Artificial Sequence
<220> FEATURE:
<223> OTHER INFORMATION: sgRNA4

<400> SEQUENCE: 51

```
ctttgccagc tacatcgaga agg                                            23
```

<210> SEQ ID NO 52
<211> LENGTH: 23
<212> TYPE: DNA
<213> ORGANISM: Artificial Sequence
<220> FEATURE:
<223> OTHER INFORMATION: sgRNA4

<400> SEQUENCE: 52

```
cttcgccaac tacatcgaga agg                                            23
```

<210> SEQ ID NO 53
<211> LENGTH: 21
<212> TYPE: DNA
<213> ORGANISM: Artificial Sequence
<220> FEATURE:
<223> OTHER INFORMATION: forward primer

<400> SEQUENCE: 53

```
cggtgaacca ggagtttctg a                                              21
```

<210> SEQ ID NO 54
<211> LENGTH: 21
<212> TYPE: DNA
<213> ORGANISM: Artificial Sequence

```
<220> FEATURE:
<223> OTHER INFORMATION: reverse primer

<400> SEQUENCE: 54
ctggttagtg agcacctcca c                                              21

<210> SEQ ID NO 55
<211> LENGTH: 23
<212> TYPE: DNA
<213> ORGANISM: Artificial Sequence
<220> FEATURE:
<223> OTHER INFORMATION: sgRNA4

<400> SEQUENCE: 55
ctttgccggc tacatagaga agg                                            23

<210> SEQ ID NO 56
<211> LENGTH: 20
<212> TYPE: DNA
<213> ORGANISM: Artificial Sequence
<220> FEATURE:
<223> OTHER INFORMATION: forward primer

<400> SEQUENCE: 56
tcctcctata agcgcagcat                                                20

<210> SEQ ID NO 57
<211> LENGTH: 20
<212> TYPE: DNA
<213> ORGANISM: Artificial Sequence
<220> FEATURE:
<223> OTHER INFORMATION: reverse primer

<400> SEQUENCE: 57
ctggatctcc gcctcaatct                                                20

<210> SEQ ID NO 58
<211> LENGTH: 23
<212> TYPE: DNA
<213> ORGANISM: Artificial Sequence
<220> FEATURE:
<223> OTHER INFORMATION: sgRNA4

<400> SEQUENCE: 58
ctttgccagc tacatcggaa ggg                                            23

<210> SEQ ID NO 59
<211> LENGTH: 20
<212> TYPE: DNA
<213> ORGANISM: Artificial Sequence
<220> FEATURE:
<223> OTHER INFORMATION: forward primer

<400> SEQUENCE: 59
ttctgggagg agaggcagaa                                                20

<210> SEQ ID NO 60
<211> LENGTH: 20
<212> TYPE: DNA
<213> ORGANISM: Artificial Sequence
<220> FEATURE:
<223> OTHER INFORMATION: reverse primer

<400> SEQUENCE: 60
tcctactctg tctgccccaa                                                20
```

<210> SEQ ID NO 61
<211> LENGTH: 23
<212> TYPE: DNA
<213> ORGANISM: Artificial Sequence
<220> FEATURE:
<223> OTHER INFORMATION: sgRNA4

<400> SEQUENCE: 61
ctttgctatg tacatcgaga tgg                                          23

<210> SEQ ID NO 62
<211> LENGTH: 21
<212> TYPE: DNA
<213> ORGANISM: Artificial Sequence
<220> FEATURE:
<223> OTHER INFORMATION: forward primer

<400> SEQUENCE: 62
tgggtgggca gatttcccta a                                            21

<210> SEQ ID NO 63
<211> LENGTH: 21
<212> TYPE: DNA
<213> ORGANISM: Artificial Sequence
<220> FEATURE:
<223> OTHER INFORMATION: reverse primer

<400> SEQUENCE: 63
cagcattacc ctgtgtccgt t                                            21

<210> SEQ ID NO 64
<211> LENGTH: 23
<212> TYPE: DNA
<213> ORGANISM: Artificial Sequence
<220> FEATURE:
<223> OTHER INFORMATION: sgRNA4

<400> SEQUENCE: 64
cttcgccaac ttcatcgaga agg                                          23

<210> SEQ ID NO 65
<211> LENGTH: 20
<212> TYPE: DNA
<213> ORGANISM: Artificial Sequence
<220> FEATURE:
<223> OTHER INFORMATION: forward primer

<400> SEQUENCE: 65
ccacctcata ccgccgtacc                                              20

<210> SEQ ID NO 66
<211> LENGTH: 20
<212> TYPE: DNA
<213> ORGANISM: Artificial Sequence
<220> FEATURE:
<223> OTHER INFORMATION: reverse primer

<400> SEQUENCE: 66
gttctgctgc tccagaaagc                                              20

<210> SEQ ID NO 67
<211> LENGTH: 23
<212> TYPE: DNA
<213> ORGANISM: Artificial Sequence
<220> FEATURE:
<223> OTHER INFORMATION: sgRNA4

```
<400> SEQUENCE: 67
cttttcctgc tatatcgaga tgg                                           23

<210> SEQ ID NO 68
<211> LENGTH: 20
<212> TYPE: DNA
<213> ORGANISM: Artificial Sequence
<220> FEATURE:
<223> OTHER INFORMATION: forward primer

<400> SEQUENCE: 68
gaagacactc agccaaggca                                               20

<210> SEQ ID NO 69
<211> LENGTH: 21
<212> TYPE: DNA
<213> ORGANISM: Artificial Sequence
<220> FEATURE:
<223> OTHER INFORMATION: reverse primer

<400> SEQUENCE: 69
acccgaagga gttgttcaga g                                             21

<210> SEQ ID NO 70
<211> LENGTH: 23
<212> TYPE: DNA
<213> ORGANISM: Artificial Sequence
<220> FEATURE:
<223> OTHER INFORMATION: sgRNA4

<400> SEQUENCE: 70
attagccagc tacatggaga agg                                           23

<210> SEQ ID NO 71
<211> LENGTH: 24
<212> TYPE: DNA
<213> ORGANISM: Artificial Sequence
<220> FEATURE:
<223> OTHER INFORMATION: forward primer

<400> SEQUENCE: 71
tgtctgctca tacgttgcac atta                                          24

<210> SEQ ID NO 72
<211> LENGTH: 22
<212> TYPE: DNA
<213> ORGANISM: Artificial Sequence
<220> FEATURE:
<223> OTHER INFORMATION: reverse primer

<400> SEQUENCE: 72
ggcacagaga agtcagctag ta                                            22

<210> SEQ ID NO 73
<211> LENGTH: 23
<212> TYPE: DNA
<213> ORGANISM: Artificial Sequence
<220> FEATURE:
<223> OTHER INFORMATION: sgRNA4

<400> SEQUENCE: 73
cttttccagc tacactgaga agg                                           23

<210> SEQ ID NO 74
```

```
<211> LENGTH: 20
<212> TYPE: DNA
<213> ORGANISM: Artificial Sequence
<220> FEATURE:
<223> OTHER INFORMATION: forward primer

<400> SEQUENCE: 74
agaatgtgcc tgcccaagtt                                               20

<210> SEQ ID NO 75
<211> LENGTH: 20
<212> TYPE: DNA
<213> ORGANISM: Artificial Sequence
<220> FEATURE:
<223> OTHER INFORMATION: reverse primer

<400> SEQUENCE: 75
gggcagtcgt caaagtcaga                                               20

<210> SEQ ID NO 76
<211> LENGTH: 23
<212> TYPE: DNA
<213> ORGANISM: Artificial Sequence
<220> FEATURE:
<223> OTHER INFORMATION: sgRNA4

<400> SEQUENCE: 76
ctttcccagc tacataaaga ggg                                           23

<210> SEQ ID NO 77
<211> LENGTH: 20
<212> TYPE: DNA
<213> ORGANISM: Artificial Sequence
<220> FEATURE:
<223> OTHER INFORMATION: forward primer

<400> SEQUENCE: 77
aaaagtcagg ggcgttgtct                                               20

<210> SEQ ID NO 78
<211> LENGTH: 20
<212> TYPE: DNA
<213> ORGANISM: Artificial Sequence
<220> FEATURE:
<223> OTHER INFORMATION: reverse primer

<400> SEQUENCE: 78
cctgcagagt aagccctagc                                               20

<210> SEQ ID NO 79
<211> LENGTH: 23
<212> TYPE: DNA
<213> ORGANISM: Artificial Sequence
<220> FEATURE:
<223> OTHER INFORMATION: sgRNA4

<400> SEQUENCE: 79
ctttgcgggc tacatcgaca agg                                           23

<210> SEQ ID NO 80
<211> LENGTH: 19
<212> TYPE: DNA
<213> ORGANISM: Artificial Sequence
<220> FEATURE:
<223> OTHER INFORMATION: forward primer

<400> SEQUENCE: 80
```
cgatgtcctc gagcaggtg                                                19

<210> SEQ ID NO 81
<211> LENGTH: 20
<212> TYPE: DNA
<213> ORGANISM: Artificial Sequence
<220> FEATURE:
<223> OTHER INFORMATION: reverse primer

<400> SEQUENCE: 81
tgctacaacg agcagtgagg                                               20

<210> SEQ ID NO 82
<211> LENGTH: 23
<212> TYPE: DNA
<213> ORGANISM: Artificial Sequence
<220> FEATURE:
<223> OTHER INFORMATION: sgRNA4

<400> SEQUENCE: 82
cttcgccaac tacatcgaca agg                                           23

<210> SEQ ID NO 83
<211> LENGTH: 18
<212> TYPE: DNA
<213> ORGANISM: Artificial Sequence
<220> FEATURE:
<223> OTHER INFORMATION: forward primer

<400> SEQUENCE: 83
cgtgactacg tccacccg                                                 18

<210> SEQ ID NO 84
<211> LENGTH: 21
<212> TYPE: DNA
<213> ORGANISM: Artificial Sequence
<220> FEATURE:
<223> OTHER INFORMATION: reverse primer

<400> SEQUENCE: 84
ctcggccagc aggatcttat t                                             21

<210> SEQ ID NO 85
<211> LENGTH: 19
<212> TYPE: DNA
<213> ORGANISM: Artificial Sequence
<220> FEATURE:
<223> OTHER INFORMATION: control shRNA

<400> SEQUENCE: 85
tctactgtca ctcagtacc                                                19

<210> SEQ ID NO 86
<211> LENGTH: 20
<212> TYPE: DNA
<213> ORGANISM: Artificial Sequence
<220> FEATURE:
<223> OTHER INFORMATION: CHI3L1 shRNA-1

<400> SEQUENCE: 86
atgcagagca gcactggagc                                               20

<210> SEQ ID NO 87
<211> LENGTH: 20
<212> TYPE: DNA

```
<213> ORGANISM: Artificial Sequence
<220> FEATURE:
<223> OTHER INFORMATION: CHI3L1 shRNA-2

<400> SEQUENCE: 87
atggcggtac tgacttgatg                                               20

<210> SEQ ID NO 88
<211> LENGTH: 10
<212> TYPE: DNA
<213> ORGANISM: Artificial Sequence
<220> FEATURE:
<223> OTHER INFORMATION: GFAP mutation

<400> SEQUENCE: 88
gtgcgagatc                                                          10

<210> SEQ ID NO 89
<211> LENGTH: 10
<212> TYPE: DNA
<213> ORGANISM: Artificial Sequence
<220> FEATURE:
<223> OTHER INFORMATION: GFAP mutation

<400> SEQUENCE: 89
tgacctgctt                                                          10

<210> SEQ ID NO 90
<211> LENGTH: 10
<212> TYPE: DNA
<213> ORGANISM: Artificial Sequence
<220> FEATURE:
<223> OTHER INFORMATION: GFAP mutation

<400> SEQUENCE: 90
gagaatgatg                                                          10

<210> SEQ ID NO 91
<211> LENGTH: 10
<212> TYPE: DNA
<213> ORGANISM: Artificial Sequence
<220> FEATURE:
<223> OTHER INFORMATION: WT ssODN

<400> SEQUENCE: 91
agagatgatg                                                          10

<210> SEQ ID NO 92
<211> LENGTH: 9
<212> TYPE: DNA
<213> ORGANISM: Artificial Sequence
<220> FEATURE:
<223> OTHER INFORMATION: GFAP mutation (M73K)

<400> SEQUENCE: 92 gagatgatg                                                            9
```

DETECTION AND TREATMENT OF NEUROLOGICAL DISEASES

PRIORITY CLAIM

This application claims priority to U.S. Provisional Patent Application No. 62/713,475, filed Aug. 1, 2018, which is incorporated herein by reference.

STATEMENT OF GOVERNMENT INTEREST

The present invention was made with government support under Grant Nos. RB4-06277 and TRAN1-08525, awarded by the California Institute for Regenerative Medicine. The Government has certain rights in the invention.

SEQUENCE LISTING

This application contains a sequence listing, which was submitted in ASCII format via EFS-Web, and is hereby incorporated by reference in its entirety. The ASCII copy, created on Sep. 6, 2019, is named 8188 US01_SequenceListing.txt and is 17.2 KB in size.

BACKGROUND

Astrocytes play important roles in maintaining brain homeostasis and function. Astrocyte dysfunction is involved in the pathogenesis of a wide variety of neurological diseases, including Alzheimer, Parkinson, Huntington disease, multiple sclerosis and amyotrophic lateral sclerosis (Rempe and Nedergaard, 2010). However, the specific effects of astrocyte dysfunction on neurodegeneration cannot be easily dissected by studying these diseases because they are complex conditions that also involve dysfunctions of other cell types, including neurons, oligodendrocytes and immune cells (Messing et al., 2012). Therefore, there is a need in the art to identify astrocyte dysfunction, thereby to employ effective treatments that can restore astrocyte functions.

SUMMARY

In one aspect, this disclosure relates to a method of detecting the abnormal expression of one or more genes associated with a neurological disease. The method comprises the steps of differentiating astrocytes from induced pluripotent stem cells (iPSCs) obtained from one or more healthy control subjects; differentiating astrocytes from iPSCs obtained from a subject suffering from a neurological disease; performing a transcriptome analysis of the astrocytes derived from the subject suffering from the neurological disease and a transcriptome analysis of the astrocytes derived from the one or more healthy control subjects; comparing the results of both transcriptome analyses to identify one or more genes that are substantially differentially expressed in the subject suffering from the neurological disease comparing to the one or more healthy subjects; and correcting the expression of the one or more substantially differentially expressed genes, wherein complete or partial restoring of one or more phenotypes of the neurological disease after gene expression correction indicates that the one or more substantially differentially expressed genes are associated with the neurological disease. In some embodiments, one or more genes are up-regulated in the subject suffering from the neurological disease and the abnormal gene expression is corrected by administering an effective amount of an inhibitor of the up-regulated gene to the subject. Examples of such inhibitors include RNAi, e.g., siRNA and shRNA targeting the upregulated gene, CRISPR/Cas9-mediated inhibition (CRISPRi), CRISPR/Cas9-mediated gene knockout, neutralizing antibodies, or small molecule compounds that inhibit the expression of the up-regulated genes. In other embodiments, one or more genes are down-regulated in the subject suffering from the neurological disease and the abnormal gene expression is corrected by CRISPR/Cas9-mediated activation (CRISPRa) or small molecule compounds that activate the expression of the down-regulated genes. In some embodiments, the neurological disease is associated with astrocyte abnormalities. In some embodiments, the neurological disease includes the Alexander disease, the Alzheimer's disease, the Parkinson disease, the Huntington disease, multiple sclerosis, and amyotrophic lateral sclerosis.

In another aspect, this disclosure relates to a method of detecting the abnormal expression of one or more genes associated with a neurological disease other than Alexander disease using astrocytes derived from one or more subjects suffering from the Alexander disease. The method comprises the steps of differentiating astrocytes from iPSCs obtained from one or more healthy control subjects; differentiating astrocytes from iPSCs obtained from one or more subjects suffering from the Alexander disease; performing a transcriptome analysis of the astrocytes derived from the one or more subjects suffering from the Alexander disease and a transcriptome analysis of the astrocytes derived from the one or more healthy control subjects; comparing the results of both transcriptome analyses to identify one or more genes that are substantially differentially expressed in the one or more subjects suffering from the Alexander disease comparing to the one or more healthy subjects; categorizing the one or more substantially differentially expressed genes to determine whether a particular gene affects the mechanism of a neurological disease that is not the Alexander disease, and/or validating the abnormal expression of the one or more genes substantially differentially expressed genes in a subject suffering from a neurological disease that is not the Alexander disease. If the particular gene is determined to affect the mechanism of the neurological disease other than the Alexander disease, then that particular gene is associated with the neurological disease other than the Alexander disease and can be used as a potential treatment target for the neurological disease other than the Alexander disease. Likewise, if the abnormal expression of the particular gene is validated in a subject suffering from the neurological disease other than the Alexander disease, then that particular gene is associated with the neurological disease other than the Alexander disease and can be used as a potential treatment target for the neurological disease other than the Alexander disease. In some embodiments, the neurological disease that is not the Alexander disease is associated with astrocyte abnormalities. In some embodiments, the neurological disease that is not the Alexander disease is selected from the group consisting of the Alzheimer's disease, the Parkinson disease, the Huntington disease, multiple sclerosis, and amyotrophic lateral sclerosis. In some embodiments, the method further comprises, before the step of categorizing the one or more substantially differentially expressed genes, a step of completely or partially restoring one or more phenotypes of the Alexander disease by correcting the expression of the one or more substantially differentially expressed genes. In some embodiments, one or more genes are up-regulated in the subject suffering from the Alexander disease and the abnormal gene expression is corrected by administering an effective amount of an inhibitor of the up-regulated gene to the subject. Examples of such inhibitors include RNAi, e.g., siRNA and shRNA targeting the upregulated gene, CRISPR/Cas9-mediated inhibition (CRISPRi), CRISPR/Cas9-mediated gene knockout, neutralizing antibodies, or small molecule compounds that inhibit the expression of the up-regulated genes. In other embodiments, one or more genes are down-regulated in the subject suffering from the Alexander disease and the abnormal gene expression is corrected by CRISPR/Cas9-mediated activation (CRISPRa) or small molecule compounds that activate the expression of the down-regulated genes.

In another aspect, provided herein is a method of treating a neurological disease. The method comprises detecting the abnormal expression of one or more genes associated with a neurological disease using either of the methods described above, and correcting the abnormal expression of the one or more genes such that one or more phenotypes of the neurological disease are completely or partially restored. In some embodiments, one or more genes are up-regulated in the subject suffering from the neurological disease and the abnormal gene expression is corrected by administering an effective amount of an inhibitor of the up-regulated gene to the subject. Examples of such inhibitors include RNAi, e.g., siRNA and shRNA targeting the upregulated gene, CRISPR/Cas9-mediated inhibition (CRISPRi), CRISPR/Cas9-mediated gene knockout, neutralizing antibodies, or small molecule compounds that inhibit the expression of the up-regulated genes. In other embodiments, one or more genes are down-regulated in the subject suffering from the neurological disease and the abnormal gene expression is corrected by CRISPR/Cas9-mediated activation (CRISPRa) or small molecule compounds that activate the expression of the down-regulated genes. In some embodiments, the neurological disease is associated with astrocyte abnormalities. In some embodiments, the neurological disease includes the Alexander disease, the Alzheimer's disease, the Parkinson disease, the Huntington disease, multiple sclerosis, and amyotrophic lateral sclerosis.

In another aspect, provided herein is a method of treating a neurological disease in a subject comprising administering an effective amount of an inhibitor of CHI3L1 or an inhibitor of a CHI3L1 receptor to the subject. In some embodiments, the CHI3L1 receptor is CRTH2. In some embodiments, the inhibitor of CHI3L1 is an RNAi such as shRNA and siRNA targeting CHI3L1 or an anti-CHI3L1 antibody. In some embodiments, the inhibitor of a CHI3L1 receptor is an RNAi such as shRNA and siRNA targeting the CHI3L1 receptor or an anti-CHI3L1 receptor antibody. In some embodiments, the neurological disease is associated with astrocyte abnormalities. In some embodiments, the neurological disease includes the Alexander disease, the Alzheimer's disease, the Parkinson disease, the Huntington disease, multiple sclerosis, and amyotrophic lateral sclerosis.

In yet another aspect, provided herein is a pharmaceutical composition for treating a neurological disease. The pharmaceutical composition comprising an effective amount of an inhibitor of CHI3L1 or an inhibitor of a CHI3L1 receptor. The pharmaceutical composition can further comprise one or more pharmaceutically acceptable carrier. In some embodiments, the CHI3L1 receptor is CRTH2. In some embodiments, the inhibitor of CHI3L1 is an RNAi such as shRNA and siRNA targeting CHI3L1 or an anti-CHI3L1 antibody. In some embodiments, the inhibitor of a CHI3L1 receptor is an RNAi such as shRNA and siRNA targeting the CHI3L1 receptor or an anti-CHI3L1 receptor antibody. In some embodiments, the neurological disease is associated with astrocyte abnormalities. In some embodiments, the neurological disease includes the Alexander disease, the Alzheimer's disease, the Parkinson disease, the Huntington disease, multiple sclerosis, and amyotrophic lateral sclerosis.

In another aspect, provided herein is a method of detecting a neurological disease using patient-derived astrocytes. The method comprises differentiating human iPSCs obtained from a patient suffering from a neurological disease into astrocytes in an efficient and reproducible manner, wherein the human iPSCs and the derived astrocytes from the patient retain the gene mutations causing the neurological disease. This method can be used to generate astrocytes from iPSCs of a variety of neurological diseases, including Alzheimer's disease, Parkinson disease, Huntington disease, multiple sclerosis, and amyotrophic lateral sclerosis. These iPSC-derived astrocytes can be used to identify disease mechanisms, screen drugs, or used as cell therapies.

BRIEF DESCRIPTION OF THE DRAWINGS

This application contains at least one drawing executed in color. Copies of this application with color drawing(s) will be provided by the Office upon request and payment of the necessary fees.

FIGS. 1A-1I show that AxD patient iPSC-derived astrocytes exhibit GFAP aggregates. FIG. 1A shows human iPSC lines used in the study, including 3 control lines, I90, C1 and C3, 3 AxD lines, AxD825, AxD997 and AxD999, and an isogenic line, AxD999-CR, with the GFAP mutation corrected by CRISPR/Cas9 editing. FIG. 1B shows sequencing of GFAP mutations in AxD iPSC lines. FIG. 1C shows schematic for CRISPR/Cas9 targeting of the GFAP mutation (M73K) in AxD999 iPSCs, and sequence confirming the WT genotype of AxD999-CR iPSCs. FIGS. 1D-1F show the percentage of S100 β+(FIG. 1D) and GFAP$^+$ (FIG. 1E) cells, and representative images of GFAP and S100 β staining (FIG. 1F) in iPSC-derived astrocytes. Error bars are SD of the mean, n=3 experimental repeats for FIGS. 1D and 1E. FIG. 1G shows representative images of GFAP aggregates (pointed by arrows) in AxD iPSC-derived astrocytes by immunostaining. The GFAP aggregates were absent in control and AxD999-CR astrocytes. FIG. 1H shows electron microscopy images of filament bundles resembling Rosenthal fibers in AxD997 and AxD999 astrocytes, but not C3 and AxD999-CR astrocytes. n=4 experimental repeats. FIG. 1I shows representative images of GFAP and αB-Crystalline (CRYAB) double staining in AxD997 and AxD999 astrocytes. No αB-Crystalline signal was detected in C3 and AxD999-CR astrocytes. Scale bar 50 μm for FIGS. 1F, 1G & 1I; and 0.5 μm for FIG. 1H.

FIG. 2A shows expression of pluripotency markers in iPSCs by immunostaining. FIG. 2B shows epigenetic reprogramming in iPSCs by bisulfite sequencing of the OCT4 promoter. Open and closed circles indicate unmethylated and methylated CpGs, respectively. FIG. 2C shows the developmental potential of iPSCs by teratoma formation. All three germ layers are present in the teratomas shown by H&E staining. FIG. 2D shows normal karyotype of iPSCs by G-banded karyotyping. FIG. 2E is a surveyor nuclease assay showing sgRNA-guided Cas9 cleavage in cells transfected with sgRNA 4 and Cas9, sgRNA3 and Cas9, or sgRNA 4 and 3 with Cas9 nickase. FIG. 2F shows screening for single cell-derived iPSC clones with the corrected M73 site in the GFAP gene. Clone 38 exhibited expected restriction enzyme digestion pattern of a corrected clone. Scale bar. 100 μm for FIGS. 2A & 2C.

FIGS. 3A-3E show purification and characterization of AxD astrocytes. FIGS. 3A and 3B are immunostaining showing that the GFAP-GFP-positive cells were GFAP-positive in hGFAP-GFP transduced human primary astrocytes (hPrimary astrocytes). Human fibroblasts (hFibroblasts) were included as a negative control. FIG. 3B shows quantification of the percentage of hGFAP-GFP$^+$ GFAP$^+$ cells in total GFAP$^+$ cells in hPrimary astrocytes and hFibroblasts. FIG. 3C shows validation of GFAP and S100 β staining using hPrimary astrocytes as the positive control and hFibroblasts as the negative control. FIG. 3D are dot plots showing sorting of hGFAP-GFP$^+$ cell populations in iPSC-derived astrocytes by FACS. Human iPSC-derived astrocytes were transduced with hGFAP-GFP-encoding lentivirus and subjected to FACS. Astrocytes without hGFAP-GFP lentivirus transduction were used as a control. FIG. 3E shows SOX9 staining in iPSC-derived astrocytes. hPrimary astrocytes were used as the positive control and hFibroblasts as the negative control. Scale bar. 100 μm for FIGS. 3A & 3C, 50 μm for FIG. 3E.

FIG. 4A shows immunostainings of hGFAP-GFP purified astrocytes with the OPC markers O4 and OLIG2, the oligodendrocyte marker MBP, the fibroblast marker FSP, the endothelial cell marker CD31, and the neuronal marker MAP2. Cells were counterstained with DAPI. FIG. 4B shows immunostaining for human-specific GFAP (hGFAP) in mouse brains transplanted with hGFAP-GFP-labeled AxD astrocytes. Scale bar. 100 μm for FIGS. 4A & 4B. FIG. 4C shows calcium imaging of control and AxD astrocytes in response to stimulus by 3 μM ATP. The percentage of control and AxD astrocytes exhibiting calcium response is shown. Error bars are SD of the mean, n=3 experimental repeats. FIG. 4D shows whole-cell patch clamp recording of control and AxD astrocytes. Voltage steps (clamped at −70 mV and stepped from −50 mV to +50 mV at 10 mV increments) induced outward currents in control and AxD astrocytes.

FIGS. 5A-5G show AxD astrocytes hardly induced OPC apoptosis and exhibited minimal variation in astrocyte proliferation. FIG. 5A shows immunostaining of oligodendrocyte (OL) lineage markers during differentiation from iPSCs. Cells were stained for OLIG2 and NKX2.2 on Day 12 of differentiation, for O4 on Day 75 of differentiation, and for MBP after 2 weeks of maturation from OPCs. FIGS. 5B and 5C show double staining OPCs for O4 and MBP (FIG. 5B) or OLIG2 and MBP (FIG. 5C). FIG. 5D shows representative images of cleaved caspase-3 (Cas3) and OLIG2 double staining in OPCs co-cultured with control or AxD astrocytes. FIG. 5E shows the percentage of Cas3$^+$ OLIG2$^+$ cells over total OLIG2$^+$ cells. FIG. 5F shows representative images of BrdU staining (red) of GFAP-GFP-sorted astrocytes (green). FIG. 5G shows the percentage of BrdU$^+$ cells over total GFAP-GFP$^+$ astrocytes. Scale bar 100 μm for OLIG2 and O4 staining images in FIG. 5A & images in FIG. 5D; 50 μm for the MBP staining image in FIG. 5A and images in FIGS. 5B & 5C. Error bars are SD of the mean, n=3 experimental repeats for FIGS. 5E & 5G.

FIGS. 6A-6K show that AxD astrocytes reduced OPC proliferation. FIG. 6A shows schematic of OPC-astrocyte co-culture system. O4-sorted I90 iPSC-derived OPCs were seeded onto GFAP-GFP-sorted control or AxD astrocytes for co-culture. FIGS. 6B and 6E show representative images of O4 live staining (FIG. 6B) and fold change in O4$^+$ cell number (FIG. 6E) after 5-day co-culture of OPCs with control or AxD astrocytes. FIGS. 6C and 6F show representative images of OLIG2 staining (FIG. 6C) and fold change in OLIG2$^+$ cell number (FIG. 6F) after 5-day co-culture. FIGS. 6D and 6G show representative images of BrdU and OLIG2 double staining (FIG. 6D) and the percentage of BrdU$^+$ OLIG2$^+$ cells (FIG. 6E) after 24 hr co-culture. FIGS. 6H and 6I show representative images of O4 live staining (FIG. 6H) and fold change in O4$^+$ cell number (FIG. 6I) after 5-day co-culture of OPCs with AxD999-CR or AxD999 astrocytes. FIGS. 6J and 6K show representative images of BrdU and OLIG2 double staining (FIG. 6J) and the percentage of BrdU$^+$ OLIG2$^+$ cells (FIG. 6K) after 24 hr co-culture of OPCs with AxD999-CR or AxD999 astrocytes. Arrows point to the BrdU$^+$ OLIG2$^+$ cells. Scale bar: 100 μm for FIGS. 6B, 6D, and 6H, 50 μm for FIGS. 6C and 6J. Error bars are SE of the means, n=3 experimental repeats, *p<0.05 by one-way ANOVA for FIGS. 6E-6G, **p<0.01 by Student's t-test for FIGS. 6I and 6K.

FIGS. 7A-7G show that AxD astrocytes caused myelination defect in a 3D nanofiber culture system. FIGS. 7A and 7C show representative images of MBP immunostaining in a 3D nanofiber culture system that included GFAP-GFP-sorted control vs AxD (FIG. 7A), or AxD999-CR vs AxD999 (FIG. 7C) astrocytes (green) and oligodendrocytes matured from I90 hiPSC-derived OPCs. Scale bar: 50 μm. FIGS. 7B and 7D show representative images of MBP immunostaining and alignment with nanofibers in control vs AxD (FIG. 7B), or AxD999-CR vs AxD999 (FIG. 7D) co-cultures. Scale bar: 100 μm. Higher magnification images are shown underneath FIG. 7B to highlight the alignment of the MBP segments with nanofibers. Scale bar: 20 μm. FIGS. 7E-7G show fold change in MBP$^+$ cell number (#) (FIG. 7E), MBP$^+$ area (FIG. 7F), and MBP$^+$ segment length (FIG. 7G) in nanofiber-based co-culture of OPCs with astrocytes. Error bars are SE of the means, n=3 experimental repeats, *p<0.05, p<0.01, and *p<0.001 by one-way ANOVA for FIGS. 7E-7G.

FIG. 8A shows 3D view of MBP$^+$ cells in a nanofiber culture system that included AxD999-CR or AxD999 astrocytes and oligodendrocytes matured from I90 iPSC-derived OPCs. FIG. 8B shows orthogonal images showing XZ sections (vertical arrows) and XY sections (horizontal arrows) of MBP signals wrapping around nanofibers in AxD999-CR and AxD999 co-cultures. 3D view of the corresponding cells was shown underneath the orthogonal images.

Figure 9A:
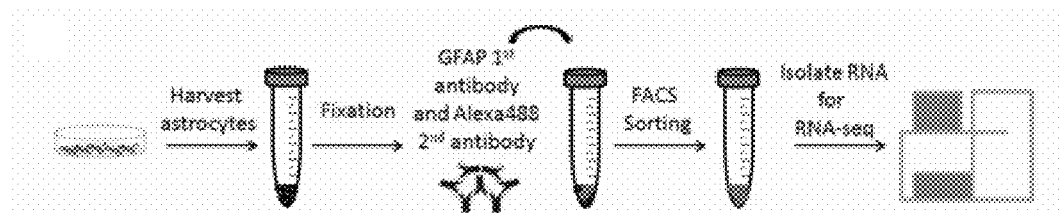
FIGS. 9A-9G show that transcriptome analysis revealed difference between AxD and healthy control astrocytes.
Figure 9B:
Figure 9C:
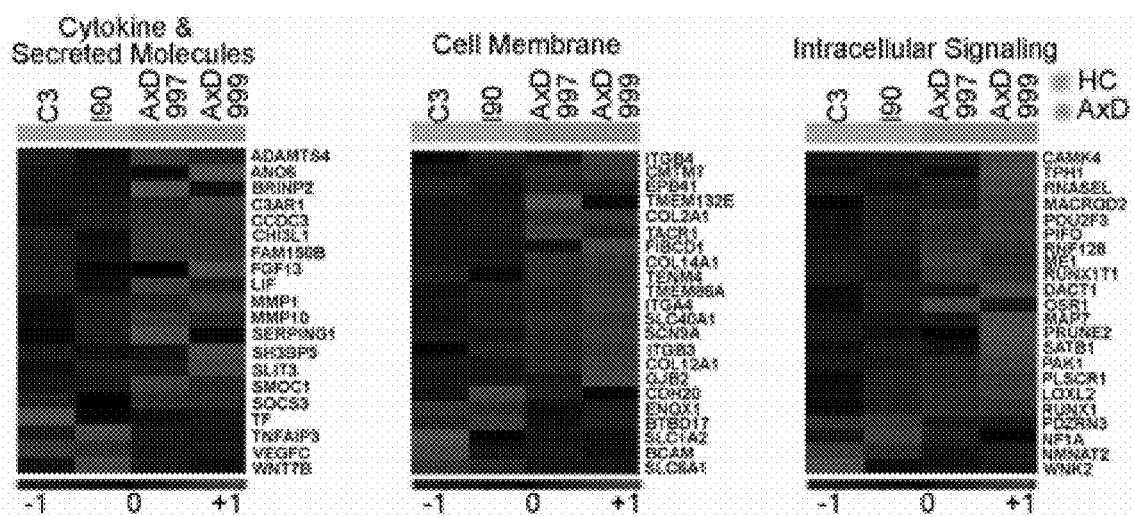
Figure 9D:
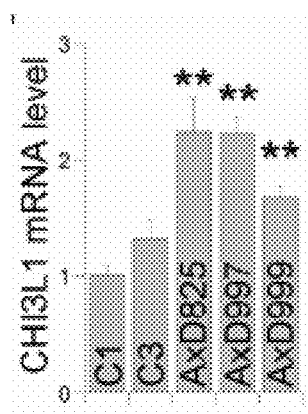
Figure 9E:
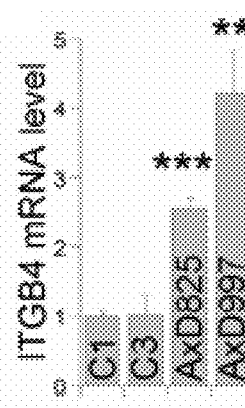
Figure 9F:
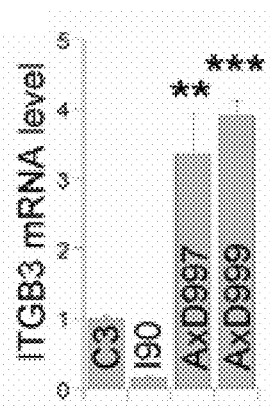
Figure 9G:
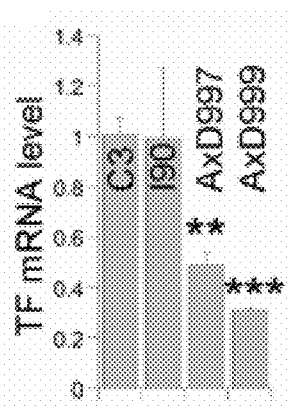

FIG. 9A shows schematic of RNA isolation from GFAP-purified astrocytes. Astrocytes were stained with GFAP antibody and the GFAP$^+$ cells were sorted by FACS, followed by RNA isolation. FIG. 9B shows GO terms of genes up-regulated (red) or down-regulated (blue) in AxD997 and AxD999 astrocytes, compared to C3 and I90 control astrocytes. X axis is enrichment score calculated as −log (P value). Full names of abbreviated GO terms are: negative regulation of cell proliferation (cell proliferation); intrinsic component of membrane (cell membrane); nervous system development (nervous system dev). FIG. 9C shows heatmap presentation of 3 categories of representative gene sets up-regulated (red) or down-regulated (blue) in AxD astrocytes compared to control astrocytes, including genes encoding cytokines and secreted molecules, cell membrane proteins, and proteins involved in intracellular signaling. FIGS. 9D-9G show qRT-PCR validation of CHI3L1 (FIG. 9D), ITGB4 (FIG. 9E), ITGB3 (FIG. 9F), and TF (FIG. 9G) mRNA levels in control and AxD astrocytes. Error bars are SD of the mean, n=3 experimental repeats, p<0.01 and *p<0.001 by Student's t-test, compared to C1 (FIG. 9D, FIG. 9E) or C3 (FIG. 9F, FIG. 9G).

FIGS. 10A-10C show information about control and AxD brain tissues used in the study. FIG. 10A shows post-mortem control and AxD brain tissues used for RNA-seq and qRT-PCR analyses. FIG. 10B shows H&E staining of control and AxD brain tissues. White arrows point to examples of Rosenthal fibers present in the AxD brain tissue section. Scale bar: 100 μm. FIG. 10C shows heatmap presentation of representative cell membrane protein-encoding genes and intracellular signaling molecules up-regulated (red) or down-regulated (blue) in AxD brain tissues, compared to control brain tissues.

Figure 11A:
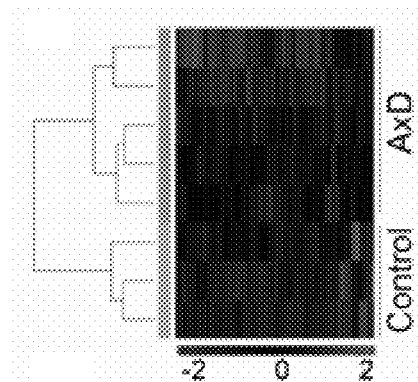
Figure 11B:
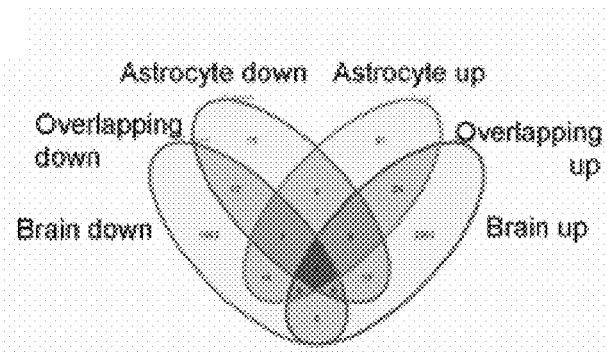
Figure 11C:
Figure 11D:
Figure 11E:
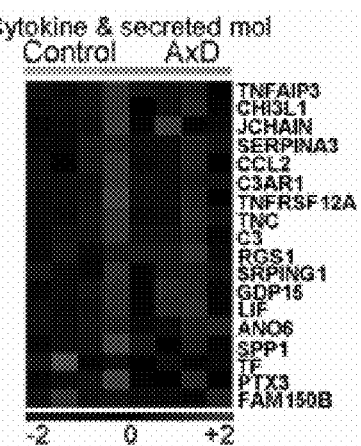
Figure 11F:
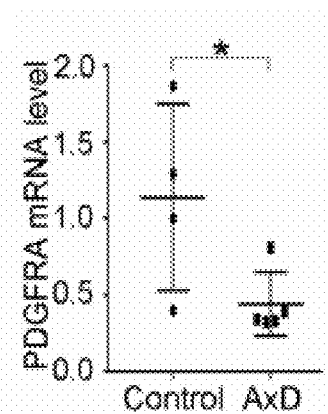
Figure 11G:
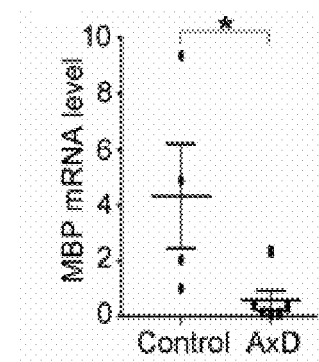
Figure 11H:
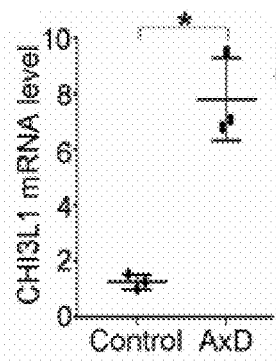
Figure 11I:
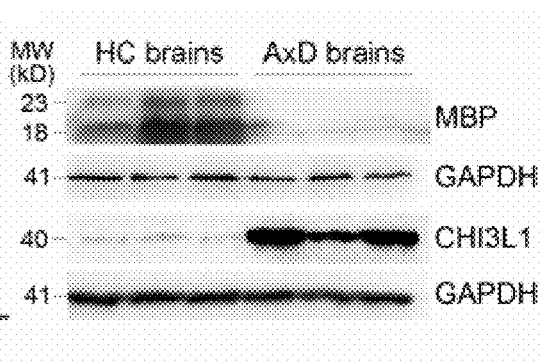

FIGS. 11A-11I show confirmation of CHI3L1 gene expression change in AxD patient brains. FIG. 11A shows heatmap presentation of RNA-seq analysis of post-mortem brain tissues from AxD patients (AxD) and non-AxD controls. Genes up-regulated in AxD brains are shown in red, while genes down-regulated shown in blue. FIG. 11B shows Venn diagram presentation of genes that show consistent changes in AxD astrocytes and brain tissues, compared to control samples. FIG. 11C shows GO terms of genes up-regulated (red) and down-regulated (blue) in both AxD astrocytes and brain tissues, compared to corresponding controls. X axis is enrichment score. Full names of abbreviated GO terms are: axon ensheathment in central nervous system (Axon ensheathment); central nervous system myelination (Myelination); multicellular organismal process (Organismal process); potassium ion transport (Potassium transport). FIG. 11D shows heatmap presentation of myelination-related genes down-regulated (blue) in AxD brain tissues compared to control brain tissue. FIG. 11E shows heatmap presentation of representative genes encoding cytokines and secreted molecules up-regulated (red) or down-regulated (blue) in AxD brain tissues compared to control brain tissues. FIGS. 11F and 11G show qRT-PCR validation of PDGFRA (FIG. 11F) and MBP (FIG. 11G) mRNA levels in control and AxD brain tissues. FIG. 11H shows qRT-PCR validation of CHI3L1 mRNA levels in control and AxD brain tissues. Error bars are SD of the mean, n=3 experimental repeats, and *p<0.05 by Student's t-test for FIGS. 11F, 11G and 11H. FIG. 11I shows Western blot of MBP and CHI3L1 in control and AxD brain tissues. GAPDH was included as the loading control.

Figure 12A:
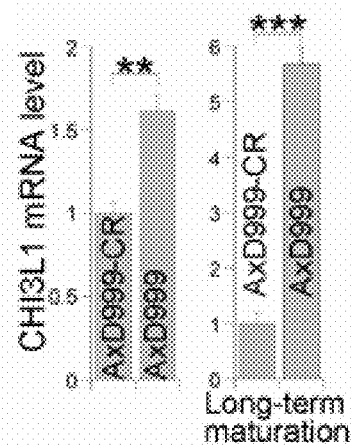
Figure 12B:
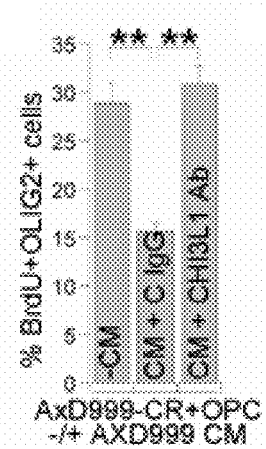
Figure 12C:
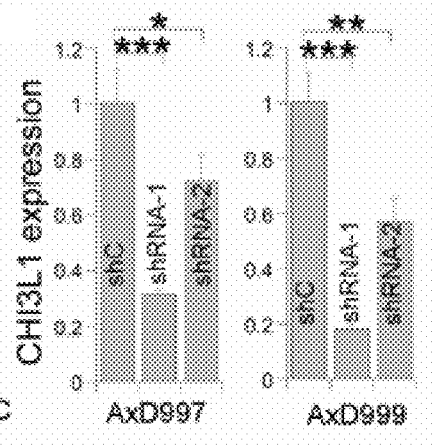
Figure 12D:
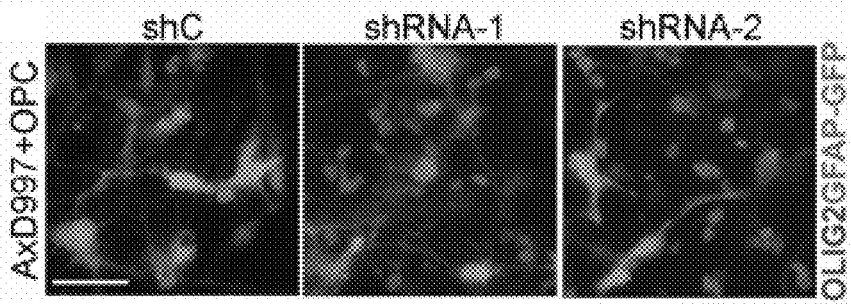
Figure 12E:
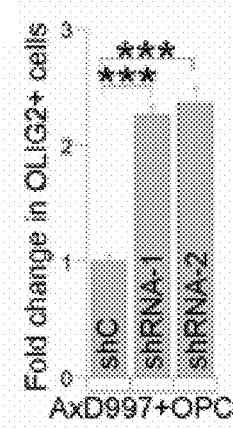

FIGS. 12A-12G show knockdown (KD) of CHI3L1 in AxD astrocytes increased the number of OPCs co-cultured with astrocytes. FIG. 12A shows CHI3L1 mRNA level changes between AxD999-CR and AxD999 astrocytes after short-term maturation or long-term maturation of astrocytes. FIG. 12B shows the percentage of BrdU$^+$ OLIG2$^+$ cells in AxD999-CR astrocyte-OPC co-cultures treated with control medium, medium conditioned from AxD999 astrocytes for 48 hr plus control IgG antibody (CM+C IgG), or medium conditioned from AxD999 astrocytes for 48 hr plus a CHI3L1 neutralizing antibody (CM+CHI3L1 Ab). FIG. 12C shows KD of CHI3L1 mRNA levels in AxD997 and AxD999 astrocytes treated with CHI3L-targeting shRNAs (shRNA-1 and shRNA-2), relative to that treated with control shRNA (shC). FIGS. 12D and 12E show representative images of OLIG2 staining (FIG. 12D) and fold change in OLIG2+ cell number (FIG. 12E) in OPCs co-cultured with control or CHI3L-targeting shRNA-treated AxD997 astrocytes. FIG. 12F shows live staining of OPCs for IL-13Rα2, CRTH2 and TMEM219. HT1080 cells were included as a positive control for IL-13Rα2 staining, while astrocytes were included as a negative control for CRTH2 and TMEM219 staining. FIG. 12G shows CRTH2 mRNA expression as revealed by qRT-PCR in O4$^+$ I90 iPSC-derived OPCs and O4$^+$ mouse primary OPCs. Error bars are SD of the mean, *p<0.05, p<0.01, *p<0.001 by Student's t-test for FIGS. 12A & 12G, and one-way ANOVA for FIGS. 12B, 12C and 12E. Scale bars: 100 μm for FIGS. 12D & 12F.

Figure 13A:
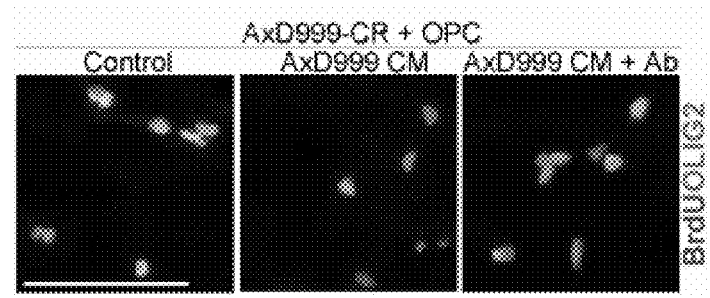
Figure 13B:
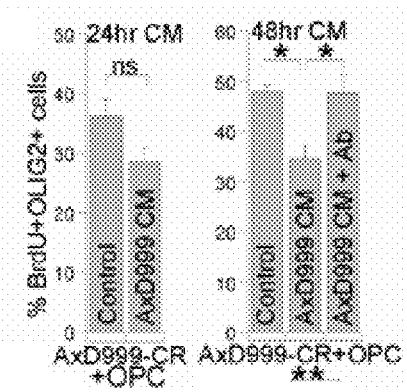
Figure 13C:
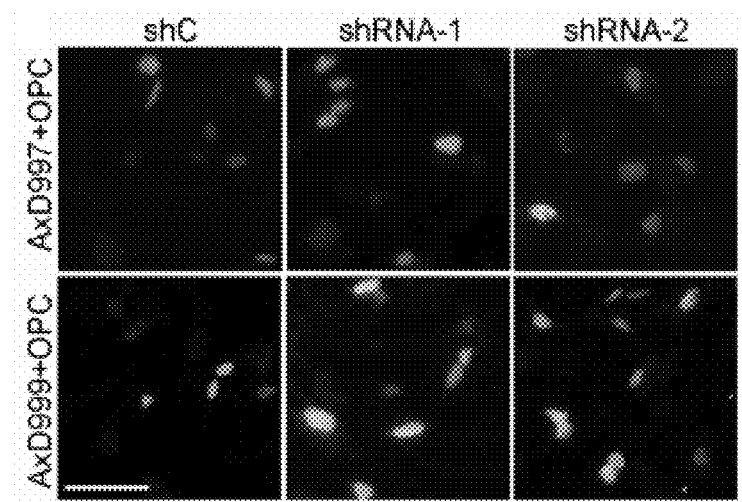
Figure 13D:
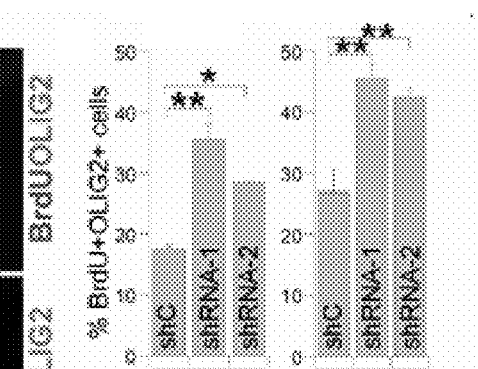
Figure 13E:
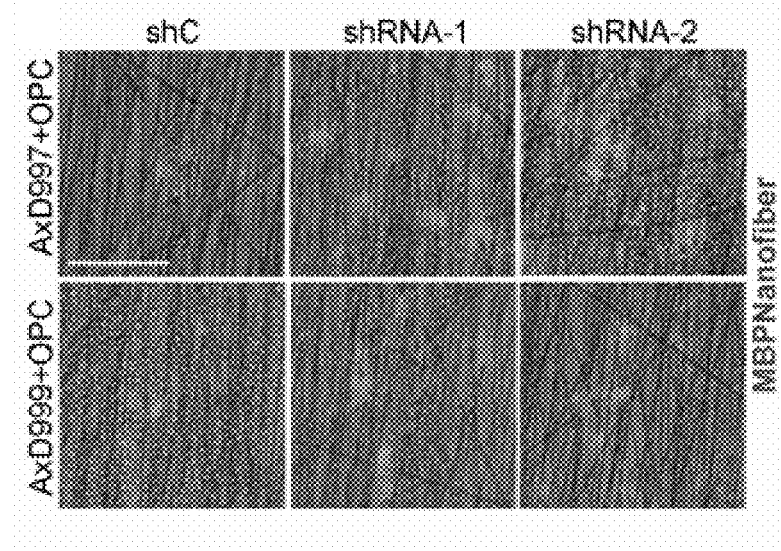
Figure 13F:
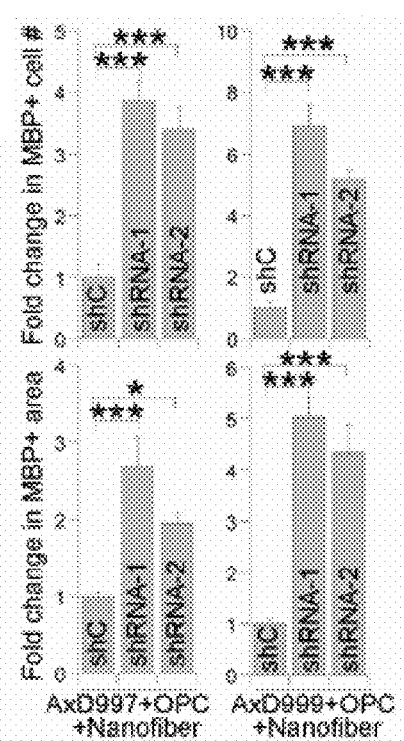

FIGS. 13A-13F show that CHI3L1 mediates the inhibitory effect of AxD astrocytes on OPC proliferation and myelination. FIG. 13A shows representative images of OLIG2 and BrdU staining of AxD999-CR astrocyte-OPC co-cultures treated with control medium, medium conditioned from AxD999 astrocytes for 48 hr (AxD999 CM), or AxD999 CM plus a CHI3L1 neutralizing antibody (Ab). FIG. 13B shows the percentage of BrdU$^+$ OLIG2$^+$ cells in AxD999-CR astrocyte-OPC co-cultures treated with control medium, medium conditioned from AxD999 astrocytes for 24 or 48 hr, or medium conditioned from AxD999 astrocytes for 48 hr plus a CHI3L1 neutralizing antibody (Ab). FIGS. 13C and 13D show representative images of OLIG2 and BrdU staining and the percentage of BrdU$^+$ OLIG2$^+$ cells in OPCs co-cultured with AxD astrocytes treated with control shRNA (shC) or CHI3L1-targeting shRNAs (shRNA-1 and shRNA-2). FIGS. 13E and 13F show representative images of MBP staining and fold change of MBP$^+$ cell number or MBP$^+$ area in 3D nanofiber cultures with OPCs and AxD astrocytes treated with shC or CHI3L1-targeting shRNAs (shRNA-1 and shRNA-2). Error bars are SD of the mean, *p<0.05, p<0.01, *p<0.001 by one-way ANOVA.

Figure 14A:
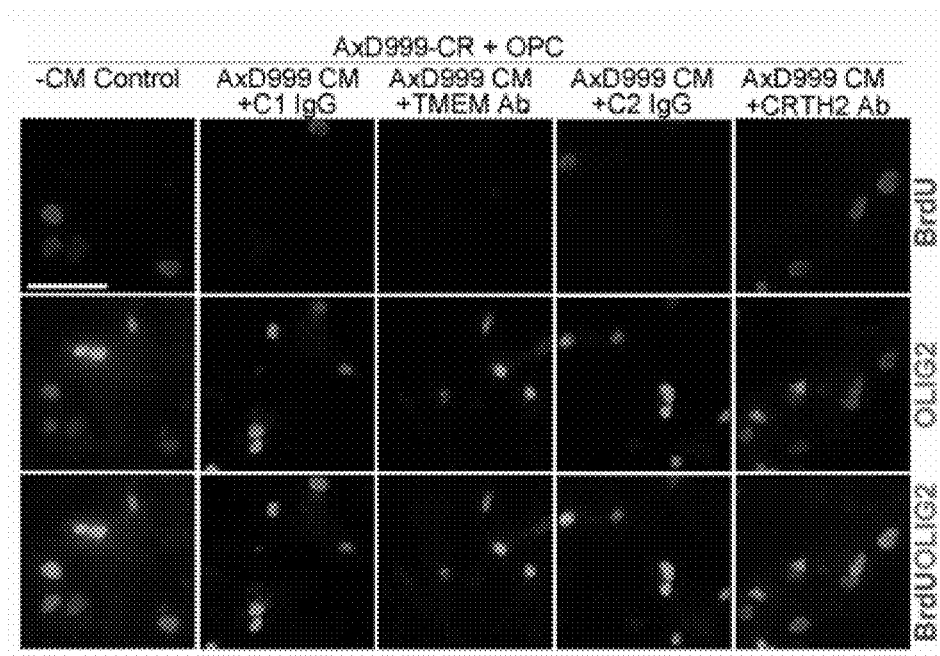
Figure 14B:
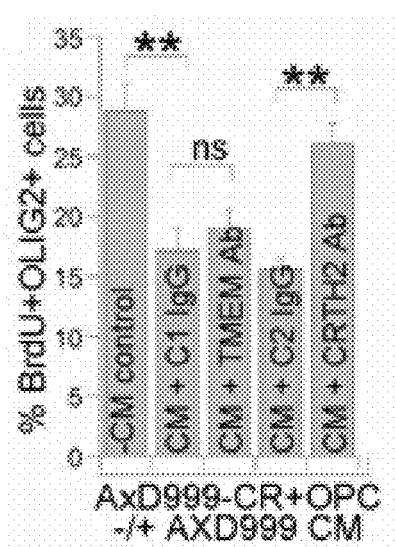

FIGS. 14A-14B show that a neutralizing antibody for CRTH2 rescued the AxD999 astrocyte CM-induced reduction of OPC proliferation. FIG. 14A shows representative images of OLIG2 and BrdU staining of AxD999-CR astrocyte-OPC co-cultures treated with control medium (-CM Control), medium conditioned from AxD999 astrocytes for 48 hr (AxD999 CM) together with a control IgG, or a neutralizing antibody (Ab) for TMEM219 or CRTH2. Sheep IgG (C1 IgG) was included as a negative control for sheep anti-TMEM219 and rabbit IgG (C2 IgG) as a negative control for rabbit anti-CRTH2. FIG. 14B shows the percentage of BrdU$^+$ OLIG2$^+$ cells in OPCs co-cultured with AxD999-CR astrocytes and treated with control medium, AxD999 CM together with a control IgG, or a neutralizing Ab for TMEM219 or CRTH2. Error bars are SD of the mean, n=3 experimental repeats, **p<0.01 by one-way ANOVA. ns: non-significant.

DETAILED DESCRIPTION

Provided herein are methods of detecting the abnormal expression of one or more genes associated with a neurological disease. The method comprises the steps of differentiating astrocytes from induced pluripotent stem cells (iPSCs) obtained from one or more healthy control subjects; differentiating astrocytes from iPSCs obtained from a subject suffering from a neurological disease; performing a transcriptome analysis of the astrocytes derived from the subject suffering from the neurological disease and a transcriptome analysis of the astrocytes derived from the one or more healthy control subjects; comparing the results of both transcriptome analyses to identify one or more genes that are substantially differentially expressed in the subject suffering from the neurological disease comparing to the one or more healthy subjects, correcting the expression of the one or more substantially differentially expressed genes, wherein complete or partial restoring of one or more phenotypes of the neurological disease after gene expression correction indicating that the one or more substantially differentially expressed genes are associated with the neurological disease. By comparing the transcriptome of the astrocytes derived from a subject suffering from a neurological disease with the transcriptome of the astrocytes derived from a healthy control subject, the genes that are substantially up-regulated or down-regulated can be identified. The abnormal expression of these genes can be corrected by administering inhibitors or promoters of these genes. If one or more phenotypes of the neurogenerative disease is completely or partially restored by correcting the abnormal expression of a particular gene, it indicates the correlation between the particular gene and the neurogenerative disease, and therefore, the particular gene can be used as a target for treatment.

Astrocytes are the most abundant type of glial cells in the mammalian central nervous system (CNS). The important functions for astrocytes in neurodevelopment and diseases have been increasingly appreciated because of their key roles in maintaining CNS homeostasis and close interactions with other cell types in the brain (Verkhratsky and Parpura, 2016). Astrocytes are critical for neuronal maturation, synapse formation, and survival (Molofsky et al., 2012; Clarke and Barres, 2013; Allen and Eroglu, 2017). They are also an integral part of blood-brain-barrier (Abbott et al., 2006) and neuroinflammation in the brain (Colombo and Farina, 2016). Growing evidence supports the idea that astrocytes play an important role in regulating myelination (Sofroniew and Vinters, 2010; Lanciotti et al., 2013; Domingues et al., 2016; Kiray et al., 2016). Oligodendrocytes are the myelinating glia of the CNS derived from oligodendrocyte progenitor cells (OPCs) (Domingues et al., 2016). The interplay between astrocytes and OPCs could modulate oligodendrocyte homeostasis and myelination.

Alexander disease (AxD) is unique among the neurological diseases because its primary pathological cause is astrocyte dysfunction. Therefore, the study of AxD offers the rare opportunity to identify astrocyte functions that are required for brain development and involved in pathological brain conditions, and to identify treatments that can restore astrocyte functions. It is expected that the knowledge gained through this study could be applicable to the study and treatment of many more common neurological diseases that also have astrocyte abnormalities.

Using Alexander disease (AxD) as an example, disclosed herein is a method of identifying genes that are differentially expressed in the astrocytes of AxD patients and effective therapies for these patients as well as patients suffering from a neurological disease that is not AxD. AxD is a type of leukodystrophy that primarily affects astrocytes (Messing et al., 2010). It represents the first example of neurological diseases with astrocyte dysfunction as the primary cause (Messing et al., 2012; Lanciotti et al., 2013). AxD is due to mutations in glial fibrillary acidic protein (GFAP), the major intermediate filament protein in astrocytes, resulting in the formation of protein aggregates known as Rosenthal fibers (Iwaki et al., 1989; Johnson and Bettica, 1989). These fibers accumulate within the astrocyte cytoplasm, causing cellular dysfunction with devastating effects on CNS, including OPC and oligodendrocyte loss and demyelination in AxD patients (Prust et al., 2011).

Using AxD as an example, also disclosed herein is a human cellular model for a neurological disease using patient iPSC-derived glial cells. Although multiple animal models such as transgenic mouse models have been established to study AxD and contributed to the knowledge of AxD substantially, none of these models exhibit myelination defect (Messing et al., 1998; Hagemann et al., 2005; Hagemann et al., 2006; Tanaka et al., 2007b; Wang et al., 2011; Wang et al., 2015; Lee et al., 2017), an important pathological phenotype in AxD patients, especially the most common, early onset patients (Messing et al., 2001; van der Knaap et al., 2001). This is likely due to difference between human astrocytes and astrocytes of other species; human astrocytes are much larger and more complex, therefore may contribute to a greater extent to disease progression than astrocytes in rodents and other non-human species (Verkhratsky et al., 2012).

In some embodiments, disclosed herein is a human cellular model of AxD to uncover the mechanisms of AxD pathology that is not recapitulated in animal models. As demonstrated in the working examples, human iPSCs from AxD patients were produced and a co-culture system was established using human iPSC-derived astrocytes and OPCs to study the effect of astrocytes on oligodendroglial lineage cells and myelination. This co-culture system allowed recapitulation of reduced myelination induced by AxD astrocytes, and provided a platform for identifying molecular and cellular mechanisms underlying myelination defect in AxD. Likewise, human cellular models of other neurological diseases associated with astrocytes dysfunctions and myelination defects may be established based on the protocol disclosed herein. Human iPSCs can be differentiated into astrocytes. These astrocytes can be used to study neurological diseases with astrocyte dysfunctions. These diseases include but are not limited to the Alzheimer's disease, the Parkinson disease, the Huntington disease, multiple sclerosis, and amyotrophic lateral sclerosis. In addition, human iPSCs can be differentiated into astrocytes and oligodendrocyte progenitor cells (OPCs). These astrocytes and OPCs can be co-cultured to model diseases with myelination defects, such as leukodystrophy diseases.

Human induced pluripotent stem cells (hiPSCs) provide a valuable tool to study human genetic disorders (Takahashi et al., 2007; Yu et al., 2007), especially neurological diseases, for which human cells and tissues are not easily accessible (Marchetto et al., 2011; Li et al., 2017; Shi et al., 2017). hiPSCs can retain mutations of relevant patients and be differentiated into cell type(s) that are dysfunctional in the disease of interest, thus allowing identification of pathological mechanisms underlying the disease by comparison of patient and healthy control iPSC-derived cells through functional assays, cellular analyses and molecular profiling. Modeling neurological diseases such as AxD using hiPSCs allows to close the knowledge gap between findings from animal models and patient phenotypes.

In human iPSC-based disease modeling, iPSCs derived from healthy individuals are usually used as controls for patient-derived iPSCs. With rapid development of genome editing technologies, the generation of isogenic iPSC lines with the edited gene as the sole variable, allows identification of true pathological phenotypes, without worrying about changes resulted from different genetic or epigenetic background (Hockemeyer and Jaenisch, 2016). For example, studying AxD pathogenesis using isogenic iPSC-derived astrocytes with the GFAP mutation as the sole variant allows identification of pathological phenotypes explicitly caused by the GFAP mutation.

By comparing the transcriptome of astrocytes derived from AxD and healthy control iPSCs, a set of differentially expressed genes were identified. GO analysis revealed that genes involved in cytokine activation and cell membrane are among the up-regulated GO terms. Up-regulation of genes involved in cytokine production and inflammatory response has also been observed in AxD mouse models and patient brain tissues (Olabarria et al., 2015), supporting the validity of the cellular model. It was previously shown that AxD astrocytes secret more interleukin cytokines, including IL5, IL6, and TNFα (Kondo et al., 2016), further supporting the involvement of inflammatory response in AxD. Whether the altered expression of these cytokines is resulted from GFAP mutations and whether it can be detected in AxD patient brains will be tested.

As demonstrated in the working examples, iPSCs were generated from healthy control individuals and AxD patients, and isogenic iPSCs that had the mutant GFAP in AxD iPSCs were corrected to the wild type (WT) genotype through CRISPR/Cas9-based gene editing. Both control and AxD iPSCs were differentiated into astrocytes and established an astrocyte-OPC co-culture system using these astrocytes together with healthy control iPSC-derived OPCs. A co-culture system and a nanofiber-based in vitro myelination assay were used to determine how AxD astrocytes regulate oligodendroglial lineage cell number to modulate myelination, and a transcriptome analysis was performed to identify molecular mechanisms underlying this regulation.

CHI3L1 was identified as a gene that is substantially up-regulated in AxD iPSC-derived astrocytes, compared to control astrocytes. CHI3L1 is a secreted protein from astrocytes, increased expression of which has been linked to neuroinflammatory conditions (Bonneh-Barkay et al., 2012). It has been used as a biomarker for a variety of inflammation-associated diseases (Bhardwaj et al., 2015), including Alzheimer's disease (Craig-Schapiro et al., 2010; Gispert et al., 2016), amyotrophic lateral sclerosis (Sanfilippo et al., 2017), multiple sclerosis (Bonneh-Barkay et al., 2010a; Hinsinger et al., 2015; Burman et al., 2016), and schizophrenia (Arion et al., 2007). Because CHI3L1 is categorized as a gene associated with neuroinflammatory conditions in general and associated with other neurological diseases, CHI3L1 and its receptor can be used as targets for treating neurological diseases other than AxD.

Thus, disclosed herein is a method of identifying target genes for potential treatment of various neurological diseases using AxD as a "simplified" model because astrocytes dysfunction is the primary cause of AxD. The method entails a step of comparing the transcriptome of the astrocytes derived from an AxD patient with the transcriptome of the astrocytes derived from a healthy control subject to identify one or more substantially differentially expressed genes. Subsequently, the identified one or more genes are categorized based on the genes function to determine whether the genes affect the mechanism of a neurological disease other than AxD. If so, the genes can be a potential treatment target for other neurological diseases. In addition to or in the alternative to categorizing the identified one or more genes, the abnormal expression of the genes is validated in a subject suffering from a neurological disease other than AxD and used as a potential treatment target for other neurological diseases.

Using isogenic astrocytes, it was demonstrated that the GFAP mutation in AxD astrocytes is critical for the increased CHI3L1 expression. Correction of the GFAP mutation reversed the elevated expression of CHI3L1 in AxD astrocytes. It was further confirmed the elevated expression of CHI3L1 in brain tissues from multiple AxD patients, and established a causative link between astrocytic CHI3L1 expression and OPC proliferation/myelination. Moreover, the study using a neutralizing antibody against CRTH2 suggests that the astrocytic CHI3L1 could act by binding to the OPC surface receptor CRTH2 to suppress OPC proliferation. CRTH2 has been shown to be involved in cell-cell interactions during inflammatory responses (Harizi, 2013; Taketomi et al., 2013). The CHI3L1/CRTH2 signaling could inhibit OPC proliferation through modulation of intracellular signaling that is important for cell proliferation. The regulation of OPC proliferation could in turn impact myelination.

The human iPSC-based cellular model for a neurological disease disclosed herein can also be used to test the effect of potential therapeutic tools and to screen drugs for the neurological disease and related leukodystrophy disorders. Indeed, using this human cellular platform, it was shown that a neutralizing antibody against CHI3L1 or CRTH2 was able to reverse the inhibitory effect of AxD astrocytes on OPC proliferation. Likewise, CHI3L1 shRNAs were able to rescue the defective OPC proliferation and reduce myelination induced by AxD astrocytes. These results demonstrate the potential of the iPSC-based cellular model for future drug discovery and validation. Therefore, the study of dysfunction in astrocytes derived from iPSCs is of great importance not only for understanding the pathological mechanisms of a neurological disease, but also for drug discovery to enable better treatment of the disease.

According to the embodiments described herein, a pharmaceutical composition for treating a neurological disease is provided herein. In one embodiment, the pharmaceutical composition may include an effective amount of an inhibitor or a promoter that corrects the abnormal expression of one or more genes in the subject suffering from the neurological disease, the abnormal expression of the one or more genes detected using the patient-based astrocytes and the methods described herein. The pharmaceutical composition as described herein may further comprise a pharmaceutically acceptable carrier according to a standard method. Examples of acceptable carriers include physiologically acceptable solutions, such as sterile saline and sterile buffered saline.

The term "effective amount" as used herein refers to an amount of a composition that produces a desired effect. For example, a population of cells may be contacted with an effective amount of a compound or molecule to study its effect in vitro (e.g., cell culture) or to produce a desired therapeutic effect ex vivo or in vitro. An effective amount of a compound or a composition may be used to produce a therapeutic effect in a subject, such as treating a particular neurological disease, alleviating symptoms associated with the disease, or producing a desired physiological effect. In such a case, the effective amount of a composition is a "therapeutically effective amount," "therapeutically effective concentration" or "therapeutically effective dose." The precise effective amount or therapeutically effective amount is an amount of the composition that will yield the most effective results in terms of efficacy of treatment in a given subject or population of cells. This amount will vary depending upon a variety of factors, including but not limited to the characteristics of the composition (including activity, pharmacokinetics, pharmacodynamics, and bioavailability), the physiological condition of the subject (including age, sex, disease type and stage, general physical condition, responsiveness to a given dosage, and type of medication) or cells, the nature of the pharmaceutically acceptable carrier or carriers in the formulation, and the route of administration. Further, an effective or therapeutically effective amount may vary depending on whether the composition is administered alone or in combination with another composition, drug, therapy or other therapeutic method or modality. One skilled in the clinical and pharmacological arts will be able to determine an effective amount or therapeutically effective amount through routine experimentation, namely by monitoring a cell's or subject's response to administration of a composition and adjusting the dosage accordingly. For additional guidance, see Remington: The Science and Practice of Pharmacy, 21$^{st}$ Edition, Univ. of Sciences in Philadelphia (USIP), Lippincott Williams & Wilkins, Philadelphia, Pa., 2005, which is hereby incorporated by reference as if fully set forth herein.

"Treating" or "treatment" of a disease or condition may refer to preventing the disease or condition, slowing the onset or rate of development of the disease or condition, reducing the risk of developing the disease or condition, preventing or delaying the development of symptoms associated with the disease or condition, reducing or ending symptoms associated with the disease or condition, generating a complete or partial regression of the disease or condition, completely or partially restoring one or more phenotypes associated with the disease or condition, or some combination thereof. Treatment may also mean a prophylactic or preventative treatment of a disease or condition.

The following examples are intended to illustrate various embodiments of the invention. As such, the specific embodiments discussed are not to be constructed as limitations on the scope of the invention. It will be apparent to one skilled in the art that various equivalents, changes, and modifications may be made without departing from the scope of invention, and it is understood that such equivalent embodiments are to be included herein. Further, all references cited in the disclosure are hereby incorporated by reference in their entirety, as if fully set forth herein.

EXAMPLES

Example 1: Materials and Methods

Derivation of IPSCs from Fibroblasts of AxD Patients and Healthy Controls.

AxD997 (female) and AxD999 (male) fibroblasts were obtained from Telethon Network, AxD825 (male) fibroblast and control fibroblast 190 (IMR90; female) from Coriell, control fibroblast C1 (CRL-2092; male) from ATCC. All fibroblast lines were reprogrammed using episomal plasmids expressing OCT4, SOX2, L-MYC, KLF4, shp53, and EBNA1 (Addgene Plasmids pCXLE-hSK, pCXLE-hUL, pCXLE-hOCT3/4-shp53-F, and pCXWB-EBNA1). Cells electroporated with reprogramming plasmids using 4D Nucleofector (Lonza) were seeded into 6-well plates coated with 1:100 diluted Matrigel (Corning) and maintained in mTeSR1 medium (Stem Cell Technologies). C3 iPSCs were generated and characterized previously (Wen et al., 2014b; Murai et al., 2016). iPSCs generated from AxD and control fibroblasts were maintained at 37° C. in mTeSR1 medium in Matrigel-coated 6-well plates and passaged every 3-4 days using 0.5 mM EDTA (Gibco) treatment and manual dissociation. Small clusters of iPSCs were transferred to new plates coated with Matrigel at 1:6 to 1:10 ratio. Medium was changed daily. All iPSC lines generated in this study were authenticated using STR assay.

Primary Cell Cultures.

The human primary astrocytes were purchased from ScienCell Research Laboratories (ScienCell, Cat #1800) and cultured at 37° C. in astrocyte medium (ScienCell, Cat #1801) containing 500 ml of basal medium, 10 ml of fetal bovine serum, 5 ml of astrocyte growth supplement and 5 ml of penicillin/streptomycin. Gender information of this product was not released by the vendor.

Animals.

Rag2$^{-/-}$ mice (The Jackson Laboratory, RRID:IMSR_JAX:008449) were used for astrocyte transplantation and mouse primary OPC isolation. NSG mice (The Jackson Laboratory, RRID:IMSR_JAX:005557) were used for teratoma formation assay. All animal work was performed without gender bias under the Institutional Animal Care and Use Committee (IACUC) protocol approved by the City of Hope IACUC Committee.

Generation of Isogenic iPSCs Using CRISPR/Cas9 Nickase.

The pSpCas9n (BB)-2A-GFP plasmid containing Cas9n (D10A nickase mutant) with 2A-EGFP and cloning backbone for sgRNA was purchased from Addgene (Plasmid #48140). Guide RNAs were designed to generate DNA double-strand breaks that cover M73K mutation site using an online designing tool (crispr.mit.edu). The oligonucleotides for sgRNA were synthesized by Integrated DNA Technologies (IDT) and cloned to pSpCas9n (BB)-2A-GFP plasmid according to previously published protocol (Ran et al., 2013b). The single-strand donor DNA (ssODN) contains A to T correction at the M73K mutation site of the human GFAP gene, and includes a silent G to A mutation at one of the protospacer adjacent motif (PAM) sites to avoid repeated cutting by Cas9n. Another silent mutation, C to G, was introduced to create AgeI digestion site that allowed identification of clones with successful homologous recombination. The sequences of sgRNAs and ssODNs were summarized in Table 1.

TABLE 1

Oligonucleotide sequences for gene editing and PCR

| Oligonucleotide Name | Oligonucleotide Sequence |
|---|---|
| sgRNA target-3 (SEQ ID NO: 1) | 5'-CATCATCTCTGCCCGCTCAC-3' |
| sgRNA target-4 (SEQ ID NO: 2) | 5'-CTTTGCCAGCTACATCGAGA-3' |
| ssODN (SEQ ID NO: 3) | 5'-CTCGAATGCCCCCTCCACTCCCGACCCGGGTGGATTTCTCCCTGGCTGGGGCACTCAATGCTGGCTTCAAGGAGACCCGGGCTAGTGAGCGGGCAGAGATGATGGAGCTCAATGACCGGTTTGCCAGCTACATCGAGAAAGTTCGCTTCCTGGAACAGCAAAACAAGGCGCTGGCTGCTGAGCTGAACCAGCTGCGGGCC-3' |
| GFAP M73K and R79C Forward (SEQ ID NO: 4) | 5'-CTCCTTCATAAAGCCCTCGCA-3' |

TABLE 1-continued

Oligonucleotide sequences for gene editing and PCR

| Oligonucleotide Name | Oligonucleotide Sequence |
|---|---|
| GFAP M73K and R79C Reverse (SEQ ID NO: 5) | 5'-GACACAGGCTCAGAATAGGTGA-3' |
| GFAP R239C Forward (SEQ ID NO: 6) | 5'-CAGAGAAGCTGAGACTGAGAG-3' |
| GFAP R239C Reverse (SEQ ID NO: 7) | 5'-GAGAGAGACACTCAGAGAGAG-3' |
| CHI3L1 Forward (SEQ ID NO: 8) | 5'-GTGAAGGCGTCTCAAACAGG-3' |
| CHI3L1 Reverse (SEQ ID NO: 9) | 5'-GGTCAAGGGCATCTGGGAAG-3' |
| CRTH2 Forward (SEQ ID NO: 10) | 5'-GGTCACCACCTGGGTGCTGC-3' |
| CRTH2 Reverse (SEQ ID NO: 11) | 5'-GCTGGGCACCACCTTCTGC-3' |
| ITGB4 Forward (SEQ ID NO: 12) | 5'-CCGATGATCTGGACAACCTC-3' |
| ITGB4 Reverse (SEQ ID NO: 13) | 5'-GCTTCTCAGGCCTCATGTC-3' |
| MBP Forward (SEQ ID NO: 14) | 5'-CTATAAATCGGCTCACAAGG-3' |
| MBP Reverse (SEQ ID NO: 15) | 5'-AGGCGGTTATATTAAGAAGC-3' |
| PDGFRA Forward (SEQ ID NO: 16) | 5'-AAGAAGTCCAGGTGAGGTTAGAG-3' |
| PDGFRA Reverse (SEQ ID NO: 17) | 5'-GGCTGCTTTAGGTGGGTTT-3' |
| ITGB3 Forward (SEQ ID NO: 18) | 5'-AGGTCACTCAAGTCAGTCCC-3' |
| ITGB3 Reverse (SEQ ID NO: 19) | 5'-CGGCCAGATGATTCGAAGAA-3' |
| TF Forward (SEQ ID NO: 20) | 5'-AAGCCTCCTACCTTGATTGC-3' |
| TF Reverse (SEQ ID NO: 21) | 5'-CCACCACAGGCTTCAGGTTA-3' |
| GAPDH Forward (SEQ ID NO: 22) | 5'-AGCCACATCGCTCAGACAC-3' |
| GAPDH Reverse (SEQ ID NO: 23) | 5'-GCCCAATACGACCAAATCC-3' |
| ACTIN Forward (SEQ ID NO: 24) | 5'-CCGAGCGTGGCTACAGCTTC-3' |
| ACTIN Reverse (SEQ ID NO: 25) | 5'-ACCTGGCCGTCAGGCAGCTC-3' |

Table 2 lists top genes that were up-regulated or down-regulated in AxD vs control human iPSC-derived astrocytes and brain tissues. The top-listed genes with |fold changes|>1.2 in both AxD astrocytes and AxD brain tissues vs their controls, and with the same trend of change in both lines of AxD astrocytes vs their control astrocytes, were included. The p values are for n=12 DESeq2 comparison (AxD vs WT, adjust for cell or tissue status). I90 and AxD999 astrocytes were derived using the method developed in this study, while C3 and AxD997 astrocytes were derived by following a published protocol (Krencik and Zhang, 2011).

TABLE 2

Top genes exhibiting expression changes in AxD vs control iPSC-derived astrocytes and brain tissues revealed by RNA-seq

| Gene Symbol | AxD Average $\log_2$(RPKM + 0.1) | Control Average $\log_2$(RPKM + 0.1) | Overall Fold Change | Brain Fold Change | Astrocyte Fold Change | AxD997 vs C3 Astrocyte Fold Change | AxD999 vs I90 Astrocyte Fold Change | Overall P Value |
|---|---|---|---|---|---|---|---|---|
| CHI3L1 | 3.500162703 | −0.633261188 | 17.51 | 20.06572882 | 3.8828752 | 4.526057052 | 3.331093669 | 2.15E−11 |
| PDPN | 4.809302472 | 0.844701165 | 15.56 | 11.01687659 | 28.259526 | 194.0794777 | 4.114813302 | 0.000294 |
| SPP1 | 8.201062002 | 4.633348668 | 11.88 | 15.62196394 | 7.1254058 | 12.0723097 | 4.205608478 | 9.04E−06 |
| C3AR1 | 2.69837754 | −0.726183715 | 10.7 | 7.107780411 | 13.334336 | 5.445778138 | 32.64997584 | 1.07E−11 |
| ITGB4 | 4.272905124 | 0.918177805 | 10.2 | 13.03479481 | 7.5733727 | 5.623769751 | 10.19884824 | 1.43E−11 |
| HLA-B | 6.505421184 | 3.437337916 | 8.4 | 4.848135862 | 13.936146 | 4.558863339 | 42.6018817 | 0.000396 |
| CP | 1.093504131 | −1.971102839 | 8.34 | 8.912981682 | 5.1149953 | 7.012367017 | 3.731005101 | 2.92E−16 |
| PLXDC2 | 2.361094131 | −0.661263413 | 8.11 | 5.629371086 | 6.2570437 | 3.610637265 | 10.84312631 | 7.41E−10 |
| SLC4A11 | 1.465784107 | −1.472964951 | 7.67 | 14.14227054 | 2.9348665 | 3.527813709 | 2.4415806 | 7.92E−09 |

TABLE 2-continued

Top genes exhibiting expression changes in AxD vs control iPSC-derived astrocytes and brain tissues revealed by RNA-seq

| Gene Symbol | AxD Average log$_2$(RPKM + 0.1) | Control Average log$_2$(RPKM + 0.1) | Overall Fold Change | Brain Fold Change | Astrocyte Fold Change | AxD997 vs C3 Astrocyte Fold Change | AxD999 vs I90 Astrocyte Fold Change | Overall P Value |
|---|---|---|---|---|---|---|---|---|
| DOCK2 | 1.043060804 | −1.860032824 | 7.46 | 7.498834278 | 4.243289 | 2.383570709 | 7.554003672 | 1.32E-13 |
| SERPING1 | 4.342215305 | 1.456473662 | 7.41 | 4.120785771 | 11.410343 | 32.38283972 | 4.020522552 | 3.39E-07 |
| ALOX5 | 1.810947044 | −1.028982267 | 7.16 | 8.230878252 | 2.823109 | 4.984392947 | 1.598979948 | 2.53E-05 |
| PIFO | 2.056516825 | −0.78469635 | 7.16 | 4.412115394 | 13.173969 | 10.4842338 | 16.55375675 | 3.21E-09 |
| AIM1 | 0.188525844 | −2.454728559 | 6.23 | 2.816945756 | 39.197235 | 39.41978153 | 38.97594515 | 3.08E-05 |
| FLNC | 4.200510843 | 1.649605677 | 5.86 | 12.43997178 | 2.117685729 | 2.190195101 | 2.047576878 | 4.54E-05 |
| LINC00601 | −0.297949664 | −2.847817115 | 5.86 | 8.360853988 | 2.658352166 | 2.164487798 | 3.264900012 | 5.51E-09 |
| METTL7B | 3.126258422 | 0.580018101 | 5.86 | 14.67053931 | 1.513456827 | 1.641123533 | 1.395721601 | 0.001229 |
| ITGB3 | 0.597891983 | −1.893102175 | 5.62 | 5.377654632 | 6.587277407 | 3.434341453 | 12.63480182 | 1.12E-05 |
| LIF | 1.379565176 | −1.089400918 | 5.54 | 7.987331011 | 6.521991116 | 5.301237055 | 8.023857013 | 5.99E-07 |
| RAB20 | 1.889266278 | −0.570014251 | 5.5 | 5.616679327 | 3.256048058 | 2.132509807 | 4.971535849 | 0.000128 |
| CDCP1 | 0.87509897 | −1.566240379 | 5.43 | 5.225253906 | 12.52974844 | 52.18847291 | 3.008223601 | 0.000162 |
| IGFBP5 | 6.433390051 | 3.993043486 | 5.43 | 3.5254586 | 14.83767093 | 108.2813838 | 2.033188634 | 3.65E-05 |
| BMF | 1.025259144 | −1.393626519 | 5.35 | 7.503469966 | 2.425474106 | 2.254309186 | 2.609635215 | 0.002925 |
| HCP5 | 1.024429125 | −1.377146495 | 5.28 | 3.689780699 | 5.677304145 | 10.25861787 | 3.141922503 | 2.31E-05 |
| ICOSLG | 1.255502119 | −1.113332047 | 5.17 | 5.12838716 | 2.525968153 | 1.963822765 | 3.24902798 | 1.79E-05 |
| IL13RA1 | 3.918704502 | 1.553934836 | 5.13 | 6.395930848 | 3.024520351 | 3.920294624 | 2.333427518 | 8.57E-15 |
| TNFAIP3 | 1.113435795 | −1.246847909 | 5.13 | 5.329094079 | 3.041949983 | 3.381897159 | 2.736174183 | 5.82E-08 |
| GRAMD3 | 3.249497903 | 0.90710799 | 5.06 | 2.489160554 | 10.63630752 | 31.45854529 | 3.596194186 | 0.000806 |
| HMOX1 | 3.296868561 | 0.962038628 | 5.03 | 5.492900059 | 2.730453313 | 1.596466708 | 4.669922182 | 0.000402 |
| PDCD1LG2 | −0.013354182 | −2.3305402 | 4.99 | 5.180646736 | 4.276367395 | 11.63156194 | 1.572215167 | 4.64E-08 |
| CPQ | 2.799279868 | 0.498421631 | 4.92 | 3.672652072 | 4.742294628 | 6.928604206 | 3.245871415 | 4.10E-05 |
| TMEM132E | 2.404267236 | 0.102215903 | 4.92 | 2.360342179 | 18.38903682 | 4.482881435 | 75.43288394 | 0.002145 |
| VWVTR1 | 5.47019397 | 3.175177212 | 4.92 | 10.63847566 | 1.888052063 | 1.289081163 | 2.765334482 | 4.46E-06 |
| RHBDF2 | 1.242011593 | −1.051916197 | 4.89 | 5.606619596 | 1.647122739 | 1.334676294 | 2.032712599 | 6.71E-09 |
| SLC37A2 | 0.260785801 | −2.028850208 | 4.89 | 7.371458829 | 1.520944258 | 1.399126067 | 1.653368834 | 5.13E-07 |
| LCP1 | 1.187922094 | −1.089752123 | 4.86 | 5.200019618 | 1.418433294 | 1.480283575 | 1.359167287 | 1.48E-08 |
| ME1 | 3.204815934 | 0.930379355 | 4.82 | 1.835351818 | 12.8916997 | 10.9290831 | 15.20675792 | 0.001393 |
| RUNX1 | 2.149653701 | −0.112224527 | 4.79 | 5.415459506 | 7.095728819 | 4.131632897 | 12.18631198 | 1.76E-09 |
| CYP27A1 | 2.805354813 | 0.569267979 | 4.72 | 3.887861112 | 3.751113214 | 10.75037251 | 1.308870955 | 3.41E-05 |
| SELL | 0.306244443 | −1.930122451 | 4.72 | 3.209624617 | 6.56947709 | 2.800777749 | 15.40930167 | 0.001799 |
| GSDMD | 1.12211706 | −1.109999716 | 4.69 | 3.115794276 | 5.982646103 | 23.64844569 | 1.513505575 | 0.000546 |
| EMILIN2 | 0.937779633 | −1.275644013 | 4.63 | 2.778704659 | 11.3666194 | 6.491480878 | 19.90301427 | 0.000127 |
| TMCO4 | 0.37553339 | −1.830330455 | 4.63 | 4.75425355 | 3.213471122 | 3.409475767 | 3.028734432 | 4.48E-05 |
| S100A6 | 7.2089504 | 5.009224336 | 4.59 | 4.848026393 | 4.317082359 | 3.066604616 | 6.077470827 | 2.75E-09 |
| ABCC3 | 2.513351281 | 0.328335987 | 4.56 | 7.258853886 | 4.3304474 | 4.637696993 | 4.043553235 | 2.07E-11 |
| SLC40A1 | 2.051439926 | −0.128456765 | 4.53 | 2.918742115 | 6.642897564 | 5.132244769 | 8.598204105 | 1.84E-07 |
| SOCS3 | 4.502367605 | 2.317718585 | 4.53 | 8.676125954 | 2.152139596 | 2.646813114 | 1.749917596 | 0.00016 |
| APOBEC3C | 2.441063244 | 0.268835949 | 4.5 | 5.282903859 | 4.137159212 | 3.037430606 | 5.635054284 | 2.01E-05 |
| PARVG | 0.633553211 | −1.515998736 | 4.44 | 5.119740197 | 1.548046607 | 1.902679144 | 1.259512569 | 9.58E-09 |
| MXRA5 | 0.291298378 | −1.841401121 | 4.38 | 1.918989227 | 21.64391247 | 14.33256389 | 32.68493696 | 0.001964 |
| RIOK1 | 2.1050109 | 2.6949543 | −1.51 | −1.4530504 | −1.5005775 | −1.242593 | −1.8121242 | 0.001019 |
| CHRM4 | 0.2784199 | 0.8887508 | −1.53 | −2.2091423 | −1.5275273 | −1.7214443 | −1.3554546 | 2.10E-06 |
| PRSS8 | −3.1577854 | −2.5495148 | −1.53 | −1.4423294 | −1.5560192 | −1.7056135 | −1.4195453 | 0.001605 |
| FAM84A | 1.4888864 | 2.1183145 | −1.55 | −1.7309145 | −2.9581093 | −3.3571619 | −2.6064905 | 0.000333 |
| NKPD1 | −2.7031441 | −2.0583307 | −1.56 | −1.4214815 | −1.9698726 | −1.757547 | −2.2078487 | 0.000204 |
| ADORA2A | −2.7118313 | −2.0396645 | −1.59 | −1.4751992 | −1.6532776 | −1.4654379 | −1.8651946 | 0.003313 |
| DIRAS1 | 3.9151897 | 4.5907574 | −1.6 | −1.7996463 | −2.5424478 | −3.2238522 | −2.0050673 | 9.94E-05 |
| WASH7P | −1.9207833 | −1.2408651 | −1.6 | −1.5755717 | −1.4694205 | −1.1291547 | −1.7710605 | 0.002139 |
| AOC2 | −0.8282566 | −0.1141306 | −1.64 | −1.633415 | −1.9092044 | −2.1695504 | −1.6800999 | 0.002955 |
| CTNNA3 | −2.7245823 | −2.0113322 | −1.64 | −1.6740844 | −1.8178522 | −1.4592693 | −2.2645488 | 0.000234 |
| SLC12A8 | 0.1245098 | 0.8514457 | −1.66 | −1.3589841 | −2.6173969 | −2.7251178 | −2.5139342 | 0.000378 |
| SEMA4A | 0.8338443 | 1.5767739 | −1.67 | −1.9444344 | −3.2926085 | −1.8932485 | −5.7262797 | 0.000102 |
| ELAVL3 | 4.7250373 | 5.4749998 | −1.68 | −1.6864777 | −2.7137418 | −2.9304513 | −2.5130581 | 0.00018 |
| ZMYND8 | 2.6486237 | 3.4017221 | −1.68 | −1.2185875 | −2.4063371 | −3.4322742 | −1.6870616 | 0.001987 |
| C15orf59 | 3.6345266 | 4.3911614 | −1.69 | −1.3843874 | −4.656846 | −5.9772713 | −3.6281129 | 0.000142 |
| UBAP1L | 0.1469413 | 0.902323 | −1.69 | −1.8473406 | −1.6530248 | −1.4241925 | −1.9186247 | 2.90E-05 |
| EME2 | 0.2677056 | 1.3207225 | −2.07 | −2.0441291 | −1.6544777 | −1.9876935 | −1.377122 | 3.62E-05 |
| FAM212B | 2.9311329 | 3.9861174 | −2.07 | −1.7036676 | −3.0435996 | −1.97519 | −4.6899277 | 3.05E-05 |
| PLAC8L1 | −1.3885957 | −0.3334303 | −2.08 | −1.7711175 | −2.3534758 | −1.9438322 | −2.8494477 | 0.003485 |
| CCDC78 | −1.2178443 | −0.1442854 | −2.1 | −1.6282558 | −2.2004824 | −1.4579571 | −3.3211696 | 0.001819 |
| KCNJ4 | 2.7054978 | 3.7921563 | −2.13 | −2.1392063 | −7.145331 | −7.9274142 | −6.4404043 | 0.000877 |
| SGK223 | 1.9531299 | 3.0598481 | −2.16 | −1.4774177 | −3.428039 | −2.4863371 | −4.7264099 | 0.002005 |
| C10orf111 | −1.5668288 | −0.44457 | −2.17 | −2.3611046 | −2.207605 | −2.2964083 | −2.1222362 | 1.59E-05 |
| GNG7 | 3.6909011 | 4.809181 | −2.17 | −2.1734407 | −3.786099 | −2.4132773 | −5.9398656 | 2.40E-11 |
| NMNAT2 | 2.5182183 | 3.663086 | −2.2 | −1.5870324 | −10.81292 | −19.323144 | −6.0507358 | 0.000525 |
| AACSP1 | −3.1317009 | −1.9714126 | −2.23 | −2.1295088 | −2.508636 | −1.2068508 | −5.2146079 | 9.31E-05 |
| PKDCC | 0.7737203 | 1.9469469 | −2.25 | −2.0737489 | −4.065697 | −4.9685323 | −3.3269162 | 1.89E-05 |
| HSP90AB4P | −1.1972296 | −0.0133336 | −2.27 | −1.7968974 | −4.399978 | −3.1675528 | −6.1119123 | 9.64E-06 |
| ID12-AS1 | −2.171637 | −0.9941978 | −2.27 | −2.5296128 | −1.802658 | −1.241162 | −2.6181718 | 0.003346 |
| SYT12 | 1.3388941 | 2.5394466 | −2.3 | −2.0755529 | −3.607811 | −1.5261546 | −8.5288226 | 0.001174 |

TABLE 2-continued

Top genes exhibiting expression changes in AxD vs control iPSC-derived astrocytes and brain tissues revealed by RNA-seq

| Gene Symbol | AxD Average log$_2$(RPKM + 0.1) | Control Average log$_2$(RPKM + 0.1) | Overall Fold Change | Brain Fold Change | Astrocyte Fold Change | AxD997 vs C3 Astrocyte Fold Change | AxD999 vs I90 Astrocyte Fold Change | Overall P Value |
|---|---|---|---|---|---|---|---|---|
| WNK2 | 1.5380638 | 2.7405969 | −2.3 | −1.6885587 | −9.850627 | −34.773313 | −2.7904976 | 0.00294 |
| GOLGAP72 | −2.1451695 | −0.8811704 | −2.39 | −2.6080101 | −1.724574 | −1.3611922 | −2.1849639 | 3.47E−06 |
| COL9A1 | −0.6156515 | 0.7092069 | −2.5 | −2.865661 | −3.281975 | −2.9481802 | −3.6535626 | 3.62E−06 |
| KCNG1 | 1.8889292 | 3.2070496 | −2.5 | −2.8996374 | −4.015566 | −4.1520154 | −3.8836011 | 5.20E−05 |
| YBX2 | −0.8727653 | 0.4537232 | −2.51 | −2.5261209 | −3.749824 | −4.8018555 | −2.9282813 | 8.15E−06 |
| ACTN2 | 1.5264946 | 2.8660686 | −2.53 | −2.2032307 | −6.220575 | −5.3201133 | −7.2734464 | 0.00015 |
| LINC00473 | −2.4890872 | −1.1221356 | −2.58 | −3.0619085 | −2.371396 | −3.8534871 | −1.4593322 | 6.61E−09 |
| ZDHHC11 | −1.4459054 | −0.0757393 | −2.58 | −2.284724 | −2.53572 | −1.5117012 | −4.2534044 | 0.000628 |
| CNKSR1 | −1.0447405 | 0.3397808 | −2.6 | −2.3874355 | −2.866984 | −2.3846653 | −3.446856 | 0.002643 |
| MOB3B | 0.8187122 | 2.2727984 | −2.73 | −2.1997563 | −4.158952 | −2.3252049 | −7.4388629 | 2.48E−06 |
| BTBD17 | 0.1226705 | 1.6631085 | −2.91 | −1.6946365 | −9.009232 | −11.301852 | −7.1816784 | 0.000214 |
| NR4A1 | 1.2164517 | 2.9673211 | −3.36 | −3.937164 | −4.916743 | −2.1566297 | −11.209325 | 7.77E−06 |
| ADAMTS3 | 0.0260097 | 1.800689 | −3.41 | −1.815748 | −5.067521 | −6.022553 | −4.2639347 | 0.001014 |
| ARC | 1.2649643 | 3.0642522 | −3.48 | −5.2632104 | −3.240165 | −1.7911113 | −5.8615399 | 0.000731 |
| CNDP1 | −1.6910748 | 0.4378211 | −4.38 | −7.2982067 | −3.065324 | −2.5408332 | −3.6980838 | 1.56E−08 |

AxD999 iPSCs were transfected with the CRISPR/Cas9n plasmid and the ssODN using 4D Nucleofector (Lonza). After electroporation, cells were seeded onto Matrigel-coated plates and cultured in mTeSR1 medium supplemented with 10 µM Rock Inhibitor for overnight. The next day, cells were fed with fresh mTeSR1 medium. Cells were harvested 2 days after electroporation and sorted using GFP-based FACS. The sorted cells were plated at low density and maintained in mTeSR1 medium for about 10 to 14 days to allow colony formation from single cells.

To screen for gene-corrected clones, individual colonies were manually split to 2 halves. One half was used for genomic DNA (gDNA) extraction and the other half was seeded into 48-well plates for maintenance. PCR was performed to amplify regions covering the M73K mutation site using genomic DNA as the template. The PCR products were digested using AgeI restriction enzyme. Clones that could be digested by AgeI were further analyzed by Sanger sequencing to confirm the correction of M73K mutation site. The potential off-target sites were predicted by an online tool (www.sanger.ac.uk/htgt/wge/find_off_targets_by_seq). All the sites that contain 0-3 mismatches with sgRNAs were PCR-amplified and sequenced by Sanger sequencing. The off-target site sequences, PCR primers and analysis results are listed in Table 3.

TABLE 3

Lack of mutation in sgRNA3 and sgRNA4 putative off-target sites

| Locus | Sequence | Mismatch | Forward Primer | Reverse Primer | Mutation |
|---|---|---|---|---|---|
| Original sgRNA3 | CATCATCTCTGCC CGCTCAC TGG (SEQ ID NO: 26) | 0 | | | |
| 19:1005100-1005122 | TATCAACTCCGCC CGCTCAC AGG (SEQ ID NO: 27) | 3 | gtgggtgacggcaagtacg (SEQ ID NO: 28) | tggtggagaagaaggggct (SEQ ID NO: 29) | − |
| 22:45220953-45220975 | CACCATCACTGC CTGCTCAC TGG (SEQ ID NO: 30) | 3 | Cccacttctcacaaaacac tgc (SEQ ID NO: 31) | Cttggtggaggaatttgagc tg (SEQ ID NO: 32) | − |
| 16:4329650-4329672 | CAGCATCTCTCCC CACTCAC AGG (SEQ ID NO: 33) | 3 | Tgtgtccctagaagcagag ga (SEQ ID NO: 34) | atatgccccgtgtgtttcc (SEQ ID NO: 35) | − |
| 6:155951855-155951877 | CTTCATCTCTGTC CTCTCAC AGG (SEQ ID NO: 36) | 3 | atgcatttgtcagttcacccc (SEQ ID NO: 37) | taacctttgcagaggctcgtc (SEQ ID NO: 38) | − |
| 17:41516167-41516189 | CCTCATCTCTGCC AGCACAC GGG (SEQ ID NO: 39) | 3 | Ggcagggcaggatataag gc (SEQ ID NO: 40) | Gctctccgtctctaagtggg (SEQ ID NO: 41) | − |
| 1:79977448-79977470 | CATCATCACTGCC CCCACAC TGG (SEQ ID NO: 42) | 3 | Aaggaatgcagatgggctc aa (SEQ ID NO: 43) | Aacaaccatccaactgctc ct (SEQ ID NO: 44) | − |

TABLE 3-continued

Lack of mutation in sgRNA3 and sgRNA4 putative off-target sites

| Locus | Sequence | Mismatch | Forward Primer | Reverse Primer | Mutation |
|---|---|---|---|---|---|
| 4:38051728-38051750 | CCTCATCTCTGCT CGCTCTC TGG (SEQ ID NO: 45) | 3 | Cgtgggaaatggtcaaga acg (SEQ ID NO: 46) | gcttagactcacccacaggt (SEQ ID NO: 47) | — |
| 11:6608878-6608900 | CATCTTCTCTGCC CGCTCTA GGG (SEQ ID NO: 48) | 3 | Agcttctccgaggtccatct (SEQ ID NO: 49) | Ccagcttcaccctaaccca g (SEQ ID NO: 50) | — |
| Original sgRNA4 | CTTTGCCAGCTAC ATCGAGA AGG (SEQ ID NO: 51) | 0 | | | |
| 2:219418816-219418838 | CTTCGCCAACTAC ATCGAGA AGG (SEQ ID NO: 52) | 2 | Cggtgaaccaggagtttct ga (SEQ ID NO: 53) | ctggttagtgagcacctcca c (SEQ ID NO: 54) | — |
| 8:24914126-24914148 | CTTTGCCGGCTA CATAGAGA AGG (SEQ ID NO: 55) | 2 | tcctcctataagcgcagcat (SEQ ID NO: 56) | ctggatctccgcctcaatct (SEQ ID NO: 57) | — |
| 7:157807116-157807138 | CTTTGCCAGCTAC ATCGGAA GGG (SEQ ID NO: 58) | 2 | Ttctgggaggagaggcag aa (SEQ ID NO: 59) | Tcctactctgtctgcccaa (SEQ ID NO: 60) | — |
| 13:102719994-102720016 | CTTTGCTATGTAC ATCGAGA TGG (SEQ ID NO: 61) | 3 | tgggtgggcagatttcccta a (SEQ ID NO: 62) | cagcattaccctgtgtccgtt (SEQ ID NO: 63) | — |
| 12:49295521-49295543 | CTTCGCCAACTTC ATCGAGA AGG (SEQ ID NO: 64) | 3 | Ccacctcataccgccgtac c (SEQ ID NO: 65) | Gttctgctgctccagaaagc (SEQ ID NO: 66) | — |
| 10:113453065-113453087 | CTTTTCCTGCTAT ATCGAGA TGG (SEQ ID NO: 67) | 3 | gaagacactcagccaagg ca (SEQ ID NO: 68) | acccgaaggagttgttcag ag (SEQ ID NO: 69) | — |
| X:27991056-27991078 | ATTAGCCAGCTAC ATGGAGA AGG (SEQ ID NO: 70) | 3 | tgtctgctcatacgttgcacat ta (SEQ ID NO: 71) | Ggcacagagaagtcagct agta (SEQ ID NO: 72) | — |
| 16:51655888-51655910 | CTTTTCCAGCTAC ACTGAGA AGG (SEQ ID NO: 73) | 3 | agaatgtgcctgcccaagtt (SEQ ID NO: 74) | Gggcagtcgtcaaagtca ga (SEQ ID NO: 75) | — |
| 3:123119527-123119549 | CTTTCCCAGCTAC ATAAAGA GGG (SEQ ID NO: 76) | 3 | aaaagtcaggggcgttgtct (SEQ ID NO: 77) | cctgcagagtaagccctag c (SEQ ID NO: 78) | — |
| 20:41999072-41999094 | CTTTGCGGGCTA CATCGACA AGG (SEQ ID NO: 79) | 3 | cgatgtcctcgagcaggtg (SEQ ID NO: 80) | tgctacaacgagcagtgag g (SEQ ID NO: 81) | — |
| 10:17229761-17229783 | CTTCGCCAACTAC ATCGACA AGG (SEQ ID NO: 82) | 3 | cgtgactacgtccacccg (SEQ ID NO: 83) | ctcggccagcaggatcttatt (SEQ ID NO: 84) | — |

Differentiation of Astrocytes from Human IPSCs.

For astrocyte differentiation, human iPSCs (I90, C1, AxD825, AxD999, AxD999-CR) were first differentiated into neural progenitor cells (NPCs) by treating with 10 µM SB434542 (Stemgent), 250 nM LDN-193189 (Stemgent) and 10 µM retinoic acid (RA; Sigma-Aldrich) for 8 days. The differentiation methods are detailed in Table 4.

TABLE 4

Astrocyte differentiation method for each iPSC line

| iPSC line | Differentiation method |
|---|---|
| I90 | Method described herein |
| C1 | Method described herein |
| C3 | Method described previously (Krencik and Zhang, 2011) |
| AxD825 | Method described herein |
| AxD997 | Method described previously (Krencik and Zhang, 2011) |
| AxD999 | Method described herein |
| AxD999-CR | Method described herein |

NPCs were further differentiated by treatment of 10 µM RA and smoothened agonist (SAG; EMD Millipore) for 4 days. Then cells were dissociated using accutase and allowed to form spheres in suspension culture for 8 days, which contains 1×N2 (Life Technologies), 1×B27 (Life Technologies), 10 µM RA and 10 µM SAG. Spheres were attached on Matrigel-coated plates and cultured in PDGF medium containing 1×N2, 1×B27, 10 ng/ml PDGFAA (R&D Systems), 5 ng/ml HGF (R&D Systems), 10 ng/ml IGF-1 (R&D Systems), 10 ng/ml NT3 (EMD Millipore), 100 ng/ml Biotin (Sigma-Aldrich), 60 ng/ml T3 (Sigma-Aldrich), 1 µM cAMP (Sigma-Aldrich) and 25 µg/ml insulin (Sigma-Aldrich). After 10 days of culture, astrocytes migrated out of the spheres were dissociated using Accutase into single cells and seeded into astrocyte medium, containing 1×N2, 1×B27, 10 ng/ml EGF (Peprotech) and 10 ng/ml FGF (Peprotech). These astrocytes were passaged twice a week for another 2 weeks. For final maturation of astrocytes, 10 ng/ml CNTF (R&D Biosciences) was supplemented to medium containing 1×N2 and 1×B27 for 1 week. To show that the relevant cellular phenotypes could be recapitulated in iPSC-derived astrocytes independent of the differentiation protocol, a pair of control and AxD iPSCs (C3 and AxD997) were also differentiated into astrocytes following a previously published protocol (Krencik and Zhang, 2011). Briefly, iPSCs were collected for suspension culture to allow embryo body (EB) formation. EBs were induced to neural lineage by medium supplemented with 1×N2 for 1 week. After 1 week, EBs were attached and rosette-like neuroepithelial structures were able to form within another week. Rosettes were manually blown-off and cultured as spheres in N2 medium supplemented with 10 ng/ml EGF and 10 ng/ml FGF. Spheres were dissociated once a week until day 120 of differentiation. Astrocytes beyond day 120 of differentiation from both protocols were used for experiments.

Differentiation of OPCs and Oligodendrocytes from Human IPSCs.

A previously published protocol (Douvaras and Fossati, 2015) for differentiation of human iPSCs into OPCs and oligodendrocytes was used. Briefly, human iPSCs were signalized and treated with SB434542, LDN-193189 and RA for 8 days. From Day 8 to 12, cells were further induced by RA and smoothened agonist (SAG). After RA and SAG induction, pre-OPCs expressing OLIG2 and NKX2.2 markers were lifted up to form spheres. Pre-OPC spheres were cultured in RA and SAG-supplemented medium for another 8 days, then switched to PDGF medium. 10 Days after switching to PDGF medium, spheres were attached onto Matrigel coated-plates to allow OPCs to migrate out of the spheres and expand. Medium was changed every 2 days. O4$^+$ OPCs could be detected by live staining using O4 antibody around 30 days after sphere attachment. MBP$^+$ mature oligodendrocytes can be generated in another 2 weeks by culturing in maturation medium that has the growth factors, PDGF, IGF, HGF and NT3, withdrawn from the PDGF medium.

Immunohistochemistry.

Cells were fixed with 4% paraformaldehyde (PFA) for 15 min, permeabilized with 0.1% Triton X-100 for 1 hr, and blocked with 5% donkey serum for 1 hr at room temperature (RT). Cells were then incubated with primary antibody diluted in PBS containing 0.1% Triton X-100 and 5% donkey serum and incubated for overnight at 4° C. On the following day, cells were incubated with the relevant secondary antibody diluted at 1:500 in PBS for 1 hr at RT. Cells were counterstained with DAPI before mounting.

For BrdU labeling, OPCs were incubated with 10 µM BrdU for 6 hr, while astrocytes were incubated for 4 hours, and then fixed by 4% PFA for BrdU staining. OPCs were stained with the nucleus marker OLIG2 first. After OLIG2 staining, cells were re-fixed using 4% PFA at RT for 15 min. Cells were then treated with 2 N HCL at 37° C. for 30 min followed by Borate buffer incubation at RT for 15 min. BrdU was stained using anti-BrdU primary antibody and appropriate secondary antibody. Cells were counterstained with DAPI. Antibodies used in this study are listed in Table 5.

TABLE 5

Key Resources

| REAGENT or RESOURCE | SOURCE | IDENTIFIER |
|---|---|---|
| Antibodies | | |
| Rabbit monoclonal anti-NANOG | Cell Signaling | Cat# 4903, RRID: AB_10559205 |
| Mouse monoclonal anti-OCT4 | Santa Cruz | Cat# sc-5279, RRID: AB_628051 |
| Goat polyclonal anti-SOX2 | Santa Cruz | Cat# sc-17320, RRID: AB_2286684 |
| Mouse monoclonal anti-SSEA4 | Santa Cruz | Cat# sc-21704, RRID: AB_628289 |
| Mouse monoclonal IgM anti-Tra-1-60 | Santa Cruz | Cat# sc-21705, RRID: AB_628385 |
| Mouse monoclonal IgM anti-Tra-1-81 | Santa Cruz | Cat# sc-21706, RRID: AB_628386 |
| Rabbit polyclonal anti-GFAP | DAKO | Cat# N1506, RRID: AB_10013482 |
| Mouse monoclonal anti-GFAP | Sigma-Aldrich | Cat# G3893, RRID: AB_477010 |
| Mouse monoclonal anti-human GFAP | Cellartis | Cat# 40420 RRID: N/A |
| Rabbit monoclonal anti-S100 β | Abcam | ab52642, RRID: AB_882426 |
| Mouse polyclonal anti-CRYAB | Enzo Life Sciences | Cat# ADI-SPA-223, RRID: AB_10615646 |
| Goat polyclonal anti-SOX9 | R&D Systems | Cat# AF3075, RRID: AB_2194160 |
| Mouse monoclonal anti-NKX2.2 | DSHB | Cat# 74.5A5, RRID: AB_531794 |
| Rabbit polyclonal anti-OLIG2 | EMD Millipore | Cat#AB9610 RRID: AB_570666 |
| Goat polyclonal anti-OLIG2 | R&D Systems | Cat#AF2418, RRID: AB_2157554 |
| Mouse monoclonal IgM anti-O4 | Sigma-Aldrich | Cat# O7139 RRID: AB_477662 |

TABLE 5-continued

Key Resources

| REAGENT or RESOURCE | SOURCE | IDENTIFIER |
|---|---|---|
| Rat monoclonal anti-MBP | Millipore | Cat# MAB386, RRID: AB_94975 |
| Rat monoclonal anti-BrdU | Accu-Specs | Cat# OBT-0030, RRID: AB_2341179 |
| Rabbit polyclonal anti-cleaved Caspase-3 | Cell Signaling | Cat# 9661, RRID: AB_2341188 |
| Rat monoclonal anti-CD31-PE | BD Biosciences | Cat# 553373, RRID: AB_394819 |
| Rabbit polyclonal anti-FSP1 | EMD Millipore | Cat# ABF32, RRID: AB_11203822 |
| Chicken polyclonal anti-MAP2 | Abcam | Cat# ab5392, RRID: AB_2138153 |
| Rabbit polyclonal anti-CHI3L1 | Abcam | Cat# ab180569 RRID: N/A |
| Goat polyclonal anti-CHI3L1 | R&D Systems | Cat# AF2599, RRID: AB_2291883 |
| Sheep polyclonal anti-TMEM219 | R&D Systems | Cat# AF7556 RRID: N/A |
| Rabbit polyclonal anti-CRTH2 | Invitrogen | Cat# PA5-34502, RRID: AB_2551854 |
| Bacterial and Virus Strains | | |
| hGFAP-GFP | This paper | N/A |
| Biological Samples | | |
| Postmortem human brain frontal cortex | NIH NeuroBiobank | RRID: SCR_003131 |
| Chemicals, Peptides, and Recombinant Proteins | | |
| Matrigel | Corning | Cat# CB40230 |
| mTeSR1 | Stem Cell Technologies | Cat# 85850 |
| Rocki Y-27632 | Reprocell | Cat# 04-0012-10 |
| Accutase | Sigma-Aldrich | Cat# A6964 |
| SB431542 | Stemgent | Cat# 04-0010 |
| LDN-193189 | Stemgent | Cat#04-0074 |
| Smoothened agonist (SAG) | EMD Millipore | Cat#566660 |
| bFGF | PeproTech | Cat# 100-18B |
| EGF | PeproTech | Cat#100-15 |
| Retinoic acid | Sigma-Aldrich | Cat#R2625 |
| N2 | Life Technologies | Cat# 17502048 |
| B27 | Life Technologies | Cat# 12587010 |
| CNTF | R&D systems | Cat# 257-NT-050 |
| PDGFAA | R&D systems | Cat# 221-AA-050 |
| IGF-1 | R&D systems | Cat#291-G1-200 |
| HGF | R&D systems | Cat#294-HG-025 |
| NT3 | EMD Millipore | Cat# GF031 |
| 3,3',5-Triiodo-L-thyronine (T3) | Sigma-Aldrich | Cat# T2877 |
| Biotin | Sigma-Aldrich | Cat#4639 |
| cAMP | Sigma-Aldrich | Cat# D0260 |
| L-Ascorbic acid | Sigma-Aldrich | Cat# A4403 |
| Insulin | Sigma-Aldrich | Cat#I9278 |
| BrdU | Sigma-Aldrich | Cat#B5002 |
| Fluo-4-AM | Invitrogen | Cat# F14201 |
| Critical Commercial Assays | | |
| Tetro cDNA Synthesis kit | BioLINE | Cat#Bio-65043 |
| SYBR Green Master Mix | Thermo Scientific | Cat#F416L |
| P3 4D nucleofection kit | Lonza | Cat# V4XP-3024 |
| Deposited Data | | |
| RNA-seq data | This paper | |
| Experimental Models: Cell Lines | | |
| I90 fibroblast | Coriell | Cat#IMR90 RRID: CVCL_0347 |
| C1 fibroblast | ATCC | Cat# CRL-2097 RRID: CVCL_2337 |
| C3 fibroblast | Wen et al., 2014b | N/A |
| AxD825 fibroblast | Coriell | Cat# GM16825 RRID: CVCL_U890 |
| AxD997 fibroblast | Telethon network | Cat# FFF0211997 |
| AxD999 fibroblast | Telethon network | Cat# FFF0211999 |
| Human primary astrocytes | ScienCell | Cat# 1800 |
| Experimental Models: Organisms/Strains | | |
| NSG mice | The Jackson Laboratory | Cat#005557 RRID: IMSR_JAX:005557 |
| Rag2−/− mice | The Jackson Laboratory | Cat#008449 RRID: IMSR_JAX:008449 |
| Oligonucleotides | | |
| See Table 1 for details | | |
| Recombinant DNA | | |
| pSpCas9n (BB)-2A-GFP | Ran et al., 2013b | #48140 |
| pCXLE-hSK | Addgene | #27078 |
| pCXLE-hUL | Addgene | #27080 |
| pCXLE-hOCT3/4-shp53-F | Addgene | #27077 |
| pCXWB-EBNA1 | Addgene | #37624 |
| Software and Algorithms | | |
| Zen 2.3 | Carl Zeiss | N/A |
| Image Pro Premier 9.3 | Media Cybernetics | N/A |
| GraphPad Prism 7.01 | GraphPad Software | RRID: SCR_002798 |

Lentiviral Preparation and Transduction.

The pHIV-hGFAP-GFP lentiviral vector was prepared by cloning the hGFAP-GFP fragment from the hGFAP-GFP vector (Addgene, plasmid #40592) into the pHIV vector. Lentiviruses were prepared as previously described (Shi et al., 2004; Qu et al., 2010). To transduce astrocytes, cells were seeded onto Matrigel-coated plates for overnight and then transduced with the pHIV-hGFAP-GFP lentivirus supplemented with 4 μg/ml polybrene (AmericanBio) for 24 hr. Virus-containing medium was replaced with fresh astrocyte culture medium 24 hr later.

Cell Sorting.

The pHIV-hGFAP-GFP lentivirus-transduced astrocytes were sorted using ARIA SOPR cell sorter (BD Bioscience) at the Analytical Cytometry Core at City of Hope. Astrocytes without viral transduction were used as the negative control. The GFP$^+$ cells were collected into astrocyte culture medium and propagated for experiments. The O4$^+$ OPCs were sorted using magnetic-activated cell sorting (MACS) following manufacturer's (Miltenyi Biotech) instruction. The OPC differentiation product was dissociated into single cells using Accutase. These cells were incubated with O4-microbeads at 4° C. for 15 min, protected from light. Cell suspension was loaded onto LS Magnetic Column (Miltenyi Biotech) placed in the field of a magnetic MACS Separator. The O4⁻ cells were washed off, while the O4⁺ OPCs were retained, followed by elution into collection tube. The O4⁺ OPCs were counted using hemacytometer and used for astrocyte co-culture experiments.

Calcium Imaging.

Cells were matured in CNTF medium on Matrigel-coated iBibi 8-well chamber slides for at least 5 days before imaging. 2 µM Fluo-4 AM (Invitrogen) was loaded onto cells for 15 minutes and then washed 3 times with PBS. 0.4 ml culture medium was added per chamber to replace PBS. 3 minutes later, cells were imaged at 0.7 s intervals using 20× objective of Zeiss Observer Z1 microscope with heat and $CO_2$ controlled live imaging chamber. For the pharmacological experiment, ATP (3 µM) was applied at around 50 seconds after starting recording. To quantify the percentage of cells responding to ATP stimulation, fluorescence levels were quantified using ImagePro software. The change of fluorescence level over time is defined as $\Delta F/F=(F-F0)/F0$, where F is the fluorescence intensity at any time point, and F0 is the baseline fluorescence intensity averaged across the whole movie for each cell. Cells with $\Delta F/F>0.05$ were counted as responsive. Intensity traces of cells were extracted using ImagePro 9.0 (Media Cybernetics) and used to calculate and graph the fluctuations of $Ca^{2+}$ intensity.

Electrophysiology.

Cells were plated in 3.5 mm dishes coated with Matrigel and were analyzed by whole-cell patch clamp recording. Whole-cell patch clamp recording was performed with a voltage clamp at −70 mV and stepped from −50 mV to +50 mV at 10 mV increments for duration of 500 ms. Cells were bathed in Hank's buffered Saline solution (140 mM NaCl, 3 mM KCl, 2 mM $CaCl_2$, 1 mM $MgCl_2$, 15 mM HEPES and 23 mM glucose, pH of 7.35-7.45). Glass pipettes were back filled with intracellular solution (145 mM KCl, 10 mM NaCl, 1 mM EGTA, 1 mM $MgCl_2$, 10 mM HEPEs, pH of 7.35-7.45). Osmolality for both solutions was 300±10 milliosmole (mOsm).

Astrocyte Transplantation.

Human iPSC-derived AxD999 astrocytes purified using GFAP-GFP-based FACS were resuspended in astrocyte medium at 100,000 cells/µl. 200,000 cells were injected at 1 mm from the midline between the Bregma and Lambda and 1 mm deep into the anterior lateral ventricles of P2-P4 $Rag2^{-/-}$ mice. The transplanted mice were perfused with 4% PFA 1 month after transplantation. Brains were harvested, embedded in OCT and sectioned at 30 µm thickness. Brain sections were immunostained for human GFAP (hGFAP) and imaged for both hGFAP signal and GFAP-GFP fluorescence.

Astrocyte-OPC Co-Culture.

Astrocytes were seeded at the density of $5\times10^4$ cells per well in Matrigel-coated 24-well plates and induced for maturation by 10 ng/ml CNTF for 5-7 days. The O4⁺ OPCs sorted by MACS were plated onto astrocyte cultures at $5\times10^3$ cells per well. Co-cultured cells were maintained in PDGF medium. For O4 and OLIG2 quantification assays, OPCs were co-cultured with astrocytes for 5 days. On Day 5 of co-culture, cells were fixed and stained as described in the Immunohistochemistry section. For BrdU labeling assay and apoptosis assay, OPCs were co-cultured with astrocytes for 1 day. On Day 2 of co-culture, cells were stained for cleaved Caspase-3 and OLIG2 or BrdU and OLIG2. Images were taken using Zeiss Observer or Nikon ECLIPSE TE2000-S. A minimum of 5 images per well were taken for cell number quantifications.

3D Nanofiber Myelination Assay.

Eight-chamber slides aligned with 700 nm diameter electrospun polycaprolactone (PCL) nanofibers were purchased from Nanofiber Solutions. 1:100 diluted Matrigel was used to coat nanofibers at 37° C. for 3 days. Astrocytes were seeded at 5×104 cells per chamber and induced for maturation by 10 ng/ml CNTF for 5 days. Then the O4⁺ OPCs sorted by MACS were seeded at $8\times10^4$ cells per chamber. Cells were cultured in OPC medium for 5 days with medium change daily and switched to maturation medium to allow OPC maturation for 2 weeks with medium change every 2 days. After 2 weeks of maturation, cells were fixed with 4% PFA and stained as described in the Immunohistochemistry section. Images were taken using Zeiss Confocal 700. A minimum of 5 images per well were taken for quantification of MBP⁺ cell number and MBP⁺ area. MBP⁺ area and segment length were analyzed by polygon or line drawing using ImagePro. For high resolution images, OPCs were plated on 2 µM aligned nanofibers (MIMETIX, Electrospinning Company) as described above and imaged using Zeiss Confocal 880 with Airyscan. 3D images were generated using Zen Blue edition.

RNA-Seq.

RNA isolation from fixed, GFAP⁺ sorted astrocytes was performed following a previously published protocol (Hrvatin et al., 2014). Briefly, the astrocytes were fixed and stained with GFAP antibody and appropriate secondary antibody. Then the GFAP⁺ cells were sorted under sterile conditions and collected for RNA isolation. RNase inhibitor was added into staining and sorting buffers to minimize RNA degradation during the procedure. RNA was isolated from the sorted cells using the RecoverAll Total Nucleic Acid Isolation kit (Ambion). RNA quality control and subsequent library construction and poly (A) RNA-seq were performed by the Integrative Genomics Core at City of Hope. RNA-Seq reads were aligned against the human genome (hg19) using TopHat2 (version 2.0.14, (Kim et al., 2013)). Read counts were quantified using htseq-count (version 0.6.0) (Anders et al., 2015) with UCSC known gene annotations (TxDb. Hsapiens.UCSC. hg19.knownGene, downloaded Jun. 8, 2016) (Hsu et al., 2006). Aligned reads were counted using GenomicRanges (Lawrence et al., 2013). Genes were filtered to only include transcripts with RPKM values greater than 0.1 (after a rounded log 2-transformation) in at least 50% of samples. Genes smaller than 150 bp were removed prior to differential expression analysis. $Log_2(RPKM+0.1)$ expression values were used for visualization and fold-change calculations. Separate comparisons were performed for the 4 astrocyte lines and the 8 brain samples (AxD vs. control). A 1-variable model was used for the tissue comparison and a 2-variable model (adjusting for differentiation method) was used for astrocyte comparison. To determine genes with varied expression between control and AxD in both astrocytes and brain tissue (n=12), a 2-variable model in DESeq2 was used. P values were calculated using DESeq2 (Love et al., 2014), which were used to calculate the False Discovery Rate (FDR) (Benjamini and Hochberg, 1995). Differentially expressed genes (DEG) were defined as FDR<0.05 and absolute value of fold change >1.5. The venn diagram was produced using the Vennerable package (version 3.0) in R. Gene Ontology (GO) (Ashbumer et al., 2000) enrichment was performed using goseq (Young et al., 2010). Representative genes of each function type were selected based on their functional relevance through literature search and |fold-change|>1.5. Heatmaps were generated by the gplots package (version 3.0.1). While the 2-variable n=4 astrocyte comparison using DESeq2 did not strictly identify CHI3L1, it could be identified using both a 1-variable n=4 astrocyte comparison and an n=8 brain tissue comparison using edgeR (McCarthy et al., 2012), consistent with CHI3L1 as the top DEG in n=12 comparison using DESeq2.

Human Post-mortem Tissue Processing.

Fixed and frozen brain tissues from post-mortem AxD patients and healthy control individuals were obtained from NIH Neurobiobank (RRID:SCR_003131). The evaluation from Institutional Review Board determined these coded tissues without identifiers from deceased subjects do not meet the definition of human subject research. RNAs from frozen brain tissues were isolated using Trizol (Ambion) as previously described (Cui et al., 2016; Cui et al., 2017). Quality control of RNAs, library construction and poly(A) RNA-seq were performed by the Integrative Genomics Core at City of Hope. Data analysis was performed as described above.

qRT-PCR.

Total RNA was extracted using Trizol (Ambion) as previously described (Cui et al., 2016; Cui et al., 2017). Complementary DNA was reverse transcribed from 1 μg total RNA using Tetro cDNA Synthesis kit (BioLINE). Primer sequences are listed in Table 1.

qRT-PCR was performed using SYBR Green Master Mix (Thermo Scientific) on the Step One Plus Real-Time PCR Instrument (Applied Biosystems). ACTIN or GAPDH was used as the reference gene. Each reaction was run in triplicate. Data was analyzed using ΔΔCt method and normalized to control group in each run.

Western Blot.

Cell lysates were extracted using Pierce RIPA buffer (Thermo Scientific). Protein concentration was measured using BCA assay kit (Thermo Scientific). 40 μg proteins for CHI3L1 and 30 μg proteins for MBP were loaded for Western blot. Western blot membranes were developed using ECL Select kit (GE Healthcare) and imaged using ChemiDoc Imaging System (Bio-Rad).

Conditioned Medium Preparation and Neutralizing Antibody Treatment.

AxD999 astrocytes were seeded at 1 million cells/well in a Matrigel-coated 6-well plate. Cells were conditioned in PDGF medium for 24 or 48 hours. Conditioned medium was collected and centrifuged at 200×g for 10 minutes and supernatant was filtered through 0.22 μm filter to eliminate cells and cell debris. The O4$^+$ OPCs were sorted using MACS and eluted with AxD999 conditioned medium. 5,000 OPCs were seeded onto AxD999-CR astrocytes and cultured in AxD999 conditioned medium supplemented with 10 μg/ml neutralizing antibody or corresponding control IgG for 24 hr.

shRNA Preparation and CHI3L1 Knockdown.

shRNAs were cloned into the lentiviral PGK-puro vector. The following shRNA sequences were used: control shRNA, 5'-TCTACTGTCACTCAGTACC-3' (SEQ ID NO:85); CHI3L1 shRNA-1, 5'-ATGCAGAGCAGCACTGGAGC-3' (SEQ ID NO:86); CHI3L1 shRNA-2, 5'-ATGGCGGTACTGACTTGATG-3' (SEQ ID NO:87). 5 μg shRNAs were transfected into astrocytes using Lipofectmin 3000 following manufacturer's instruction (Life Technologies) for co-culture assays that were less than 5 days. For myelination assay that needs co-culture for more than 5 days, shRNA lentiviruses were used to infect astrocytes at MOI of 1.

Mouse OPC Isolation.

Neonatal Rag2$^{-/-}$ mice were euthanized and brain tissues were harvested immediately. Brains were dissociated into single cells using Neural Tissue Dissociation Kit (P) (Miltenyi Biotech) and gentleMACS Octo Dissociator with Heaters (Miltenyi Biotech) following manufacturer's instructions. Singlized cells were incubated with O4 antibody-conjugated microbeads and sorted with MACS as described above. O4$^+$ OPCs were collected for RNA isolation, cDNA synthesis and CRTH2 qRT-PCR analysis.

*Mycoplasma* Test.

All cell culture samples were monitored by *mycoplasma* test at least once a month using MycoAlert™ PLUS *Mycoplasma* Detection Kit (Lonza). 500 μl culture medium was harvested and centrifuged at 200×g for 5 minutes to eliminate cell debris. 100 μl medium was taken for 2 reactions with reagents provided in the kit. The result was determined by luminescence reading according to the protocol. All cellular samples used in this study are *mycoplasma*-negative.

Quantification and Statistical Analysis.

Statistical significance was analyzed using Graphpad Prism Version 7.01 by one-tailed Student's t-test or non-paired One-way ANOVA as reported in each figure legend. When comparing two experimental groups, unpaired Student's t test was used. When comparing multiple experimental groups, data was analyzed using one-way ANOVA, followed by Tukey's post hoc test when ANOVA has p<0.05. For all tests, p values were presented as *p<0.05, p<0.01, and *p<0.001. Error bar stands for SD if not stated otherwise. Statistical details of each experiment can be found in the figure legends.

Data and Software Availability.

The accession number of RNA-seq data reported in this document is GSE116327.

Example 2: GFAP-Mutant AxD IPSCs can be Differentiated into Astrocytes

Figure 1D:
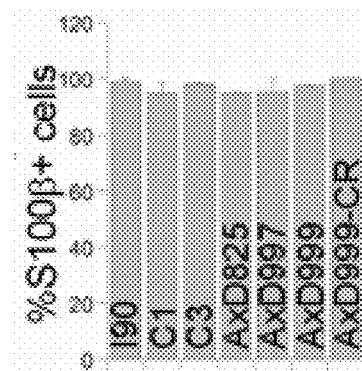
Figure 2A:
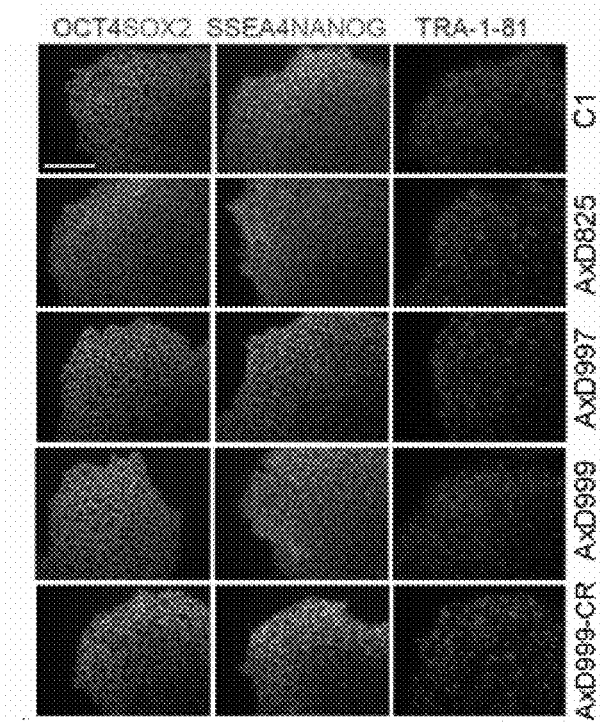
FIGS. 2A-2F show characterization of healthy control and AxD iPSCs and isogenic iPSCs.
Figure 2B:
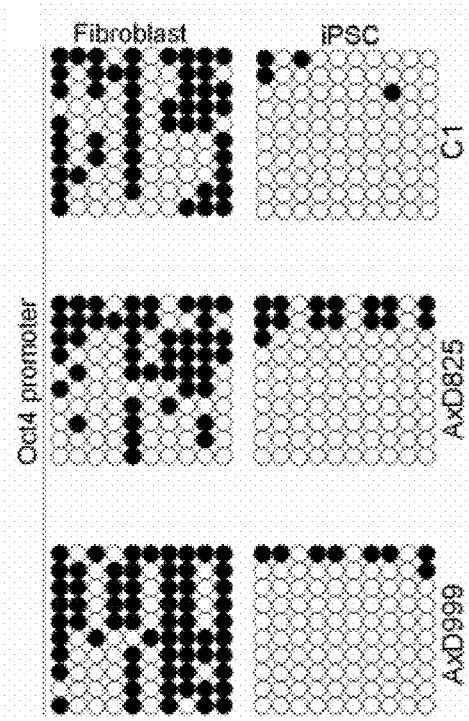
Figure 2C:
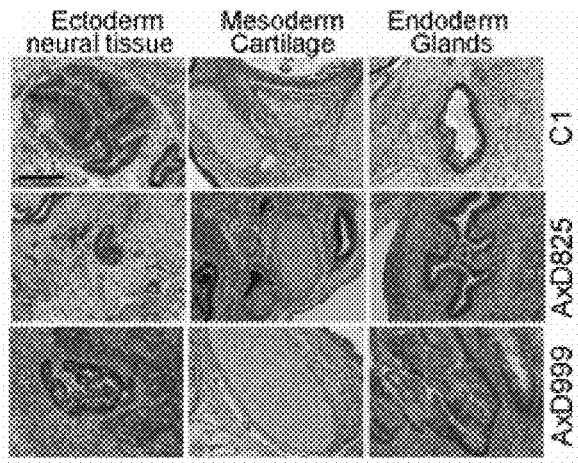
Figure 2D:
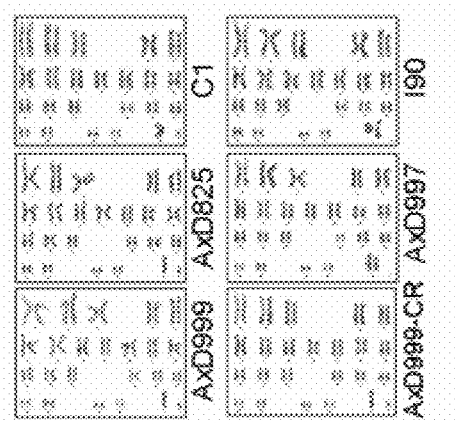
Figure 2E:
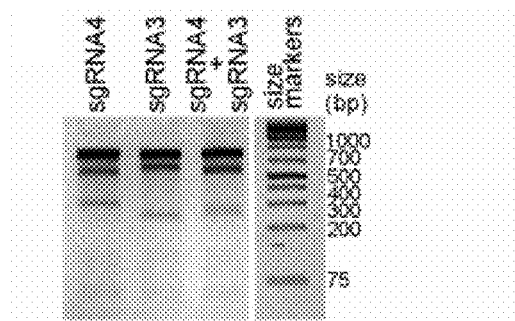
Figure 2F:
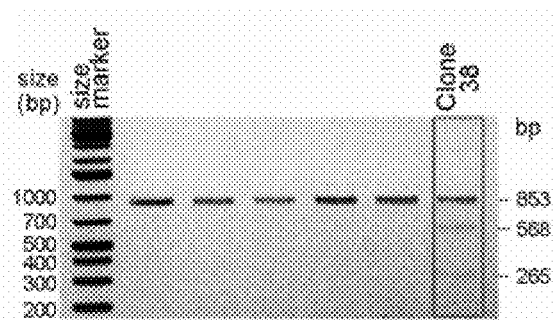

To study the pathological effects of AxD GFAP mutations in a human cellular model, human iPSCs from fibroblasts of three healthy control (HC) individuals (C1, C3 and I90) and three AxD patients (FIG. 1A) were generated through episomal reprogramming (Wen et al., 2014a; Kime et al., 2015). Among the three AxD patients, two carried hot spot GFAP mutations at either Arg (R) 79 or R239 (Hagemann et al., 2006), including an R79C (AxD997) and an R239C mutation (AxD825), and another had a M73K mutation (AxD999) in the GFAP coding region (FIG. 1B). To identify true GFAP mutation-relevant phenotypes independent of line-to-line variation, isogenic iPSCs were generated by correcting the GFAP mutation site (M73K) in AxD999 iPSCs using the CRISPR/Cas9 nickase (Ran et al., 2013a) (FIG. 1C; FIGS. 2E and 2F). Correction of the M73K mutation site in the selected clone was confirmed by Sanger sequencing of the GFAP gene (FIG. 1C). This CRISPR/Cas9-edited AxD999 clone containing the WT GFAP gene was termed AxD999-CR. No off-target effect was detected in the AxD999-CR iPSCs during CRISPR/Cas9 editing (Table 3). All iPSC lines were characterized for pluripotency and normal karyotype (FIG. 2), and authenticated by Short Tandem Repeat (STR) assay (Table 6).

TABLE 6

STR analysis of healthy control, AxD, and isogenic iPSCs

| Locus/Cell line | I90 Fib | I90 iPSC | C1 Fib | C1 iPSC | AxD825 Fib | AxD825 iPSC | AxD997 Fib | AxD997 iPSC | AxD999 Fib | AxD999 iPSC | AxD999 CR-iPSC |
|---|---|---|---|---|---|---|---|---|---|---|---|
| AMEL | X | X | X, Y | X, Y | X, Y | X, Y | X, X | X, X | X, Y | X, Y | X, Y |
| CSF1PO | 11, 13 | 11, 13 | 12, 13 | 12, 13 | 10, 12 | 10, 12 | 11 | 11 | 12, 13 | 12, 13 | 12, 13 |
| D13S317 | 11, 13 | 11, 13 | 11, 12 | 11, 12 | 12, 14 | 12, 14 | 12 | 12 | 11 | 11 | 11 |
| D16S539 | 10, 13 | 10, 13 | 9, 11 | 9, 11 | 9, 11 | 9, 11 | 12 | 12 | 9, 12 | 9, 12 | 9, 12 |
| D21S11 | 30.2, 31 | 30.2, 31 | 29, 31.2 | 29, 31.2 | 30, 32.2 | 30, 32.2 | 30, 31 | 30, 31 | 27, 31 | 27, 31 | 27, 31 |
| D5S818 | 12, 13 | 12, 13 | 11, 12 | 11, 12 | 11, 12 | 11, 12 | 11 | 11 | 10, 11 | 10, 11 | 10, 11 |
| D7S820 | 9, 12 | 9, 12 | 12 | 12 | 11, 12 | 11, 12 | 10, 11 | 10, 11 | 10, 11 | 10, 11 | 10, 11 |
| TH01 | 8, 9.3 | 8, 9.3 | 6, 9.3 | 6, 9.3 | 7, 9.3 | 7, 9.3 | 9, 9.3 | 9, 9.3 | 7, 8 | 7, 8 | 7, 8 |
| TPDX | 8, 9 | 8, 9 | 10, 11 | 10, 11 | 9 | 9 | 8 | 8 | 8 | 8 | 8 |
| vWA | 16, 19 | 16, 19 | 17, 18 | 17, 18 | 17 | 17 | 14, 17 | 14, 17 | 13, 14 | 13, 14 | 13, 14 |

Figure 1E:
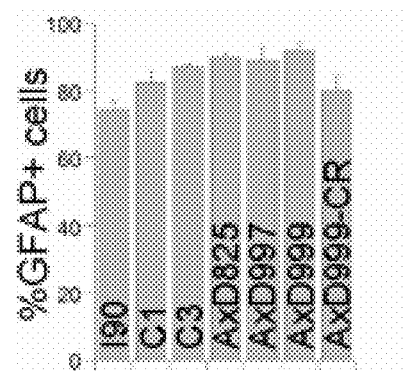
Figure 1F:
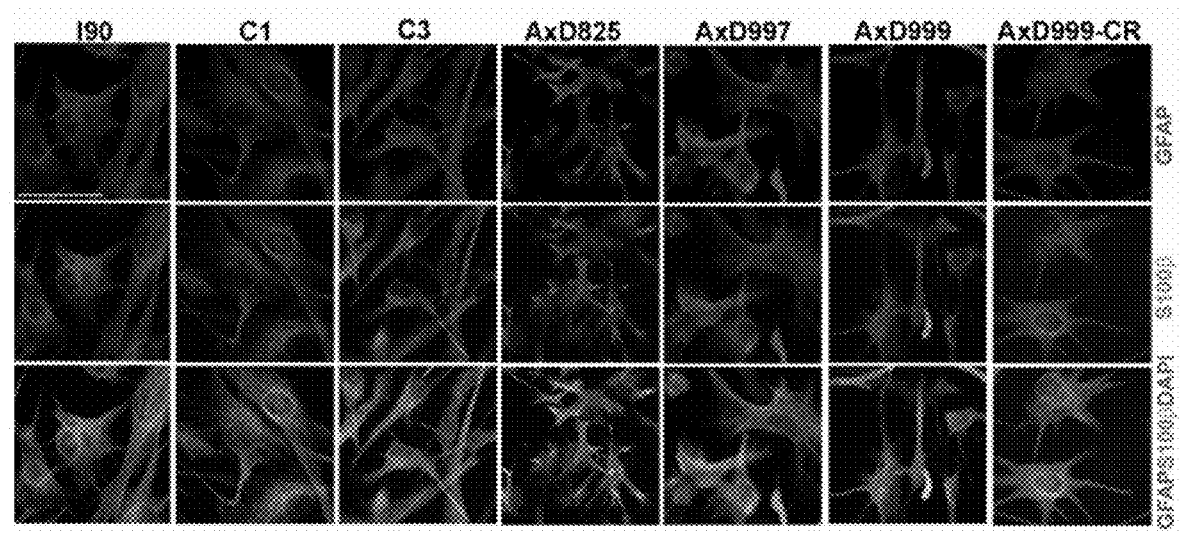
Figure 3E:
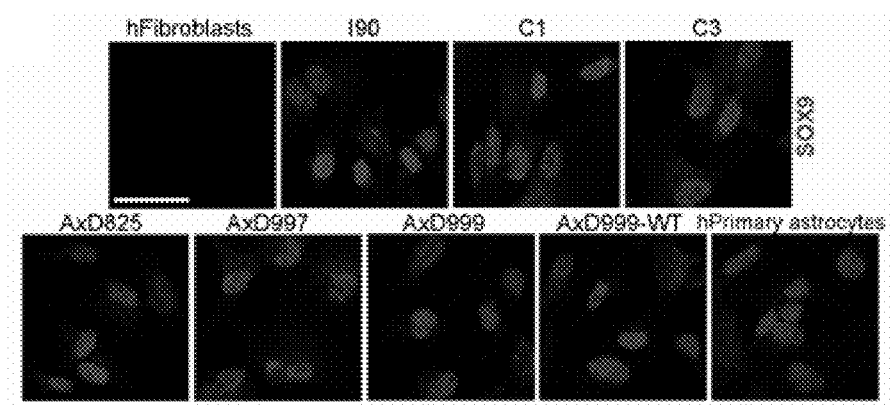

Because GFAP is predominantly expressed in astrocytes, to investigate the effect of the AxD GFAP mutations on astrocyte function, control and AxD iPSCs were differentiated into astrocytes. To achieve consistency in astrocyte purity across lines, the iPSC-derived astrocytes were transduced with lentivirus encoding the human GFAP-promoter-driven-GFP (GFAP-GFP) reporter. Human primary astrocytes and fibroblasts were included as the positive and negative control, respectively (FIGS. 3A-3C). The GFAP-GFP-positive iPSC-derived astrocytes were sorted by fluorescence-activated cell sorting (FACS) (FIG. 3D). The sorted astrocytes expressed the astrocyte markers GFAP and S100β (FIGS. 1D-1F). The purity of the sorted astrocytes was consistent across all lines based on the percentage of the GFAP$^+$ cells and the S100β$^+$ cells after sorting (FIGS. 1D, 1E). The human iPSC-derived astrocytes expressed other astrocyte markers, such as SOX9 (FIG. 3E) (Zhang et al., 2016), CD44, GLUL and SCL1A3 as well (Table 7).

TABLE 7

$Log_2(RPKM + 0.1)$ values of lineage-specific genes in iPSC-derived astrocytes

| Lineage | Gene Symbol | I90 AS | C3 AS | AxD999 AS | AxD997 AS | p value |
|---|---|---|---|---|---|---|
| Astrocyte | CD44 | 5.350800163953 | | 8.314970 | 7.294740 | 0.265 |
| | GFAP | 6.687800512192 | | 4.801919 | 9.624032 | 0.981 |
| | GLUL | 6.095403 | 568787 | 5.01315 | 6.204961 | 0.82 |
| | S100β | 2.886595553431 | | 5.513476 | 7.404027 | 0.00014 |
| | SLC1A3 | 7.107960237518 | | 6.492533 | 8.624115 | 0.684 |
| | SOX9 | 6.177605094433 | | 6.232266 | 6.152501 | 0.596 |
| Endothelial | ESAM | −1.9491850396 | | −1.84123 | −1.73102 | 0.908 |
| | ITM2A | −3.32192335506 | | −3.32193 | −3.32193 | 0.515 |
| | PECAM1 | −3.1279332193 | | −3.32193 | −3.22044 | 0.844 |
| Fibroblast | CXCL1 | −3.3219300600 | | −3.32193 | −2.973631 | 0.993 |
| Microglia | C1QA | −3.3219332193 | | −3.32193 | −3.32193 | N/D |
| | CCL3 | −3.3219332193 | | −3.32193 | −3.32193 | N/D |
| | CLDN5 | −3.3212399983 | | −3.12427 | −2.55533 | 0.743 |
| | CX3CR1 | −3.3219301286 | | −3.19364 | −3.19915 | 0.931 |
| Neuron | RBFOX3 | −3.22518227186 | | −3.32193 | −0.97872 | 0.471 |
| | SLC17A7 | −2.55560351284 | | −3.13908 | −2.34522 | 0.776 |
| | STMN2 | −0.1708615665 | | −1.09374 | 2.057185 | 0.333 |
| | SYN1 | −0.2838994769 | | −0.28211 | −1.41902 | 0.757 |
| Oligodendrocyte | MBP | −3.2692706149 | | −2.91988 | −1.29702 | 0.263 |
| | MOG | −3.1476101949 | | −3.32193 | −3.32193 | 0.53 |
| | SOX10 | −2.49173332193 | | −3.32193 | −3.32193 | 0.508 |

AS: astrocytes;

RBFOX3: gene name for NEUN;

PECAM1: gene name for CD31;

CXCL1: gene name for FSP.

N/D: could not be determined because all values in comparison are the same.

These astrocytes also expressed many mature astrocyte markers described in published studies (Hasel et al., 2017; Sloan et al., 2017) (Table 8).

4D), similar to the pattern of astrocytes shown previously (Krencik et al., 2011). These astrocytes were used for the following studies.

TABLE 8

Log$_2$(RPKM + 0.1) values of mature astrocyte genes in iPSC-derived astrocytes

| Gene symbol | I90 AS | C3 AS | AxD999 AS | AxD997 AS | p value |
|---|---|---|---|---|---|
| ABAT | 5.551028196 | 4.384005282 | 4.803316924 | 5.633997001 | 0.807 |
| AGT | 3.666307759 | 0.020763001 | −2.108777465 | 3.554414654 | 0.859 |
| AHNAK | 2.437167 | 4.939076 | 4.221318102 | 3.52869525 | 0.982 |
| ALDH1L1 | −1.909906926 | −2.252077043 | −2.818140835 | −3.321928095 | 0.231 |
| ALDOA | 6.979383912 | 6.565043243 | 7.190025444 | 6.573783966 | 0.949 |
| APOE | 5.460536 | 3.17041 | 1.774501566 | 3.24890166 | 0.0657 |
| BAG3 | 3.639562 | 4.965638 | 4.603141441 | 4.28825082 | 0.953 |
| BHLHE40 | 3.842331 | 3.160633 | 3.198509463 | 3.9531681 | 0.987 |
| CD44 | 5.350801 | 7.763953 | 8.314969997 | 7.29474003 | 0.265 |
| CDKN1A | 3.530485 | 6.705706 | 5.784334868 | 6.0748798 | 0.533 |
| CHPF | 5.446456 | 5.748054 | 5.044504436 | 5.55223196 | 0.354 |
| CRYAB | 4.148836 | 6.489178 | 5.134219413 | 2.01264948 | 0.251 |
| CTSB | 4.403378 | 4.877515 | 4.612283816 | 5.74194256 | 0.3 |
| CTSD | 5.48926 | 6.289115 | 5.534094053 | 6.46415834 | 0.951 |
| CTSF | 2.293445 | −3.32193 | 3.432017877 | 0.5153734 | 0.238 |
| CTSL | 2.59289 | 3.262361 | 3.111112194 | 3.61925637 | 0.51 |
| CYSTM1 | 2.909659 | 3.057984 | 3.989643503 | 3.11467727 | 0.421 |
| DKK3 | 6.295215 | 7.293231 | 7.273419049 | 7.44918233 | 0.327 |
| EPHX1 | 4.371641 | 4.995437 | 4.03222406 | 4.50822621 | 0.266 |
| FHL1 | 5.071238 | 4.646417 | 4.704460068 | 4.80940521 | 0.668 |
| FTL | 7.201918 | 6.92224 | 6.047047184 | 7.81990983 | 0.788 |
| GADD45B | 1.17609 | 2.147137 | 0.884210612 | 1.15200489 | 0.353 |
| GLUD1 | 5.451744747 | 4.034109586 | 5.029399788 | 5.375966688 | 0.563 |
| GLUL | 6.095403046 | 4.568786601 | 5.013149845 | 6.204961252 | 0.82 |
| GLUT1 | 5.119937834 | 3.422787185 | 4.638306863 | 4.899002268 | 0.561 |
| GPI | 4.556996081 | 3.687056683 | 4.273997041 | 3.83627238 | 0.717 |
| GPRC5B | 4.844104 | 5.298995 | 5.433115057 | 6.05026042 | 0.156 |
| HK1 | 5.719634357 | 6.243858607 | 5.750926959 | 5.50755595 | 0.359 |
| IDS | 5.042735 | 5.615334 | 5.711137636 | 5.57971578 | 0.624 |
| ITPKB | 4.870909 | 3.504409 | 2.874253297 | 4.25882509 | 0.367 |
| LRP1 | 2.093424 | 5.039095 | 3.781469215 | 4.32977652 | 0.719 |
| LYST | 0.92244 | 1.258892 | 1.671796364 | 0.94873418 | 0.792 |
| NRP2 | 5.135993 | 6.141224 | 5.534349036 | 3.56866998 | 0.195 |
| NTRK2 | 4.813651 | 1.735164 | 3.724078737 | 2.82603976 | 0.775 |
| PGAM1 | 2.610905447 | 2.999187766 | 3.01382696 | 2.483320341 | 0.823 |
| PGK1 | 6.091445762 | 6.02023484 | 5.935711455 | 5.659408688 | 0.416 |
| PLTP | 5.036486 | 5.309077 | 5.337250526 | 5.58456148 | 0.628 |
| PRNP | 4.295787 | 5.321347 | 4.979124322 | 5.62628731 | 0.362 |
| PSAP | 8.092047 | 8.552547 | 8.447155871 | 8.67715445 | 0.709 |
| RNF19A | 5.846252 | 3.840852 | 4.303687792 | 5.19789715 | 0.771 |
| SCG2 | 6.377105019 | 8.097510937 | 7.876265924 | 7.338011854 | 0.735 |
| SERPINE2 | 4.116384 | 2.768287 | 4.066220964 | 3.6996154 | 0.51 |
| SLC4A4 | 2.760230329 | 0.05013865 | −0.487721313 | 2.010391208 | 0.577 |
| SPATS2L | 3.451014 | 3.903462 | 4.409502074 | 4.67825954 | 0.0643 |
| SQSTM1 | 4.099362 | 4.382815 | 4.285886838 | 4.86715482 | 0.547 |
| TMEM47 | 3.174792 | 3.617841 | 3.005599137 | 3.14225646 | 0.381 |
| TPI1 | 6.060954432 | 6.308243947 | 6.406077498 | 6.030460498 | 0.914 |
| TPP1 | 4.347616 | 5.81643 | 4.820031613 | 6.07925793 | 0.512 |
| UBC | 5.854919 | 6.484975 | 6.848196648 | 6.6630853 | 0.306 |
| UNC5B | 2.968453 | 5.070248 | 3.640793297 | 1.72867688 | 0.188 |
| VAT1 | 5.249779 | 5.766875 | 5.318025564 | 6.20469988 | 0.686 |

Figure 4A:
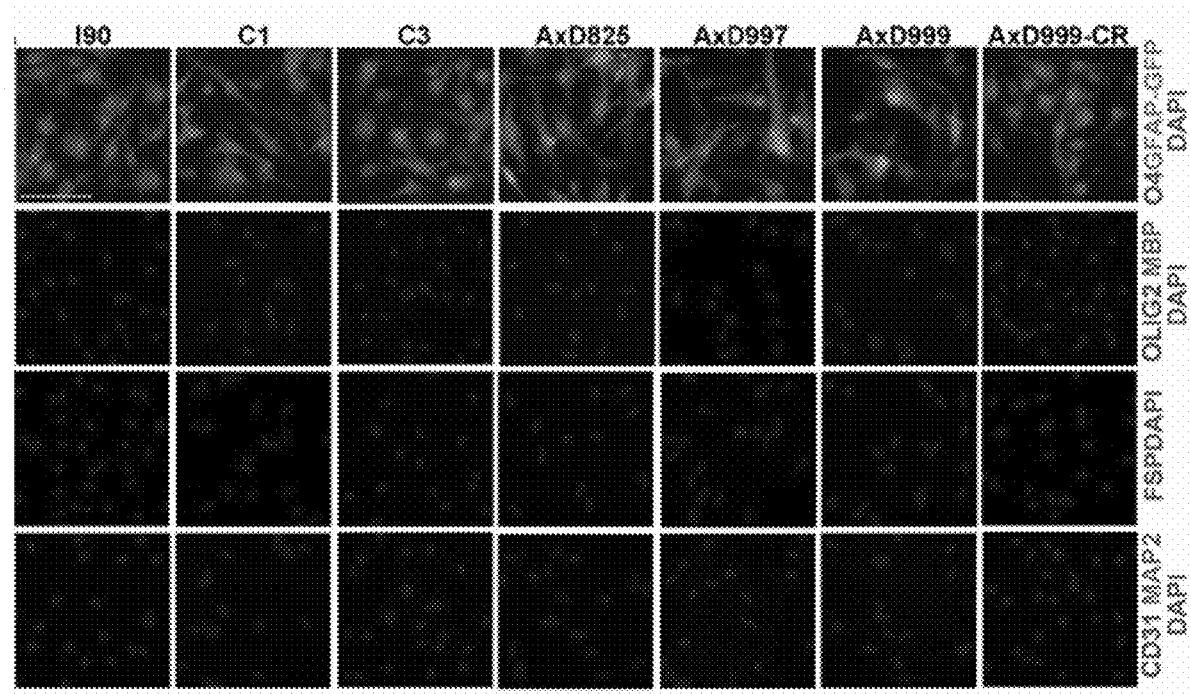
FIG. 4A-4D show that purified astrocytes were not contaminated by other lineage cells and were functional.
Figure 4B:
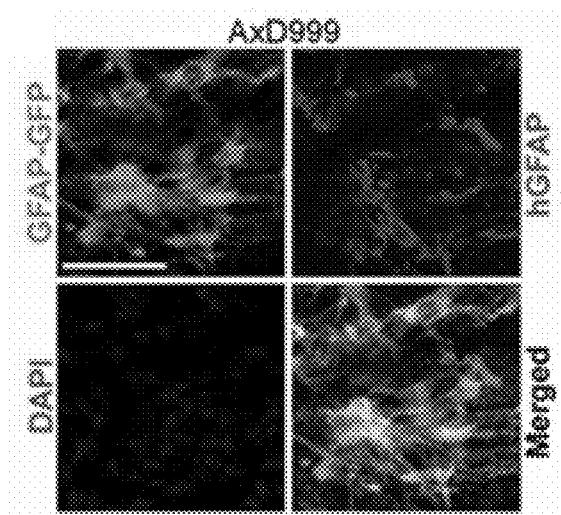
Figure 4C:
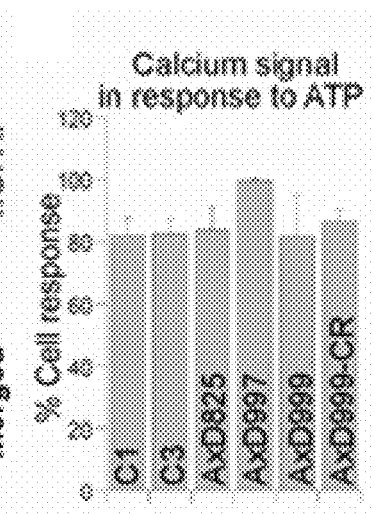
Figure 4D:
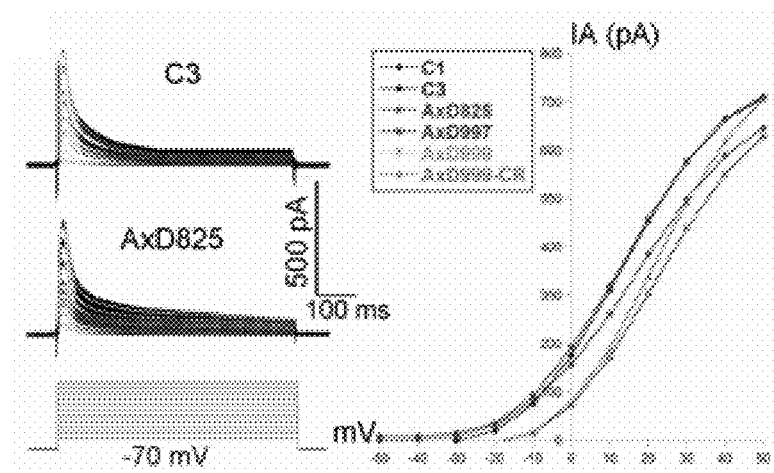

The iPSC-derived astrocytes were not contaminated by oligodendrocyte lineage cells, neurons, endothelial cells and fibroblasts, as revealed by negative staining of the oligodendrocyte lineage markers, OLIG2, O4 and MBP, and the other lineage-specific markers, MAP2, CD31 and FSP (FIG. 4A). These astrocytes were able to survive and express the human astrocytic marker hGFAP after transplanting into mouse brains (FIG. 4B), generate $Ca^{2+}$ flux in response to ATP (FIG. 4C), and display a transient voltage-dependent outward current followed by a sustained lower current (FIG.

Example 3: AxD Astrocytes Exhibit Rosenthal Fiber-Like Structure

Figure 1G:
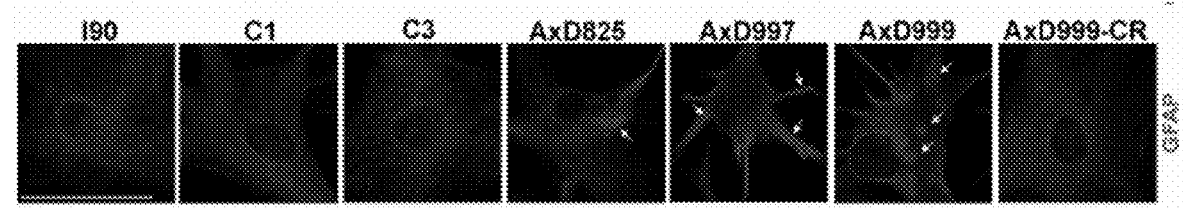
Figures 1H, 1I:
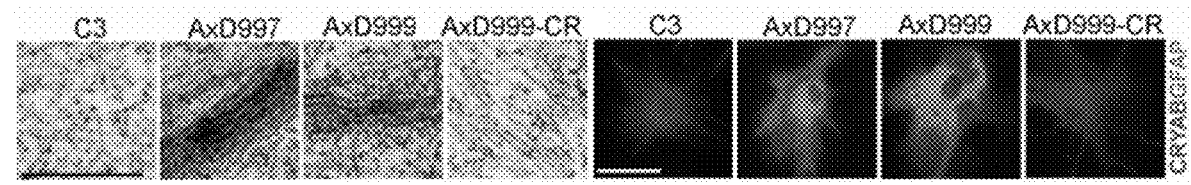

GFAP immunostaining revealed that the AxD astrocytes displayed patches of GFAP filament bundles or aggregates in the cytoplasm, in contrast to control astrocytes, in which the GFAP filaments are distributed evenly in the cytoplasm (FIGS. 1F, 1G). This observation was confirmed by electron microscopy (EM) analysis, which revealed dense aggregation of filaments in AxD astrocytes, resembling early Rosenthal fiber structure (FIG. 1H). In contrast, the AxD999-CR astrocytes did not exhibit bundles of GFAP filaments as revealed by both immunostaining (FIG. 1G) and EM analyses (FIG. 1H), in a manner similar to healthy control astrocytes. Because Rosenthal fibers are mostly composed of GFAP and the small heat shock proteins αB-crystallin (Tomokane et al., 1991), to confirm the presence of Rosenthal fibers in AxD astrocytes, the AxD astrocytes were immunostained for GFAP and αB-crystallin. Consistent with the EM analysis, GFAP and αB-crystallin double positive signal was observed in AxD astrocytes, but not in control astrocytes (C3 or AxD999-CR) that had the WT GFAP gene (FIG. 1I). These results indicate that the AxD iPSC-derived astrocytes exhibit structural difference in GFAP filaments from control iPSC-derived astrocytes, and that the Rosenthal fiber-like structure in AxD999 astrocytes was caused by GFAP mutation, because no such structure was detected in the isogenic AxD999-CR astrocytes that have the GFAP mutation corrected.

Example 4: AxD Astrocytes Reduce OPC Proliferation

Figure 6A:
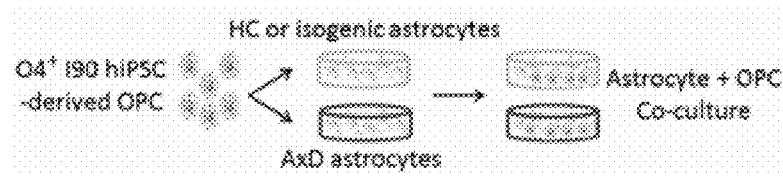
Figure 6B:
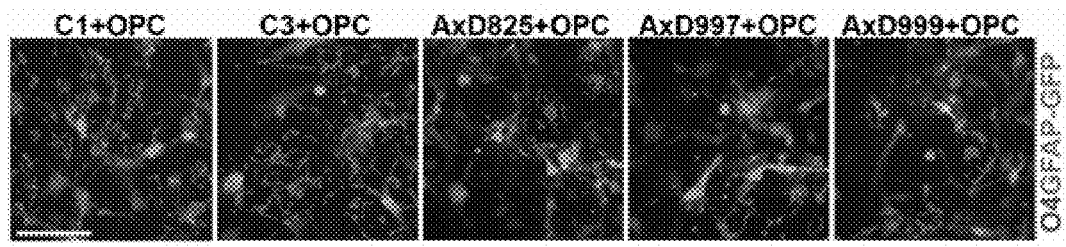
Figure 6C:
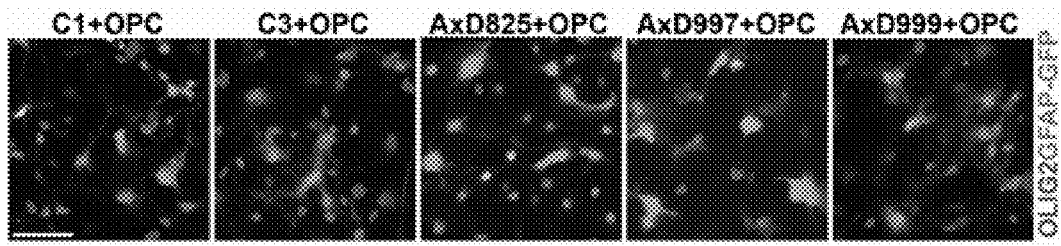
Figure 6D:
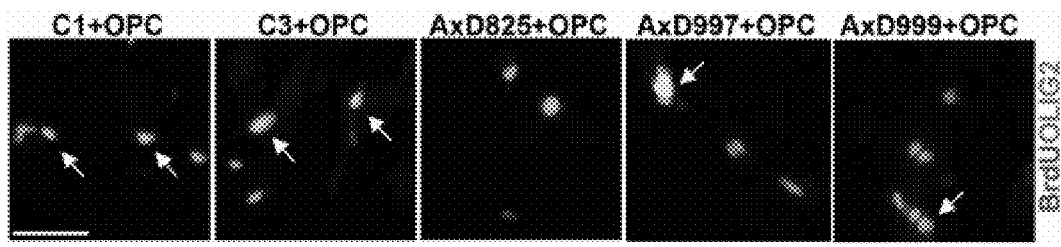
Figure 6E:
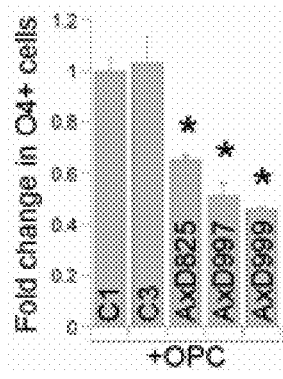
Figure 6F:
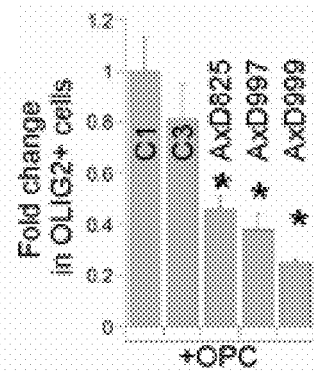

Because AxD is caused by mutation of the astrocytic gene GFAP, and myelination defect is the major pathological phenotype in AxD patients (Messing et al., 2012), it is hypothesized that AxD astrocytes could cause myelination defects through interaction with oligodendroglial lineage cells. To test this hypothesis, a co-culture system consisted of human iPSC-derived astrocytes and OPCs was established. Human healthy control iPSCs were differentiated into OLIG2$^+$ and NKX2.2*pre-OPCs, followed by induction into O4$^+$ OPCs (Douvaras and Fossati, 2015). The O4$^+$ OPCs were further matured into myelinating oligodendrocytes that expressed the mature oligodendrocyte marker myelin basic protein (MBP) (FIG. 5A). The co-culture system was set up by incubating the GFAP-GFP-sorted control or AxD astrocytes with the O4-sorted healthy control (HC) iPSC-derived OPCs (FIG. 6A). The sorted OPCs expressed the OPC markers O4 and OLIG2, but not the mature oligodendrocyte marker MBP (FIGS. 5B, 5C). Notably, a significant decrease in the number of O4+ OPCs was observed after 5-day co-culture of OPCs with AxD astrocytes, compared to co-culture with control astrocytes (FIGS. 6B, 6E). This observation was confirmed in a co-culture assay, in which the number of oligodendroglial lineage cells was evaluated by immunostaining with OLIG2 (FIGS. 6C, 6F). These results indicate that the AxD astrocytes could reduce the number of co-cultured OPCs.

Figure 6G:
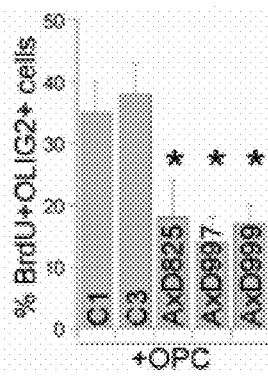

To test whether the decrease in the number of OPCs co-cultured with AxD astrocytes was due to a decrease of cell proliferation or an increase of cell death, apoptosis of OPCs in the co-culture system was examined by double staining for OLIG2 and cleaved Caspase-3, a marker of apoptosis. Barely any Caspase 3$^+$ OLIG2$^+$ cells were detected in any co-culture group (FIGS. 5D, 5E), indicating that the reduced cell number in OPCs is likely not resulted from increased OPC apoptosis. Next the rate of OPC proliferation in the co-culture system was examined. On day 2 of co-culture, cells were treated with BrdU. A significant decrease in the percentage of BrdU$^+$ OLIG2$^+$ OPCs was observed when co-cultured with AxD astrocytes, compared to that when co-cultured with control astrocytes (FIGS. 6D, 6G). In contrast, no difference in BrdU labeling was detected between control and AxD astrocytes (FIGS. 5F, 5G).

Figure 6H:
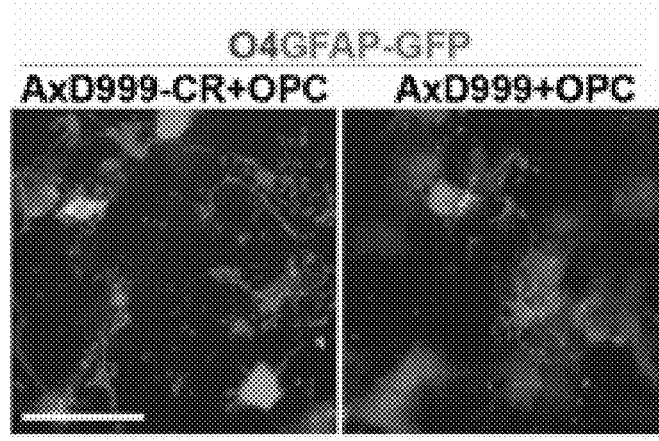
Figure 6I:
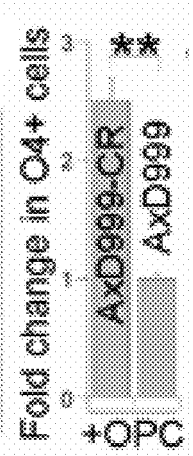

To determine whether the defects in OPC proliferation were caused by GFAP mutation in the co-cultured AxD astrocytes, the OPC proliferation rate between AxD999 and AxD999-CR co-cultures was compared. The number of OPCs significantly decreased in co-culture with AxD999 astrocytes, compared to that in co-culture with AxD999-CR astrocytes, as revealed by O4 staining (FIGS. 6H, 6I). Accordingly, a substantial decrease in OPC proliferation rate in co-culture with AxD999 astrocytes was observed, compared to that in co-culture with AxD999-CR astrocytes, as revealed by BrdU and OLIG2 double staining (FIGS. 6J, 6K). In summary, human iPSC-derived astrocyte and OPC co-culture allowed the study of the effects of AxD astrocytes on oligodendrocyte lineage cells. The results from this modeling system demonstrate that AxD astrocytes could reduce the number of co-cultured OPCs through inhibiting OPC proliferation.

Figure 7A:
Figure 7B:
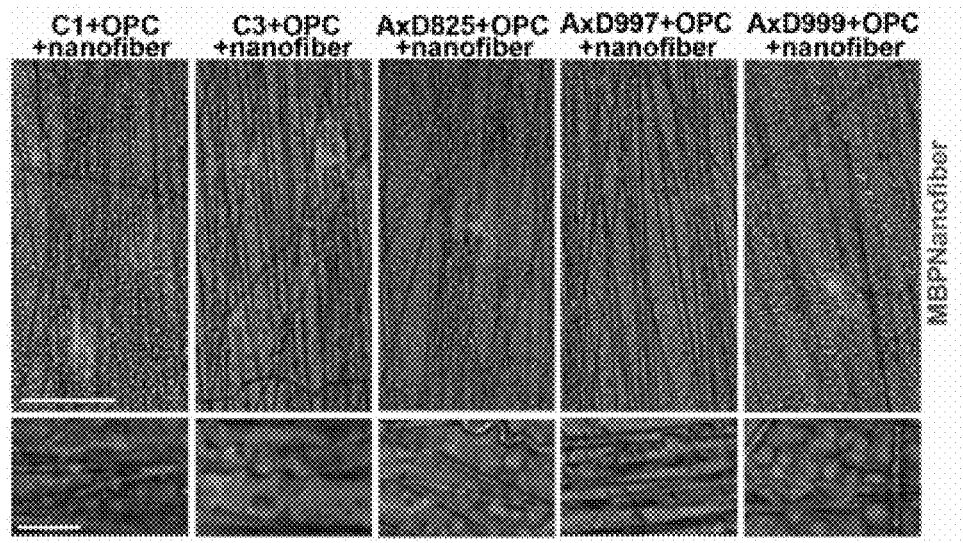
Figure 7B:
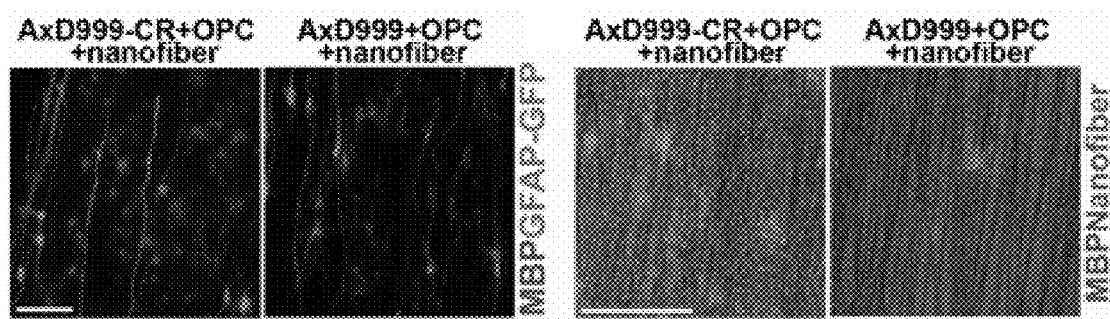
Figure 7E:
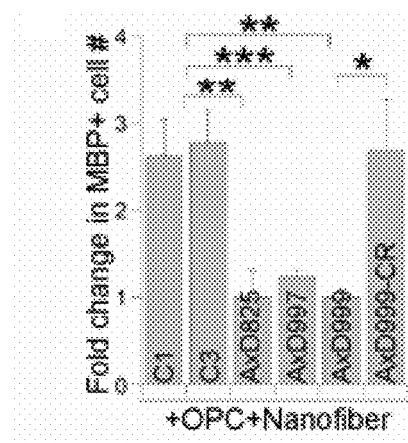
Figure 7F:
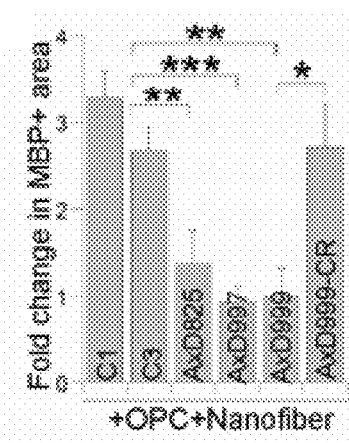
Figure 7G:
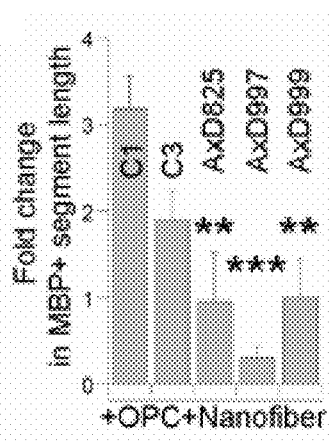

Example 5: AxD Astrocytes Induce Myelination Defect in a 3D Nanofiber Culture System Because OPCs are the precursors of myelinating oligodendrocytes, the observation that AxD astrocytes induced decreased OPC proliferation and reduced OPC cell number prompted a test to investigate if AxD astrocytes could induce myelination defects. To focus on the effect of astrocytes, without worrying about any potential effect from neurons, on myelination, OPCs and astrocytes were co-cultured on a neuron-free, 3D nanofiber scaffold for myelin wrapping (Lee et al., 2012; Ehrlich et al., 2017). Remarkably, substantially decreased number of MBP$^+$ oligodendrocytes and dramatically reduced area of MBP-covered nanofibers were found in the co-culture with AxD astrocytes, compared to that in the co-culture with control astrocytes (FIGS. 7A, 7B, 7E, 7F). The wrapping of the MBP$^+$ process along the nanofibers was further evaluated and substantially decreased length of the MBP+ nanofiber segments was observed in the co-culture with AxD astrocytes (FIGS. 7B, 7G). Collectively, these results demonstrate that the AxD astrocytes were able to induce decreased number of MBP$^+$ oligodendrocytes and reduced area of MBP-covered nanofibers, mimicking reduced area of myelination.

Figure 8A:
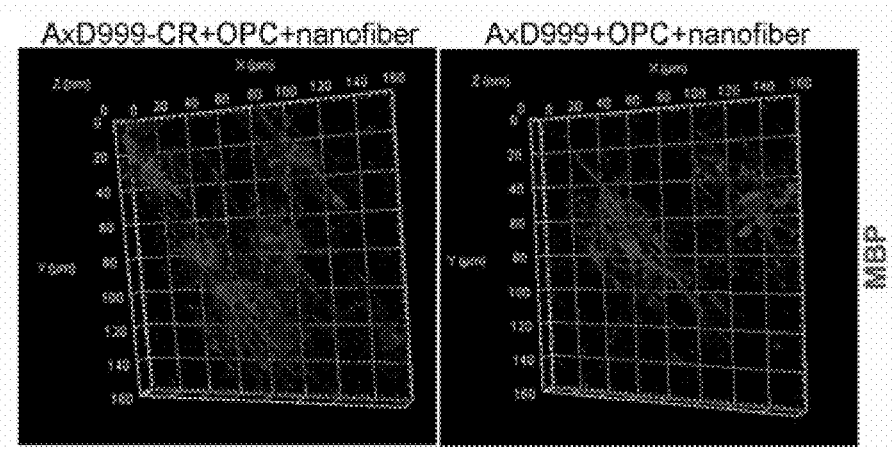
FIGS. 8A-8B show high resolution images of MBP signal on nanofibers.
Figure 8B:
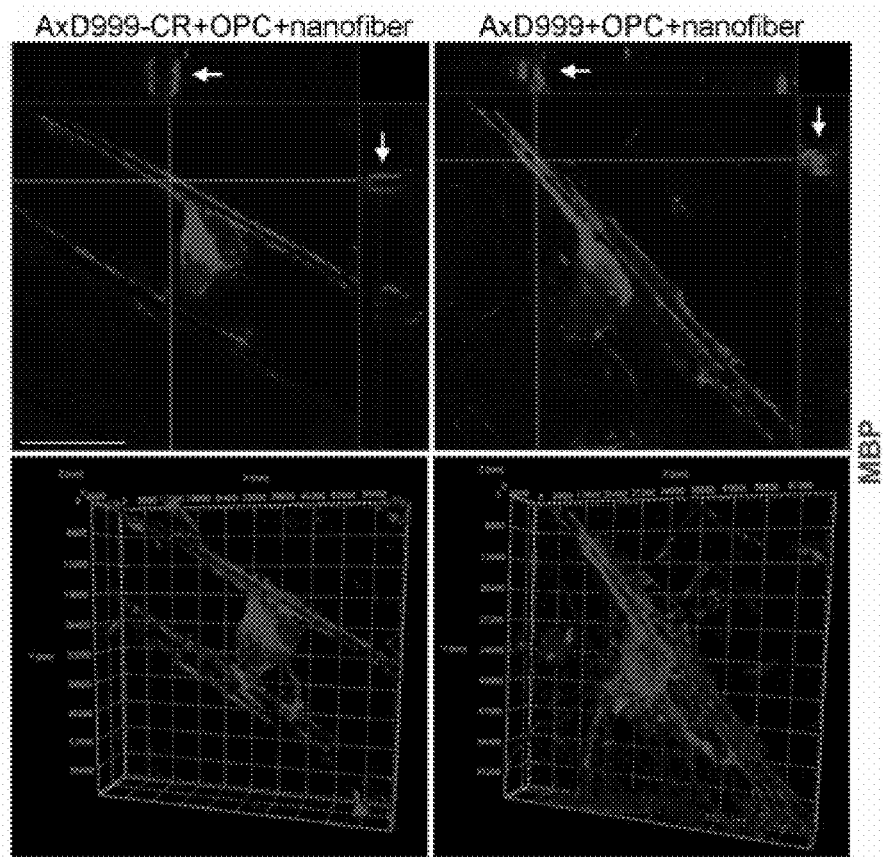

To evaluate the impact of astrocytic GFAP mutation on myelination, OPCs were co-cultures with AxD999 or AxD999-CR astrocytes on 3D nanofibers. The number of MBP$^+$ cells and the area of MBP-covered nanofibers (FIGS. 7C-7F, FIG. 8A) decreased substantially in the AxD999 co-culture, compared to that in the AxD999-CR co-culture. The reduced MBP-covered area is presumably due to decreased number of MBP$^+$ cells, because individual oligodendrocytes seemed to myelinate similarly when co-cultured with AxD999 or AxD999-CR astrocytes (FIG. 8B). These results together indicate that the defects of OPC proliferation and myelination in the co-culture are caused by GFAP mutation in the AxD astrocytes.

Example 6: AxD Astrocytes Exhibit Elevated Expression of Genes Associated with Cytokine Activity and Cell Membrane Because myelination defect could not be recapitulated in AxD animal models, the molecular and cellular mechanisms underlying the AxD pathology remain poorly understood. To identify key molecules that regulate the pathology of AxD, RNA-seq was performed using mRNAs isolated from healthy control or AxD iPSC-derived astrocytes. The control and AxD astrocytes were sorted by GFAP-based FACS using a method for analyzing RNA following intracellular sorting (MARIS) (Hrvatin et al., 2014) and mRNA was isolated from the sorted cells (FIG. 9A).

Comparing the transcriptome of AxD and control astrocytes revealed a set of differentially expressed genes between the two groups, including 128 significantly up-regulated and 104 significantly down-regulated genes in AxD astrocytes. Gene Ontology (GO) analysis revealed that genes significantly up-regulated in AxD astrocytes are involved in cell adhesion, cell membrane composition, immune cell activation and cytokine activity, whereas genes significantly down-regulated in AxD astrocytes are involved in supportive functions of astrocytes, such as synaptic transmission and ion transport (FIG. 9B). Three main categories of functions were selected and 20 to 22 representative genes that have |fold-change|>1.5 were listed in each category, including cytokine and secreted factors, cell membrane components and receptors, and intracellular signaling molecules (FIG. 9C). A subset of these genes was validated by quantitative RT-PCR (qRT-PCR). Up-regulation of CHI3L1, ITGB4, ITGB3, and down-regulation of TF in AxD astrocytes, compared to control astrocytes, was confirmed by qRT-PCR (FIGS. 9D-9G). These results together indicate that AxD astrocytes exhibit substantially different gene expression profile from control astrocytes, and this difference could contribute to the pathological phenotypes observed in AxD.

Example 7: AxD Patient Brains Exhibit Increased Expression of CHI3L1

To determine if the change in gene expression identified in AxD iPSC-derived astrocytes also occurs in AxD patient brains, AxD patient brain tissues were obtained along with age-matched non-AxD control brain tissues from NIH Neurobiobank (FIG. 10A). All brain tissues were from the frontal lobe cortex, because frontal lobe is the predominant region with white matter abnormalities in AxD patients (van der Knaap et al., 2001; van der Voornm et al., 2009). Characteristic Rosenthal fiber structures were detected in the AxD patient brains, but not in the non-AxD control brains (FIG. 10B). RNA-seq analysis identified genes that were differentially expressed between control and AxD brains (FIG. 11A). Compared to the control brains, 2,304 genes were up-regulated and 1,107 genes down-regulated in the AxD brains.

A number of genes showed the same trend of expression change in AxD brains as that in AxD astrocytes (FIG. 11B, Table 2). GO term analysis revealed that immune response, cytokine production, and cell membrane-related biology were among the functions associated with genes up-regulated in both AxD astrocytes and brains, whereas neural development-related processes, including axon ensheathment and myelination, were associated with genes down-regulated in both AxD astrocytes and brains (FIG. 11C).

In AxD brains, the myelination-related genes, including transcriptional factors that regulate myelin formation (e.g., ERMN, MYRF, NKX5-2) and components of myelin sheath (e.g., MOBP, MAG, MBP), were down-regulated in the RNA-seq analysis (FIG. 11D). The reduced expression of PDGFRA and MBP in AxD brains was confirmed by qRT-PCR (FIGS. 11F, 11G). The reduced expression of MBP was further confirmed using Western blot (FIG. 11I). In addition, representative genes in brain tissues related with cytokine and secreted molecules, and cell membrane components and receptors are shown (FIG. 11E, FIG. 10C). Among the top differentially expressed genes, CHI3L1 was significantly up-regulated in AxD brain tissues, which was confirmed by both qRT-PCR and Western blot (FIGS. 11H, 11I), consistent with the observation of up-regulated CHI3L1 expression in AxD astrocytes (FIGS. 9C, 9D). Moreover, correction of the GFAP mutation led to reduced CHI3L1 expression in AxD999-CR astrocytes, compared to that in AxD999 astrocytes (FIG. 12A). This result indicates that the GFAP mutation in AxD astrocytes is necessary for the elevated expression of CHI3L1.

Example 8: CHI3L1 Mediates the Inhibitory Effect of AxD Astrocytes on OPC Proliferation and Myelination Because CHI3L1 is a secreted molecule that is expressed by astrocytes (Bonneh-Barkay et al., 2010b; Singh et al., 2011), it was tested whether the conditioned medium (CM) from AxD astrocytes could inhibit OPC proliferation and whether blocking CHI3L1 in AxD CM using a neutralizing antibody could reverse the phenotype. A mild decrease in OPC proliferation upon treatment with AxD999 CM conditioned for 24 hr was observed, as revealed by BrdU and OLIG2 double staining. Significantly reduced OPC proliferation was observed when the co-culture was treated with AxD999 CM conditioned for 48 hr, compared to the treatment with control medium without conditioning (FIGS. 13A, 13B). Blocking CHI3L1 by a CHI3L1 neutralizing antibody reversed the inhibitory effect on OPC proliferation (FIGS. 13A, 13B), whereas a control IgG failed to reverse the inhibitory effect (FIG. 12B). These results indicate that secreted molecules from AxD astrocytes play an important role in inhibiting OPC proliferation and that CHI3L1 is an important mediator of such effect.

To further validate the role of astrocytic CHI3L1 in regulating OPC proliferation and myelination, AxD astrocytes were transfected with two shRNAs (shRNA-1 and shRNA-2) targeting different regions of the CHI3L1 gene or a control shRNA (shC). The knockdown (KD) of CHI3L1 mRNA level in the CHI3L1 shRNA-treated astrocytes was confirmed using qRT-PCR (FIG. 12C). KD of CHI3L1 in AxD astrocytes increased the number of OLIG2+ cells (FIGS. 12D, 12E) and enhanced the proliferation of OPCs co-cultured with these astrocytes, compared to that in co-culture with shC-treated AxD astrocytes (FIGS. 13C, 13D). Using the 3D nanofiber-based OPC-astrocyte co-culture system, it was found that KD of CHI3L1 in AxD astrocytes increased the number of MBP$^+$ cells and the area of MBP-covered nanofibers (MBP$^+$ area) in OPC co-cultured with AxD astrocytes (FIGS. 13E, 13F). This result demonstrates that KD of CHI3L1 in AxD astrocytes were able to ameliorate the inhibitory effect of AxD astrocytes on OPC proliferation and myelination. These results together suggest that CHI3L1 could play an important role in negatively regulating OPC proliferation and myelination.

The effect of CHI3L1 has been shown to be mediated by its receptor IL-13Rα2 and coreceptor TMEM219, or by the receptor CRTH2 (He et al., 2013; Zhou et al., 2014; Zhou et al., 2015; Lee et al., 2016). To explore potential receptors for CHI3L1 on OPCs, the expression of the putative CHI3L1 binding partners on OPCs was checked by live staining. While robust expression of IL-13Rα2 was detected on human fibrosarcoma HT1080 cells, no expression of IL-13Rα2 was detected on OPCs (FIG. 12F). Expression of CRTH2 and TMEM219 was observed on OPCs but not astrocytes (FIG. 12F). To determine if CHI3L1 could act through CRTH2 or TMEM219 to regulate OPC proliferation, CRTH2 or TMEM219 was blocked in the AxD999-CR astrocyte-OPC co-culture using their respective antibodies. Treatment of the co-culture with the CM of AxD999 astrocytes together with the CRTH2 antibody led to substantial rescue of the AxD999 astrocyte CM-induced reduction of OPC proliferation, whereas treatment with the AxD999 CM together with the TMEM219 antibody had minimal effect (FIGS. 14A, 14B). This result suggests that the astrocytic CHI3L1 could regulate OPC proliferation by binding to the OPC surface receptor CRTH2. To examine whether there is a species difference in CRTH2 expression in OPCs between mouse and human, the expression levels of CRTH2 in mouse and human OPCs were compared. Reduced level of CRTH2 mRNA expression was detected in mouse OPCs, compared to human OPCs (FIG. 12G). This result indicates that there is a species difference in CRTH2 expression in OPCs, which may partly contribute to the species difference of dysmyelination phenotype between mouse and human.

REFERENCES

The references, patents and published patent applications listed below, and all references cited in the specification above are hereby incorporated by reference in their entirety, as if fully set forth herein.

Abbott, N. J., Ronnback, L., and Hansson, E. (2006). Astrocyte-endothelial interactions at the blood-brain barrier. Nature reviews Neuroscience 7, 41-53.

Allen, N. J., and Eroglu, C. (2017). Cell Biology of Astrocyte-Synapse Interactions. Neuron 96, 697-708.

Anders, S., Pyl, P. T., and Huber, W. (2015). HTSeq-a Python framework to work with high-throughput sequencing data. Bioinformatics 31, 166-169.

Arion, D., Unger, T., Lewis, D. A., Levitt, P., and Mimics, K. (2007). Molecular evidence for increased expression of genes related to immune and chaperone function in the prefrontal cortex in schizophrenia. Biological psychiatry 62, 711-721.

Ashburner, M., Ball, C. A., Blake, J. A., Botstein, D., Butler, H., Cherry, J. M., Davis, A. P., Dolinski, K., Dwight, S. S., Eppig, J. T., et al. (2000). Gene ontology: tool for the unification of biology. The Gene Ontology Consortium. Nature genetics 25, 25-29.

Benjamini, Y., and Hochberg, Y. (1995). Controlling the false discovery rate: a practical and powerful approach to multiple testing. J R Stat Soc Series B (Methodological) 57.

Bhardwaj, R., Yester, J. W., Singh, S. K., Biswas, D. D., Surace, M. J., Waters, M. R., Hauser, K. F., Yao, Z., Boyce, B. F., and Kordula, T. (2015). RelB/p50 complexes regulate cytokine-induced YKL-40 expression. J Immunol 194, 2862-2870.

Bonneh-Barkay, D., Bissel, S. J., Kofler, J., Starkey, A., Wang, G., and Wiley, C. A. (2012). Astrocyte and macrophage regulation of YKL-40 expression and cellular response in neuroinflammation. Brain pathology (Zurich, Switzerland) 22, 530-546.

Bonneh-Barkay, D., Wang, G., Starkey, A., Hamilton, R. L., and Wiley, C. A. (2010a). In vivo CHI3L1 (YKL-40) expression in astrocytes in acute and chronic neurological diseases. Journal of neuroinflammation 7, 34.

Bonneh-Barkay, D., Zagadailov, P., Zou, H., Niyonkuru, C., Figley, M., Starkey, A., Wang, G., Bissel, S. J., Wiley, C. A., and Wagner, A. K. (2010b). YKL-40 expression in traumatic brain injury: an initial analysis. Journal of neurotrauma 27, 1215-1223.

Burman, J., Raininko, R., Blennow, K., Zetterberg, H., Axelsson, M., and Malmestrom, C. (2016). YKL-40 is a CSF biomarker of intrathecal inflammation in secondary progressive multiple sclerosis. Journal of neuroimmunology 292, 52-57.

Clarke, L. E., and Barres, B. A. (2013). Emerging roles of astrocytes in neural circuit development. Nature reviews 14, 311-321.

Colombo, E., and Farina, C. (2016). Astrocytes: Key Regulators of Neuroinflammation. Trends in immunology 37, 608-620.

Craig-Schapiro, R., Perrin, R. J., Roe, C. M., Xiong, C., Carter, D., Cairns, N. J., Mintun, M. A., Peskind, E. R., Li, G., Galasko, D. R., et al. (2010). YKL-40: a novel prognostic fluid biomarker for preclinical Alzheimer's disease. Biological psychiatry 68, 903-912.

Cui, Q., Shi, H., Ye, P., Li, L., Qu, Q., Sun, G., Sun, G., Lu, Z., Huang, Y., Yang, C. G., et al. (2017). m6A RNA Methylation Regulates the Self-Renewal and Tumorigenesis of Glioblastoma Stem Cells. Cell reports 18, 2622-2634.

Cui, Q., Yang, S., Ye, P., Tian, E., Sun, G., Zhou, J., Sun, G., Liu, X., Chen, C., Murai, K., et al. (2016). Downregulation of TLX induces TET3 expression and inhibits glioblastoma stem cell self-renewal and tumorigenesis. Nature communications 7, 10637.

Domingues, H. S., Portugal, C. C., Socodato, R., and Relvas, J. B. (2016). Oligodendrocyte, Astrocyte, and Microglia Crosstalk in Myelin Development, Damage, and Repair. Frontiers in cell and developmental biology 4, 71.

Douvaras, P., and Fossati, V. (2015). Generation and isolation of oligodendrocyte progenitor cells from human pluripotent stem cells. Nature protocols 10, 1143-1154.

Ehrlich, M., Mozafari, S., Glatza, M., Starost, L., Velychko, S., Hallmann, A. L., Cui, Q. L., Schambach, A., Kim, K. P., Bachelin, C., et al. (2017). Rapid and efficient generation of oligodendrocytes from human induced pluripotent stem cells using transcription factors. Proceedings of the National Academy of Sciences of the United States of America 114, E2243-E2252.

Gispert, J. D., Monte, G. C., Falcon, C., Tucholka, A., Rojas, S., Sanchez-Valle, R., Antonell, A., Llado, A., Rami, L., and Molinuevo, J. L. (2016). CSF YKL-40 and pTau181 are related to different cerebral morphometric patterns in early AD. Neurobiology of aging 38, 47-55.

Hagemann, T. L., Connor, J. X., and Messing, A. (2006). Alexander disease-associated glial fibrillary acidic protein mutations in mice induce Rosenthal fiber formation and a white matter stress response. J Neurosci 26, 11162-11173.

Hagemann, T. L., Gaeta, S. A., Smith, M. A., Johnson, D. A., Johnson, J. A., and Messing, A. (2005). Gene expression analysis in mice with elevated glial fibrillary acidic protein and Rosenthal fibers reveals a stress response followed by glial activation and neuronal dysfunction. Human molecular genetics 14, 2443-2458.

Harizi, H. (2013). The immunobiology of prostanoid receptor signaling in connecting innate and adaptive immunity. BioMed research international 2013, 683405.

Hasel, P., Dando, O., Jiwaji, Z., Baxter, P., Todd, A. C., Heron, S., Markus, N. M., McQueen, J., Hampton, D. W., Torvell, M., et al. (2017). Neurons and neuronal activity control gene expression in astrocytes to regulate their development and metabolism. Nature communications 8, 15132.

He, C. H., Lee, C. G., Dela Cruz, C. S., Lee, C. M., Zhou, Y., Ahangari, F., Ma, B., Herzog, E. L., Rosenberg, S. A., Li, Y., et al. (2013). Chitinase 3-like 1 regulates cellular and tissue responses via IL-13 receptor alpha2. Cell reports 4, 830-841.

Hinsinger, G., Galeotti, N., Nabholz, N., Urbach, S., Rigau, V., Demattei, C., Lehmann, S., Camu, W., Labauge, P., Castelnovo, G., et al. (2015). Chitinase 3-like proteins as diagnostic and prognostic biomarkers of multiple sclerosis. Multiple sclerosis 21, 1251-1261.

Hockemeyer, D., and Jaenisch, R. (2016). Induced Pluripotent Stem Cells Meet Genome Editing. Cell stem cell 18, 573-586.

Hrvatin, S., Deng, F., O'Donnell, C. W., Gifford, D. K., and Melton, D. A. (2014). MARIS: method for analyzing RNA following intracellular sorting. PloS one 9, e89459.

Hsu, F., Kent, W. J., Clawson, H., Kuhn, R. M., Diekhans, M., and Haussler, D. (2006). The UCSC Known Genes. Bioinformatics 22, 1036-1046.

Iwaki, T., Kume-Iwaki, A., Liem, R. K., and Goldman, J. E. (1989). Alpha B-crystallin is expressed in non-lenticular tissues and accumulates in Alexander's disease brain. Cell 57, 71-78.

Johnson, A. B., and Bettica, A. (1989). On-grid immunogold labeling of glial intermediate filaments in epoxy-embedded tissue. The American journal of anatomy 185, 335-341.

Kim, D., Pertea, G., Trapnell, C., Pimentel, H., Kelley, R., and Salzberg, S. L. (2013). TopHat2: accurate alignment of transcriptomes in the presence of insertions, deletions and gene fusions. Genome Biology 14, 1-13.

Kime, C., Rand, T. A., Ivey, K. N., Srivastava, D., Yamanaka, S., and Tomoda, K. (2015). Practical Integration-Free Episomal Methods for Generating Human Induced Pluripotent Stem Cells. Curr Protoc Hum Genet 87, 21 22 21-21 22 21.

Kiray, H., Lindsay, S. L., Hosseinzadeh, S., and Barnett, S. C. (2016). The multifaceted role of astrocytes in regulating myelination. Exp Neurol 283, 541-549.

Kondo, T., Funayama, M., Miyake, M., Tsukita, K., Era, T., Osaka, H., Ayaki, T., Takahashi, R., and Inoue, H. (2016). Modeling Alexander disease with patient iPSCs reveals cellular and molecular pathology of astrocytes. Acta neuropathologica communications 4, 69.

Krencik, R., Weick, J. P., Liu, Y., Zhang, Z. J., and Zhang, S. C. (2011). Specification of transplantable astroglial subtypes from human pluripotent stem cells. Nature biotechnology 29, 528-534.

Krencik, R., and Zhang, S. C. (2011). Directed differentiation of functional astroglial subtypes from human pluripotent stem cells. Nature protocols 6, 1710-1717.

Lanciotti, A., Brignone, M. S., Bertini, E., Petrucci, T. C., Aloisi, F., and Ambrosini, E. (2013). Astrocytes: Emerging Stars in Leukodystrophy Pathogenesis. Translational neuroscience 4.

Lawrence, M., Huber, W., Pagès, H., Aboyoun, P., Carlson, M., Gentleman, R., Morgan, M. T., and Carey, V. J. (2013). Software for Computing and Annotating Genomic Ranges. PLOS Computational Biology 9, e1003118.

Lee, C. M., He, C. H., Nour, A. M., Zhou, Y., Ma, B., Park, J. W., Kim, K. H., Dela Cruz, C., Sharma, L., Nasr, M. L., et al. (2016). IL-13Ralpha2 uses TMEM219 in chitinase 3-like-1-induced signalling and effector responses. Nature communications 7, 12752.

Lee, S., Leach, M. K., Redmond, S. A., Chong, S. Y., Mellon, S. H., Tuck, S. J., Feng, Z. Q., Corey, J. M., and Chan, J. R. (2012). A culture system to study oligodendrocyte myelination processes using engineered nanofibers. Nature methods 9, 917-922.

Lee, S. H., Nam, T. S., Kim, K. H., Kim, J. H., Yoon, W., Heo, S. H., Kim, M. J., Shin, B. A., Perng, M. D., Choy, H. E., et al. (2017). Aggregation-prone GFAP mutation in Alexander disease validated using a zebrafish model. BMC neurology 17, 175.

Li, L., Chao, J., and Shi, Y. (2017). Modeling neurological diseases using iPSC-derived neural cells: iPSC modeling of neurological diseases. Cell and tissue research.

Love, M. I., Huber, W., and Anders, S. (2014). Moderated estimation of fold change and dispersion for RNA-seq data with DESeq2. Genome Biology 15, 550.

Marchetto, M. C., Brennand, K. J., Boyer, L. F., and Gage, F. H. (2011). Induced pluripotent stem cells (iPSCs) and neurological disease modeling: progress and promises. Human molecular genetics 20, R109-115.

Messing, A., Brenner, M., Feany, M. B., Nedergaard, M., and Goldman, J. E. (2012). Alexander Disease. J Neurosci 32, 5017-5023.

Messing, A., Daniels, C. M., and Hagemann, T. L. (2010). Strategies for treatment in Alexander disease. Neurotherapeutics 7, 507-515.

Messing, A., Goldman, J. E., Johnson, A. B., and Brenner, M. (2001). Alexander disease: new insights from genetics. Journal of neuropathology and experimental neurology 60, 563-573.

Messing, A., Head, M. W., Galles, K., Galbreath, E. J., Goldman, J. E., and Brenner, M. (1998). Fatal encephalopathy with astrocyte inclusions in GFAP transgenic mice. The American journal of pathology 152, 391-398.

Molofsky, A. V., Krencik, R., Ullian, E. M., Tsai, H. H., Deneen, B., Richardson, W. D., Barres, B. A., and Rowitch, D. H. (2012). Astrocytes and disease: a neurodevelopmental perspective. Genes & development 26, 891-907.

Murai, K., Sun, G., Ye, P., Tian, E., Yang, S., Cui, Q., Sun, G., Trinh, D., Sun, O., Hong, T., et al. (2016). The TLX-miR-219 cascade regulates neural stem cell proliferation in neurodevelopment and schizophrenia iPSC model. Nature communications 7, 10965.

Olabarria, M., Putilina, M., Riemer, E. C., and Goldman, J. E. (2015). Astrocyte pathology in Alexander disease causes a marked inflammatory environment. Acta neuropathologica 130, 469-486.

Prust, M., Wang, J., Morizono, H., Messing, A., Brenner, M., Gordon, E., Hartka, T., Sokohl, A., Schiffmann, R., Gordish-Dressman, H., et al. (2011). GFAP mutations, age at onset, and clinical subtypes in Alexander disease. Neurology 77, 1287-1294.

Qu, Q., Sun, G., Li, W., Yang, S., Ye, P., Zhao, C., Yu, R. T., Gage, F. H., Evans, R. M., and Shi, Y. (2010). Orphan nuclear receptor TLX activates Wnt/beta-catenin signalling to stimulate neural stem cell proliferation and self-renewal. Nature cell biology 12, 31-40; sup pp 31-39.

Ran, F. A., Hsu, P. D., Lin, C. Y., Gootenberg, J. S., Konermann, S., Trevino, A. E., Scott, D. A., Inoue, A., Matoba, S., Zhang, Y., et al. (2013a). Double nicking by RNA-guided CRISPR Cas9 for enhanced genome editing specificity. Cell 154, 1380-1389.

Ran, F. A., Hsu, P. D., Wright, J., Agarwala, V., Scott, D. A., and Zhang, F. (2013b). Genome engineering using the CRISPR-Cas9 system. Nature protocols 8, 2281-2308.

Rempe, D. A., and Nedergaard, M. (2010). Targeting glia for treatment of neurological disease. Neurotherapeutics 7, 335-337.

Sanfilippo, C., Longo, A., Lazzara, F., Cambria, D., Distefano, G., Palumbo, M., Cantarella, A., Malaguamera, L., and Di Rosa, M. (2017). CHI3L1 and CHI3L2 overexpression in motor cortex and spinal cord of sALS patients. Molecular and cellular neurosciences 85, 162-169.

Shi, Y., Inoue, H., Wu, J. C., and Yamanaka, S. (2017). Induced pluripotent stem cell technology: a decade of progress. Nature reviews Drug discovery 16, 115-130.

Shi, Y., Lie, C. D., Taupin, P., Nakashima, K., Ray, J., Yu, R. T., Gage, F. H., and Evans, R. M. (2004). Expression and function of orphan nuclear receptor TLX in adult neural stem cells. Nature 427, 78-83.

Singh, S. K., Bhardwaj, R., Wilczynska, K. M., Dumur, C. I., and Kordula, T. (2011). A complex of nuclear factor I-X3 and STAT3 regulates astrocyte and glioma migration through the secreted glycoprotein YKL-40. The Journal of biological chemistry 286, 39893-39903.

Sloan, S. A., Darmanis, S., Huber, N., Khan, T. A., Birey, F., Caneda, C., Reimer, R., Quake, S. R., Barres, B. A., and Pasca, S. P. (2017). Human Astrocyte Maturation Captured in 3D Cerebral Cortical Spheroids Derived from Pluripotent Stem Cells. Neuron 95, 779-790 e776.

Sofroniew, M. V., and Vinters, H. V. (2010). Astrocytes: biology and pathology. Acta neuropathologica 119, 7-35.

Takahashi, K., Tanabe, K., Ohnuki, M., Narita, M., Ichisaka, T., Tomoda, K., and Yamanaka, S. (2007). Induction of pluripotent stem cells from adult human fibroblasts by defined factors. Cell 131, 861-872.

Taketomi, Y., Ueno, N., Kojima, T., Sato, H., Murase, R., Yamamoto, K., Tanaka, S., Sakanaka, M., Nakamura, M., Nishito, Y., et al. (2013). Mast cell maturation is driven via a group III phospholipase A2-prostaglandin D2-DP1 receptor paracrine axis. Nature immunology 14, 554-563.

Tanaka, K., Lee, H. U., and Ikenaka, K. (2007a). [Generation of mice with glial cell dysfunction]. Brain and nerve=Shinkei kenkyu no shinpo 59, 747-753.

Tanaka, K. F., Takebayashi, H., Yamazaki, Y., Ono, K., Naruse, M., Iwasato, T., Itohara, S., Kato, H., and Ikenaka, K. (2007b). Murine model of Alexander disease: analysis of GFAP aggregate formation and its pathological significance. Glia 55, 617-631.

Tomokane, N., Iwaki, T., Tateishi, J., Iwaki, A., and Goldman, J. E. (1991). Rosenthal fibers share epitopes with alpha B-crystallin, glial fibrillary acidic protein, and ubiquitin, but not with vimentin. Immunoelectron microscopy with colloidal gold. The American journal of pathology 138, 875-885.

van der Knaap, M. S., Naidu, S., Breiter, S. N., Blaser, S., Stroink, H., Springer, S., Begeer, J. C., van Coster, R., Barth, P. G., Thomas, N. H., et al. (2001). Alexander disease: diagnosis with MR imaging. Ajnr 22, 541-552.

van der Voornm, J. P., Pouwels, P. J., Salomons, G. S., Barkhof, F., and van der Knaap, M. S. (2009). Unraveling pathology in juvenile Alexander disease: serial quantitative MR imaging and spectroscopy of white matter. Neuroradiology 51, 669-675.

Verkhratsky, A., and Parpura, V. (2016). Astrogliopathology in neurological, neurodevelopmental and psychiatric disorders. Neurobiol Dis 85, 254-261.

Verkhratsky, A., Sofroniew, M. V., Messing, A., Delanerolle, N. C., Rempe, D., Rodriguez Arellano, J. J., and Nedergaard, M. (2012). Neurological diseases as primary gliopathies: A reassessment of neurocentrism. ASN neuro doi: 10.1042/AN20120010.

Wang, L., Colodner, K. J., and Feany, M. B. (2011). Protein misfolding and oxidative stress promote glial-mediated neurodegeneration in an Alexander disease model. J Neurosci 31, 2868-2877.

Wang, L., Hagemann, T. L., Kalwa, H., Michel, T., Messing, A., and Feany, M. B. (2015). Nitric oxide mediates glial-induced neurodegeneration in Alexander disease. Nature communications 6, 8966.

Wen, Z., Nguyen, H. N., Guo, Z., Lalli, M. A., Wang, X., Su, Y., Kim, N. S., Yoon, K. J., Shin, J., Zhang, C., et al. (2014a). Synaptic dysregulation in a human iPS cell model of mental disorders. Nature.

Wen, Z., Nguyen, H. N., Guo, Z., Lalli, M. A., Wang, X., Su, Y., Kim, N. S., Yoon, K. J., Shin, J., Zhang, C., et al. (2014b). Synaptic dysregulation in a human iPS cell model of mental disorders. Nature 515, 414-418.

Young, M. D., Wakefield, M. J., Smyth, G. K., and Oshlack, A. (2010). Gene ontology analysis for RNA-seq: accounting for selection bias. Genome biology 11, R14.

Yu, J., Vodyanik, M. A., Smuga-Otto, K., Antosiewicz-Bourget, J., Frane, J. L., Tian, S., Nie, J., Jonsdottir, G. A., Ruotti, V., Stewart, R., et al. (2007). Induced pluripotent stem cell lines derived from human somatic cells. Science (New York, N. Y. 318, 1917-1920.

Zhang, Y., Sloan, S. A., Clarke, L. E., Caneda, C., Plaza, C. A., Blumenthal, P. D., Vogel, H., Steinberg, G. K., Edwards, M. S., Li, G., et al. (2016). Purification and Characterization of Progenitor and Mature Human Astrocytes Reveals Transcriptional and Functional Differences with Mouse. Neuron 89, 37-53.

Zhou, Y., He, C. H., Herzog, E. L., Peng, X., Lee, C. M., Nguyen, T. H., Gulati, M., Gochuico, B. R., Gahl, W. A., Slade, M. L., et al. (2015). Chitinase 3-like-1 and its receptors in Hermansky-Pudlak syndrome-associated lung disease. The Journal of clinical investigation 125, 3178-3192.

Zhou, Y., Peng, H., Sun, H., Peng, X., Tang, C., Gan, Y., Chen, X., Mathur, A., Hu, B., Slade, M. D., et al. (2014). Chitinase 3-like 1 suppresses injury and promotes fibroproliferative responses in Mammalian lung fibrosis. Science translational medicine 6, 240ra276.

What is claimed is:

1. A method of determining if abnormal expression of a Chitinase-3-like 1 protein (CHI3L1) gene and/or a CHI3L1 receptor is associated with a neurological disease, comprising:

differentiating astrocytes from induced pluripotent stem cells (iPSCs) obtained from one or more healthy control subjects;

differentiating astrocytes from iPSCs obtained from a subject suffering from the neurological disease;

performing a transcriptome analysis of the astrocytes derived from the subject suffering from the neurological disease and a transcriptome analysis of the astrocytes derived from the one or more healthy control subjects;

comparing the results of both transcriptome analyses to determine if the CHI3L1 gene and/or the CHI3L1 receptor are substantially differentially expressed in the subject suffering from the neurological disease compared to the one or more healthy subjects; and if the CHI3L1 gene and/or a CHI3L1 receptor are differentially expressed; and correcting the expression of the CHI3L1 gene and/or the CHI3L1 receptor, wherein complete or partial restoration of one or more phenotypes of the neurological disease after correcting expression of the CHI3L1 gene and/or the CHI3L1 receptor indicates that the CHI3L1 gene and/or the CHI3L1 receptor are associated with the neurological disease.

2. The method of claim 1, wherein gene expression of the CHI3L1 gene and/or the CHI3L1 receptor is up-regulated in the subject suffering from the neurological disease and the abnormal gene expression is corrected by administering an effective amount of an inhibitor of the CHI3L1 gene and/or the CHI3L1 receptor to the subject.

3. The method of claim 2, wherein the inhibitor comprises a siRNA or a shRNA targeting the up-regulated CHI3L1 gene and/or CHI3L1 receptor gene, CRISPR/Cas9-mediated inhibition (CRISPRi), CRISPR/Cas9-mediated gene knockout, a neutralizing antibody, and a small molecule compound that inhibits the expression of the CHI3L1 gene and/or the CHI3L1 receptor.

4. The method of claim 1, wherein one or more genes are down-regulated in the subject suffering from the neurological disease and the abnormal gene expression is corrected by administering an effective amount of CRISPR/Cas9-mediated activation (CRISPRa) or a small molecule compound that activates the expression of the down-regulated gene to the subject.

5. The method of claim 1, wherein the neurological disease is associated with astrocyte abnormalities.

6. The method of claim 1, wherein the neurological disease includes the Alexander disease, the Alzheimer's disease, the Parkinson disease, the Huntington disease, multiple sclerosis, and amyotrophic lateral sclerosis.

7. The method of claim 1, wherein the CHI3L1 receptor is Chemoattractant receptor-homologous molecule expressed on T Helper type 2 cells (CRTH2).

* * * * *